(12) United States Patent
Stevens et al.

(10) Patent No.: US 8,809,365 B2
(45) Date of Patent: Aug. 19, 2014

(54) 1-SUBSTITUTED 2-AZABICYCLO [3.1.1] HEPTYL DERIVATIVES USEFUL AS NICOTINIC ACETYLCHOLINE RECEPTOR MODULATORS FOR TREATING NEUROLOGIC DISORDERS

(75) Inventors: Christian Stevens, Merelbeke (BE); Ann De Blieck, Sinaai (BE); Thomas Heugebaert, Marke (BE)

(73) Assignee: Universiteit Gent, Ghent (BE)

( * ) Notice: Subject to any disclaimer, the term of this patent is extended or adjusted under 35 U.S.C. 154(b) by 223 days.

(21) Appl. No.: 13/504,618

(22) PCT Filed: Nov. 3, 2010

(86) PCT No.: PCT/EP2010/066764
§ 371 (c)(1),
(2), (4) Date: Apr. 27, 2012

(87) PCT Pub. No.: WO2011/054885
PCT Pub. Date: May 12, 2011

(65) Prior Publication Data
US 2012/0245196 A1 Sep. 27, 2012

Related U.S. Application Data

(63) Continuation-in-part of application No. 12/612,452, filed on Nov. 4, 2009, now Pat. No. 8,389,561.

(30) Foreign Application Priority Data

Nov. 4, 2009 (GB) .................................. 0919325.1

(51) Int. Cl.
*A61K 31/439* (2006.01)
*A61K 31/403* (2006.01)
*C07D 221/22* (2006.01)
*C07D 487/04* (2006.01)
*C07D 401/06* (2006.01)
*C07D 401/12* (2006.01)

(52) U.S. Cl.
CPC ............ *C07D 401/06* (2013.01); *C07D 487/04* (2013.01); *C07D 401/12* (2013.01)
USPC ........... 514/299; 546/112; 548/452; 548/465; 514/413

(58) Field of Classification Search
USPC ............ 514/413, 299; 548/452, 465; 546/112
See application file for complete search history.

(56) References Cited

U.S. PATENT DOCUMENTS

| 5,510,490 | A | 4/1996 | Pandey et al. |
| 5,817,679 | A | 10/1998 | Shen et al. |
| 6,060,473 | A | 5/2000 | Shen et al. |
| 6,077,846 | A | 6/2000 | Qian et al. |
| 6,117,889 | A | 9/2000 | Shen et al. |
| 6,562,816 | B2 | 5/2003 | Wishka et al. |
| 7,884,125 | B2 | 2/2011 | Stevens et al. |
| 2009/0275616 | A1 | 11/2009 | Stevens et al. |
| 2010/0093807 | A1 | 4/2010 | Stevens et al. |

FOREIGN PATENT DOCUMENTS

| CA | 2 638 573 | 10/2009 | |
| EP | 0 657 455 | 6/1995 | |
| EP | 0 955 301 A2 | 11/1999 | |
| WO | WO 90/07503 | 7/1990 | |
| WO | WO 90/07503 A1 | 7/1990 | |
| WO | WO 00/23424 | 4/2000 | |
| WO | WO 2007/137030 | 11/2007 | |
| WO | WO-2007/137030 A2 * | 11/2007 | ............. A61K 31/43 |
| WO | WO 2011/054885 | 5/2011 | |

OTHER PUBLICATIONS

Cheng et al., "Synthesis and Biological Evaluation at Nicotinic Acetylcholine Receptors of N-Arylalkyl-and N-Aryl-7-Azabicyclo[2.2.1]heptanes," *J. Med. Chem.* 45:3041-3047 (2002).
Krow et al., "Synthesis of 5- and 6-(6-Chloro-3-pyridyl)-2-azabicyclo[2.2.0]hexanes. Epibatidine Analogs," *Tetrahedron* 56:9233-9239 (2000).
Xu et al., "Conformationally Constrained Nicotines. 1-Pyridinyl-7-azabicyclo[2.2.1]heptane and 1-Pyridinyl-8-azabicyclo[3.2.1]octane Analogues," *J. Org. Chem.* 64:4069-4078 (1999).
Notification of Transmittal of the International Search Report and the Written Opinion of the International Searching Authority; International Search Report; and Written Opinion in International Application No. PCT/EP2010/066764, mailed Apr. 8, 2011 (13 pages).
Cheng et al., "Synthesis and Biological Evaluation at Nicotinic Acetylcholine Receptors of N-Arylalkyl- and N-Aryl-7-Azabicyclo[2.2.1]heptanes," *J. Med. Chem.* 45: 3041-3047 (2002).
Dunlop et al., "In Vitro Screening Strategies for Nicotinic Receptor Ligands" *Biochemical Pharmacology* 74:1172- 1181 (2007).
Grygorenko et al., "Stereoselective Synthesis of 2,4-methanoproline Homologues" *Tetrahedron: Asymmetry* 17:252-258 (2006).
Krow et al., "Synthesis of 5- and 6-(6-Chloro-3-pyridyl)-2-azabicyclo[2.2.0]hexanes. Epibatidine Analogs," *Tetrahedron* 56: 9233-9239 (2000).
Radchenko et al., "Conformationally Restricted Nonchiral Pipecolic Acid Analogues," *J. Org. Chem.* 74(15):5541-5544 (2009).
Xu et al., "Conformationally Constrained Nicotines. 1-Pyridinyl-7-azabicyclo[2.2.1]heptane and 1-Pyridinyl-8-azabicyclo[3.2.1]octane Analogues," *J. Org. Chem.* 64: 4069-4078 (1999).
International Preliminary Report on Patentabilitty for International Application No. PCT/EP2010/066764, issued May 8, 2012 (9 pages).
International Search Report for International Application No. PCT/EP2010/066764, dated Feb. 28, 2011 (dated of completion of search) and Apr. 8, 2011 (date of mailing of report) (4 pages).

(Continued)

*Primary Examiner* — Kamal Saeed
*Assistant Examiner* — Janet L Coppins
(74) *Attorney, Agent, or Firm* — Clark & Elbing LLP

(57) ABSTRACT

This invention provides 2-azabicyclo[3.1.1]heptyl derivatives, and methods for producing them, which are useful therapeutic agents for preventing or treating central nervous system disorders and disease mediated by a Nicotinic Acetylcholine Receptor such as, but not limited to, Alzheimer's disease, Parkinson's disease, schizophrenia, epilepsy, dementia, pain and nicotine addiction.

20 Claims, No Drawings

(56) References Cited

OTHER PUBLICATIONS

Written Opinion of the International Searching Authority for International Application No. PCT/EP2010/066764, dated Feb. 28, 2011 (dated of completion of search) and Apr. 8, 2011 (date of mailing of report) (8 pages).
Search Report for British Patent Application No. GB 0919325.1, dated Mar. 1, 2010 (2 pages).
Office Action issued in U.S. Appl. No. 12/188,524, dated Mar. 29, 2010 (21 pages).
Office Action issued in U.S. Appl. No. 12/612,452, dated Jun. 14, 2012 (32 pages).
Office Communication for Canadian Patent Application No. 2,638,573, dated Jan. 20, 2012 (2 pages).
International Preliminary Report on Patentability issued in International Application No. PCT/EP2010/066764, issued May 8, 2012 (9 pages).

* cited by examiner

1-SUBSTITUTED 2-AZABICYCLO [3.1.1] HEPTYL DERIVATIVES USEFUL AS NICOTINIC ACETYLCHOLINE RECEPTOR MODULATORS FOR TREATING NEUROLOGIC DISORDERS

CROSS-REFERENCE TO RELATED APPLICATIONS

This application is the U.S. National Stage filing under 35 U.S.C. §371 of International Application No. PCT/EP2010/066764, filed Nov. 3, 2010, which is a continuation-in-part of U.S. patent application Ser. No. 12/612,452, filed Nov. 4, 2009, and claims the benefit of Great Britain Patent Application No. 0919325.1, filed Nov. 4, 2009.

FIELD OF THE INVENTION

The present invention relates to a group of 1-substituted-2-azabicyclo-[3.1.1]heptyl derivatives with biological activity. The present invention also relates to synthetic methods for producing 1-substituted-2-azabicyclo-[3.1.1]heptyl derivatives belonging to this group. The present invention also relates to certain intermediates for producing such 1-substituted-2-azabicyclo-[3.1.1]heptyl derivatives, as well as a synthetic method for producing such intermediates. The present invention also relates to the nicotinic acetylcholine receptor modulating activity of these derivatives and, as a consequence, to pharmaceutical compositions comprising a therapeutically effective amount of such 1-substituted-2-azabicyclo-[3.1.1]heptyl derivatives, as well as their use as medicaments for the prevention and treatment of central nervous system disorders and diseases mediated by a Nicotinic Acetylcholine Receptor, such as pain, Alzheimer's disease, Parkinson's disease, schizophrenia, epilepsy and nicotine addiction.

BACKGROUND OF THE INVENTION

The alkaloid epibatidine was first isolated in 1974 from the skin of the Ecuadorian frog *Epipedobates tricolor*. Shortly afterwards, its analgesic potency was shown to be about 200-fold higher than that of morphine. Regrettably however, the toxicity of epibatidine is too high for any human therapeutic use. The mode of action of epibatidine was later revealed as a highly potent nicotinic acetylcholine receptor agonist. This membrane bound pentameric ion channel has been associated with many neurological disorders such as Alzheimer disease, Parkinson disease and schizophrenia. For each of these disorders, there is a shift in the prevalence of the different nicotinic actylcholine receptor subtypes.

In order to improve the ratio of pharmacological to toxicological activity, many analogues have been synthesized, most of them being substituted at position 2 of the 7-azabicyclo [2.2.1]heptyl ring. Radchenko et al disclosed in *J. Org. Chem.* (2009) 74:5541-5543 producing, with a 42% yield, 2-benzyl-2-azabicyclo-[3.1.1]heptane-1-carbonitrile by reacting 3-(2-chloroethyl)cyclobutanone with an equimolar amount of benzylamine and a threefold excess amount of acetone cyanohydrin.

As disclosed by Collingridge et al in *Neuropharmacology* (2009) 56:2-5 (especially table 1) and in accordance with the International Union of Pharmacology Committee on Receptor Nomenclature and Drug Classification, nicotinic acetylcholine receptors (hereinafter nAChR) belong to the Cys-loop superfamily of receptors (also including GABA, 5-HT$_3$, glycine and zinc activated receptors) which itself is part of ligand-gated ion channels activated by neurotransmitters (also named the neurotransmitter-gated ion channel superfamily).

nAChR are widely distributed throughout the central (CNS) and peripheral (PNS) nervous systems. Such receptors play an important role in regulating CNS function, particularly by modulating release of a wide range of neurotransmitters such as acetylcholine, norepinephrine, dopamine, serotonin and GABA, and are consequently involved in a wide variety of complex brain functions such as neurodegeneration, pain and inflammation, psychosis, mood and emotion, memory, attention and cognition as well as in pathological conditions such as Alzheimer's and Parkinson's disease, schizophrenia, epilepsy and nicotine addiction. At least 16 different genes code for nAChR subunits, which can assemble as pentamers in different combinations to form diverse nAChR subtypes. nAChR are ligand-gated ion channels formed by the assembly of five subunits (pentamers). Each subunit is comprised of a large extracellular N-terminal. The agonist binding site is located in the N-terminal, at the interface between two adjacent subunits. 17 distinct nAChR subunits have been identified. Besides the muscular nAChR subtypes, the neuronal nAChR can be divided in two groups:

α-bungarotoxin sensitive receptors which can be homomeric (being composed of five α7 or α9 subunits) or heteromeric (made up of different α7 or α9 or α10 subunits); and α-bungarotoxin insensitive receptors which consist of different heteromeric combinations of α (α2-α6) and β (β2-β4) subunits, whose prevalent stoichiometry is believed to be $(\alpha)_2(\beta)_3$.

The α7 subtype and the predominant α4β2 subtypes of nAChR have been recognized as being of major importance since they play a significant role in enhancing cognitive function, protection against neuron degeneration, schizophrenia and pain relief. The activity of both α7 and α4β2 nAChR can be modified or regulated by means of subtype-selective nAChR ligands which can exhibit antagonist, agonist or partial agonist properties. The number of binding sites depends on the number and type of α subunits: for instance in $(\alpha 7)_5$, five identical binding sites are present, whereas in $(\alpha 4)_2(\beta 2)_3$ there are two binding sites located at the interface between the α4 and β2 subunits.

α7 subunits uniquely and efficiently assemble into functional homopentameric acetylcholine-gated non selective cation channels when expressed in mammalian cells. The α4β2 and α3β4 subtypes are also well characterized in terms of ligand selectivity. A few other subtypes such as α2β4, α4β4, α3β2, and α1β1γδ, have also been evaluated for instance by Broad et al in *J. Pharmacol. Exper. Therap.* (2006) 318:1108-1117. There is currently significant interest in developing selective nAChR agonists and modulators, in particular selective ligands for the α7, α4β2, α3β4, α2β4, α4β4, α3β2, and α1β1γδ subtypes of nAChR, for the treatment of various neurological, neurodegenerative and psychiatric disorders.

There is still a need in the art for more subtype selective nAChR modulators in an effort to provide prevention or treatment for neurological, neurodegenerative and psychiatric diseases such as, but not limited to, Alzheimer disease, Parkinson disease, epilepsy, pain, nicotine addiction, mood instability, dementia and schizophrenia, as well as other CNS disorders such as impaired memory performance, impaired attention and cognitive deficit. The present invention intends to address one or more of these problems.

SUMMARY OF THE INVENTION

According to a first aspect, the present invention relates to a group of 1-substituted-2-azabicyclo[3.1.1]heptyl derivatives represented by the structural formula (I):

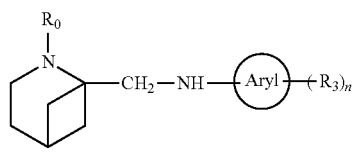

or the structural formula (II):

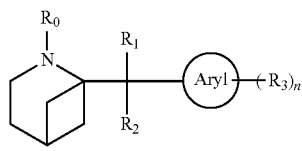

or the structural formula (III):

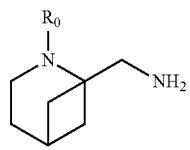

wherein:
   $R_0$ is hydrogen or a nitrogen-protecting group selected from the group consisting of phenyl, benzyl, heteroaryl, heteroarylmethyl, heteroarylethyl, phenylethyl, naphthylmethyl, naphthylethyl, butoxycarbonyl, $C_{3-4}$ alkenyl and $C_{1-8}$ alkyl, wherein said benzyl, phenyl or heteroaryl is optionally substituted with one to three substituents independently selected from the group consisting of halogen, $C_{1-4}$ alkyl, trifluoromethyl, $C_{1-4}$ alkoxy, trifluoromethoxy, dimethylaminoethoxy, dimethylaminopropoxy, morpholinoethoxy, phenoxy, phenoxymethyl, heteroaryl and heteroarylmethyl;
   $R_1$ is hydrogen and $R_2$ is hydroxyl, or $R_1$ in combination with $R_2$ is oxo or imino;
   $R_3$ is a substituent selected from the group consisting of fluoro, chloro, bromo, $C_{1-4}$ alkyl, $C_{1-4}$ alkoxy, $C_{1-4}$ alkylthio, cyano, phenyl, trifluoromethyl, trifluoromethoxy, amino, dimethylamino, heteroaryl and tert-butylcarboxylate; and
   n is 0, 1, 2 or 3; and
   Aryl is an optionally substituted aryl or heteroaryl group, or a pharmaceutically acceptable salt thereof, or an enantiomer, or a stereoisomeric form thereof, or a solvate thereof.

According to a second aspect, the present invention relates to a method for producing 1-substituted-2-azabicyclo[3.1.1] heptyl derivatives represented by the structural formula (I) or the structural formula (III), a method for producing 1-substituted-2-azabicyclo[3.1.1]heptyl derivatives represented by the structural formula (II) wherein $R_1$ is hydrogen and $R_2$ is hydroxyl, and a method for producing 1-substituted-2-azabicyclo[3.1.1]heptyl derivatives represented by the structural formula (II) wherein $R_1$ in combination with $R_2$ is oxo.

According to a third aspect, the present invention relates to certain groups of 1-cyano-2-$R_0$-substituted-2-azabicyclo [3.1.1]heptanes, 1-formyl-2-$R_0$-substituted-2-azabicyclo [3.1.1]heptanes and 1-aminomethyl-2-$R_0$-substituted-2-azabicyclo[3.1.1]heptanes, wherein $R_0$ is hydrogen or a nitrogen-protecting group selected from the group consisting of phenyl, benzyl, naphthylmethyl, heteroaryl, heteroarylmethyl, heteroarylethyl, phenylethyl, naphthylethyl, butoxycarbonyl, $C_{3-4}$ alkenyl and $C_{1-8}$ alkyl, wherein said benzyl, phenyl or heteroaryl is optionally substituted with one to three substituents independently selected from the group consisting of halogen, $C_{1-8}$ alkyl, $C_{1-8}$ alkoxy, trifluoromethyl, trifluoromethoxy, dimethyl-aminoethoxy, dimethylaminopropoxy, morpholinoethoxy, phenoxy, phenoxy-methyl, heteroaryl and heteroarylmethyl, a method for producing them, and their use as intermediates for producing the 1-substituted-2-azabicyclo[3.1.1]heptyl derivatives represented by the structural formulae (I), (II) and (III).

According to a fourth aspect, the present invention relates to pharmaceutical compositions comprising a therapeutically effective amount of a 1-substituted-2-azabicyclo[3.1.1]heptyl derivative represented by the structural formula (I) or the structural formula (II) or the structural formula (III). These pharmaceutical compositions are useful for use as medicaments for the prevention or treatment of diseases mediated by a Nicotinic Acetylcholine Receptor or another receptor belonging to the Cys-loop superfamily of receptors, such as pain, Alzheimer's disease, Parkinson's disease, schizophrenia, epilepsy, dementia and nicotine addiction. These pharmaceutical compositions are also useful for the prevention or treatment of other CNS disorders such as impaired memory performance, impaired attention and cognitive deficit.

DEFINITIONS

As used herein with respect to a substituting group, and unless otherwise stated, the term "$C_{1-4}$ alkyl" means straight and branched chain saturated acyclic hydrocarbon monovalent groups having from 1 to 4 carbon atoms such as, for example, methyl, ethyl, propyl, n-butyl, 1-methylethyl (isopropyl), 2-methylpropyl(isobutyl) and 1,1-dimethylethyl (tert-butyl). By analogy, the term "$C_{1-8}$ alkyl" refers to such groups having from 1 to 8 carbon atoms, including 2-methylbutyl, n-pentyl, dimethylpropyl, n-hexyl, 2-methylpentyl, 3-methylpentyl, n-heptyl, n-octyl, and the like.

As used herein with respect to a substituting group, and unless otherwise stated, the term "aryl" designate any mono- or polycyclic aromatic monovalent hydrocarbon group having from 6 up to 30 carbon atoms such as but not limited to phenyl, naphthyl, anthracenyl, phenanthracyl, fluoranthenyl, chrysenyl, pyrenyl, biphenylyl, terphenyl, picenyl, indenyl, indacenyl, benzocyclobutenyl, benzocyclooctenyl and the like, including fused benzo-$C_{4-8}$ cycloalkyl groups such as, for instance, indanyl, tetrahydronaphthyl, fluorenyl and the like, all of the said groups being optionally substituted with one or more, preferably 1, 2, 3, 4 or 5, substituents independently selected from the group consisting of halogen, amino, trifluoromethyl, hydroxyl, sulfhydryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein with respect to a substituting group, and unless otherwise stated, the term "$C_{1-4}$ alkoxy" refers to substituents wherein a carbon atom of a $C_{1-4}$ alkyl group (such as defined herein), is attached to an oxygen atom through a single bond such as, but not limited to, methoxy, ethoxy, propoxy, n-butoxy, pentoxy, isopropoxy, sec-butoxy, and tert-butoxy.

As used herein and unless otherwise stated, the term "stereoisomeric form" refers to all possible different isomeric as well as conformational forms which the compounds of this invention may exhibit, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a derivative of this invention with a suitable inorganic solvent (e.g. hydrates) or a suitable organic solvent such as, but not limited to, alcohols (thus forming alcoholates), ketones, esters, ethers, nitriles (e.g. acetonitrile) and the like.

As used herein, the term "Parkinson's disease" refers to a chronic progressive nervous disease characterised by neurodegeneration, especially degeneration of dopaminergic neurons. Symptoms include stooped posture, resting tremor, weakness of resting muscles, a shuffling gait, speech impediments, movement difficulties and an eventual slowing of mental processes and dementia.

As used herein, the term "schizophrenia" refers to a complex psychosis characterised by abnormalities in perception, content of thought, and thought processes (hallucinations) and by extensive withdrawal of interest from the outside world and excessive focusing on one's own mental life.

As used herein, the term "dementia" refers to a pathologic condition characterised by disorientation, impaired memory and judgement, and the usually progressive loss of cognitive and intellectual functions without impairment of perception or consciousness. The term encompasses various specific forms such as, but not limited to, epileptic dementia, hebephrenic dementia, Lewy body dementia, presenile dementia and the like.

As used herein, the term "pain" refers to an unpleasant abnormal sensory or emotional experience subjectively described as a potential tissue damage, usually in response or due to a stimulus which does not normally provoke such experience. It includes pain initiated or caused by a lesion or dysfunction in the central nervous system, and other specific forms such as detailed in the 2007 edition of the pain terminology published by the International Association for the Study of Pain. This definition refers to use in clinical practice rather than for experimental work, physiology or anatomical purpose.

As used herein with respect to a substituting group, and unless otherwise stated, the term "heteroaryl" refers to a mono- or polycyclic, aromatically unsaturated monovalent hydrocarbon group having from 2 up to 15 carbon atoms and including one or more heteroatoms in one or more rings, each of said rings having from 3 to 10 atoms (and optionally further including one or more heteroatoms attached to one or more carbon atoms of said ring, for instance in the form of a carbonyl or thiocarbonyl or selenocarbonyl group, each of said heteroatoms being independently selected from the group consisting of nitrogen, oxygen and sulfur, also including groups wherein a heterocyclic ring is fused to one or more aromatic hydrocarbon rings for instance in the form of benzo-fused, dibenzo-fused or naphtho-fused heterocyclic groups; and also including groups wherein each carbon atom of each ring may furthermore be independently substituted with a substituent selected from the group consisting of halogen, nitro, $C_{1-4}$ alkyl (optionally containing, in the main chain or a side chain, one or more atoms or groups such as oxo, hydroxyl, ether, thioether, acetal, amino, or halogen). Within the framework of the present invention, heteroaryl groups including one or more nitrogen atoms in one or more rings are highly preferred. Within the broad definition hereinabove are included heterocyclic aromatically unsaturated groups such as, but not limited to, diazepinyl, oxadiazinyl, thiadiazinyl, dithiazinyl, triazolonyl, diazepinonyl, triazepinyl, triazepinonyl, tetrazepinonyl, benzoquinolinyl, benzothiazinyl, benzothiazinonyl, benzoxathiinyl, benzodioxinyl, benzodithiinyl, benzoxazepinyl, benzothiazepinyl, benzodiazepinyl, benzodioxepinyl, benzodithiepinyl, benzoxazocinyl, benzothiazocinyl, benzodiazocinyl, benzoxathiazepinyl, benzoxadiazepinyl, benzothiadiazepinyl, benzotriazepinyl, benzoxathiepinyl, benzotriazinonyl, benzoxazolinonyl, azetidinonyl, azaspiroundecyl, selenazinyl, selenazolyl, azahypoxanthinyl, bipyrazinyl, bipyridinyl, oxazolidinyl, diselenopyrimidinyl, benzopyrenyl, benzopyranonyl, benzophenazinyl, benzoquinolizinyl, dibenzocarbazolyl, dibenzoacridinyl, dibenzophenazinyl, dibenzopyranonyl, dibenzoquinoxalinyl, dibenzothiazepinyl, dibenzisoquinolinyl, tetraazaadamantyl, thiatetraazaadamantyl, oxauracil, oxazinyl, oxazolinyl, oxazolonyl, azaindolyl, azolonyl, thiazolinyl, thiazolonyl, thiazolidinyl, thiazanyl, pyrimidonyl, thiopyrimidonyl, thiamorpholinyl, azalactonyl, naphthindazolyl, naphthindolyl, naphthothiazolyl, naphthoxindolyl, naphthotriazolyl, azabenzimidazolyl, azacycloheptyl, azacyclooctyl, azacyclononyl, azabicyclononyl, dioxindolyl, dioxinyl, dioxenyl, dioxazinyl, thioxanyl, thioxolyl, thiourazolyl, thiotriazolyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl(benzothiofuranyl), phenopyronyl, phenoxazolyl, pyridinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, hydantoinyl, indolyl, indazolyl, benzofuryl, quinolyl, quinazolinyl, quinoxalinyl, carbazolyl, phenoxazinyl, phenothiazinyl, xanthenyl, purinyl, benzothienyl, naphthothienyl, thianthrenyl, pyranyl, pyronyl, benzopyronyl, chromenyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, benzimidazolyl, uridinyl, thymidinyl, cytidinyl, azirinyl, aziridinyl, diazirinyl, diaziridinyl, oxiranyl, oxaziridinyl, dioxiranyl, thiiranyl, azetyl, azetidinyl, diazabicyclooctyl, diazetyl, diaziridinonyl, diaziridinethionyl, benzisothiazolyl, benzocarbazolyl, benzochromonyl, benzisoalloxazinyl, benzocoumarinyl, thiocoumarinyl, phenometoxazinyl, phenoparoxazinyl, phentriazinyl, thiodiazinyl, thiodiazolyl, indoxyl, thioindoxyl, benzodiazinyl (e.g. phtalazinyl), phtalidyl, phtalimidinyl, phtalazonyl, alloxazinyl, isatyl, isopyrazolyl, isopyrazolonyl, urazolyl, urazinyl, uretinyl, uretidinyl, and the like, including all possible isomeric forms thereof. Within the above list, heteroaryl groups including one or more nitrogen atoms in one or more rings are highly preferred.

DETAILED DESCRIPTION OF THE INVENTION

The present invention relates to various groups of novel 1-substituted-2-azabicyclo[3.1.1]heptyl derivatives which have desirable biological properties such as, but not limited to, modulating the activity of a Nicotinic Acetylcholine Receptor (nAChR) e.g. by binding, preferably selectively binding, to one or more subunits of a nAChR subtype, or modulating the activity of another receptor belonging to the Cys-loop superfamily of receptors. Preferably a 1-substituted-2-azabicyclo[3.1.1]heptyl derivative represented by the structural formula (I) or the structural formula (II) or the structural formula (III) is able to modulate, preferably selectively modulate, the activity of one or more of the α7 subtype, the α4β2 subtype, the α3β4 subtype, the α2β4 subtype, the α4β4 subtype, the α3β2 subtype, and the α1β1γδ subtype, of nAChR. Based on this biological activity, and the fact that these compounds are not toxic to human cells, these compounds are useful in the prevention and/or treatment of diseases mediated by a Nicotinic Acetylcholine Receptor such as, but not limited to, pain, Alzheimer's disease, Parkinson's disease, schizophrenia, epilepsy, dementia and nicotine addiction or for the prevention or treatment of other central nervous system disorders such as impaired memory performance, impaired attention and cognitive deficit. They may also be useful in the prevention and/or treatment of a disease mediated by another receptor belonging to the Cys-loop superfamily of receptors.

In the broadest expression, the class of novel biologically active 1-substituted-2-azabicyclo[3.1.1]heptyl derivatives according to the first aspect of this invention may be represented by the structural formula (I) or the structural formula (II) or the structural formula (III), including stereoisomers, solvates and pharmaceutically acceptable salts thereof. This broad class may be sub-divided into several sub-classes wherein each substituent $R_0$ to $R_3$, and/or the divalent group (Aryl) may independently be defined in a more restricted manner, at will and independently from each other. Exemplary but non-limiting embodiments of such sub-classes may be defined as follows:

Aryl is a non-substituted, mono-substituted, di-substituted or tri-substituted phenyl group, n is 0 or 1, Aryl is an optionally substituted nitrogen-containing heteroaryl group such as, but not limited to, pyridin-4-yl, pyridin-3-yl or pyridin-2-yl;

$R_0$ is hydrogen;

$R_0$ is a nitrogen-containing heteroaryl, heteroarylmethyl or heteroarylethyl group such as, but not limited to, pyridin-4-yl, pyridin-3-yl, pyridin-2-yl, pyridin-4-ylmethyl, pyridin-3-ylmethyl, pyridin-2-ylmethyl or pyridinylethyl;

$R_0$ is a phenyl group or a benzyl group wherein said phenyl or the phenyl moiety of said benzyl group may be mono-substituted, di-substituted or tri-substituted with substituents as listed above;

Aryl is an optionally substituted pyridin-3-yl or pyridin-2-yl group, and $R_0$ is benzyl substituted in ortho and/or para positions with one to three methoxy or methyl groups, or $R_0$ is methyl, ethyl, isopropyl, n-propyl, n-butyl or isobutyl, or $R_0$ is pyridin-2-ylmethyl, pyridin-3-ylmethyl, pyridin-4-ylmethyl or pyridinylethyl, or $R_0$ is phenyl substituted in ortho, meta and/or para positions with one to three methoxy or methyl groups;

$R_3$ is halogen, methyl, methoxy, ethoxy, phenyl, trifluoromethyl, amino, heteroaryl or cyano.

The compounds or derivatives represented by any one of the above structural formulae (I), (II) or (III) may be in the form of a pharmaceutically acceptable salt. The latter include any therapeutically active non-toxic addition salt which compounds represented by any one of the structural formulae (I), (II) or (III) are able to form with a salt-forming agent. Such addition salts may conveniently be obtained by treating the said derivative of the invention with an appropriate salt-forming acid or base. For instance, derivatives having basic properties may be converted into the corresponding therapeutically active, non-toxic acid addition salt form by treating the free base form with a suitable amount of an appropriate acid following conventional procedures. Examples of such appropriate salt-forming acids include, for instance, inorganic acids resulting in forming salts such as but not limited to hydrohalides (e.g. hydrochloride and hydrobromide), sulfate, nitrate, phosphate, diphosphate, carbonate, bicarbonate, and the like; and organic monocarboxylic or dicarboxylic acids resulting in forming salts such as, for example, acetate, propanoate, hydroxyacetate, 2-hydroxypropanoate, 2-oxopropanoate, lactate, pyruvate, oxalate, malonate, succinate, maleate, fumarate, malate, tartrate, citrate, methanesulfonate, ethanesulfonate, benzoate, 2-hydroxybenzoate, 4-amino-2-hydroxybenzoate, benzenesulfonate, p-toluenesulfonate, salicylate, p-aminosalicylate, pamoate, bitartrate, camphorsulfonate, edetate, 1,2-ethanedisulfonate, fumarate, glucoheptonate, gluconate, glutamate, hexylresorcinate, hydroxynaphthoate, hydroxyethanesulfonate, mandelate, methylsulfate, pantothenate, stearate, as well as salts derived from ethanedioic, propanedioic, butanedioic, (Z)-2-butenedioic, (E)-2-butenedioic, 2-hydroxybutanedioic, 2,3-dihydroxybutane-dioic, 2-hydroxy-1,2,3-propanetricarboxylic and cyclohexanesulfamic acids and the like. A pharmaceutically acceptable salt formed with a salt-forming acid is illustrated in one of the following examples.

The compounds or derivatives represented by any one of the structural formulae (I), (II) or (III) having acidic properties may be converted in a similar manner into the corresponding therapeutically active, non-toxic base addition salt form. Examples of appropriate salt-forming bases include, for instance, inorganic bases like metallic hydroxides such as but not limited to those of alkali and alkaline-earth metals like calcium, lithium, magnesium, potassium and sodium, or zinc, resulting in the corresponding metal salt; organic bases such as but not limited to ammonia, alkylamines, benzathine, hydrabamine, arginine, lysine, N,N'-dibenzylethylenediamine, chloroprocaine, choline, diethanolamine, ethylenediamine, N-methylglucamine, procaine and the like.

Reaction conditions for treating the compounds or derivatives represented by any one of the structural formulae (I), (II) or (III) of this invention with an appropriate salt-forming acid or base are similar to standard conditions involving the same acid or base but different organic compounds with basic or acidic properties, respectively. Preferably, in view of its use in a pharmaceutical composition or in the manufacture of a medicament for treating specific diseases, the pharmaceutically acceptable salt will be designed, i.e. the salt-forming acid or base will be selected so as to impart greater water-solubility, lower toxicity, greater stability and/or slower dissolution rate to the derivative of this invention.

According to a second aspect, the present invention relates to a method for producing 1-substituted-2-azabicyclo[3.1.1] heptyl derivatives represented by the structural formula (II) wherein $R_1$ is hydrogen and $R_2$ is hydroxyl, comprising reacting a 1-formyl-2-$R_0$-substituted-2-azabicyclo[3.1.1]-heptane, wherein $R_0$ is as defined in the structural formula (II), with an optionally substituted aryl iodide or aryl bromide or aryl chloride represented by the structural formula Y-Aryl-$(R_3)_n$ wherein Y is iodo, chloro or bromo, Aryl, n and $R_3$ are as defined in the structural formula (II).

Representative examples of optionally substituted aryl iodides or aryl bromides or aryl chlorides, wherein Aryl is an aryl group, suitable for this reaction include commercially available products such as, but not limited to:

non-substituted aryl iodides or aryl bromides or aryl chlorides, e.g. 1-iodonaphthalene, 1-chloronaphthalene, 1-bromonaphthalene, 2-bromonaphthalene, bromobenzene, chlorobenzene and iodobenzene;

mono-substituted aryl iodides, aryl bromides or aryl chlorides, e.g. 2-chlorotoluene, 3-chlorotoluene, 4-chlorotoluene, 2-bromotoluene, 3-bromotoluene, 4-bromotoluene, 2-iodotoluene, 3-iodotoluene, 4-iodotoluene, 2-bromocumene, 3-bromocumene, 4-bromocumene, 2-chlorocumene, 3-chlorocumene, 4-chlorocumene, 4-iodocumene, 4-bromophenetole, 3-bromophenetole, 2-bromophenetole, 4-iodophenetole, 4-bromoanisole, 3-bromoanisole, 2-bromoanisole, 3-bromothioanisole, 2-bromothioanisole, 2-iodothioanisole, 3-iodothioanisole, 4-iodothioanisole, 4-n-butoxybromobenzene, 4-tert-butoxybromobenzene, 2-(trifluoromethoxy)-bromobenzene, 3-(trifluoromethoxy)bromobenzene, 4-(trifluoromethoxy)-bromobenzene, 2-(trifluoromethoxy) iodobenzene, 3-(trifluoromethoxy)iodo-benzene, 4-(trifluoromethoxy)iodobenzene and 1-bromo-3-isopropoxy-benzene; and poly-substituted aryl iodides, aryl bromides or aryl chlorides, e.g. 2-bromo-m-xylene, 2-bromo-p-xylene, 3-bromo-o-xylene, 4-bromo-o-xylene, 4-bromo-m-xylene, 5-bromo-m-xylene, 2-chloro-m-xylene, 2-chloro-p-xylene, 4-chloro-o-xylene, 2,3-dichlorotoluene, 2,4-dichlorotoluene, 2,5-dichlorotoluene, 2,6-dichlorotoluene, 3,4-dichlorotoluene, 2,5-dibromotoluene, 3,5-dibromotoluene, 2-bromo-5-chlorotoluene, 3-bromo-4-fluorotoluene, 4-bromo-2-fluorotoluene, 5-bromo-2-fluorotoluene, 2-chloro-4-fluorotoluene, 2-chloro-6-fluorotoluene, 4-chloro-2-fluorotoluene, 2-fluoro-4-iodotoluene, 3,5-dichlorocumene, 2,4-dichlorocumene, 4-amino-2-bromocumene, 2,4-dibromoanisole, 2,6-dibromoanisole, 3,5-dibromoanisole, 4-bromo-3-methylanisole, 4-bromo-2-methyl-anisole, 1-bromo-3,5-dimethoxybenzene, 1-bromo-2,4-dimethoxy-benzene, 1-bromo-2,4,6-trimethoxybenzene, 1-bromo-3,4,5-trimethoxybenzene, 4-bromo-2,6-dimethylanisole, 2,4,6-tribromoanisole, 3-bromo-4-chloroanisole, 4-bromo-3-chloroanisole, 2-bromo-3-fluoroanisole, 2-bromo-4-fluoroanisole, 2-bromo-5-fluoroanisole, 2-bromo-6-fluoroanisole, 3-bromo-4-fluoroanisole, 3-bromo-5-fluoroanisole, 4-bromo-2-fluoroanisole, 4-bromo-3-fluoroanisole, 3,5-dibromo-thioanisole and 1-bromo-3,4-dimethoxybenzene.

Representative examples of optionally substituted aryl iodides, aryl chlorides or aryl bromides, wherein Aryl is a heteroaryl group, suitable for this reaction include commercially available products such as, but not limited to, 3-chloropyridine, 2-chloropyridine, 2,3-dichloropyridine, 3-chloro-5-methylpyridine, 3-chloro-6-methylpyridine, 4-chloro-3-methylpyridine, 2-chloro-4-methylpyridine, 2-chloro-3-amino-4-methylpyridine, 3-chloro-6-phenylpyridine, 5-chloro-2-phenylpyridine, 2-amino-6-chloro-3-phenylpyridine, 2-chloro-3-cyano-6-phenylpyridine, 2-chloro-5-fluoro-3-methylpyridine, 2-bromopyridine, 3-bromopyridine, 4-bromopyridine, 5-bromopyrimidine, 3-bromoquinoline, 4-bromo-3-methylpyrazole, 2-bromothiazole, 2,5-dibromopyridine, 2,6-dibromopyridine, 3,4-dibromopyridine, 3,5-dibromopyridine, 3-bromo-2-chloropyridine, 5-bromo-2-chloropyridine, 2-bromo-5-chloropyridine, 2-chloro-3,5-dibromopyridine, 2-fluoro-3,5-dibromopyridine, 5-bromo-2-fluoropyridine, 3,5-dibromo-2-iodopyridine, 2-bromo-6-methoxypyridine, 5-bromo-2-methoxypyridine, 2-bromo-6-ethoxypyridine, 2-bromo-3-methylpyridine, 3-bromo-4-methylpyridine, 2-bromo-4-methylpyridine, 2-bromo-5-methylpyridine, 6-bromo-2-picoline, 5-bromo-2-picoline, 2-bromo-4-ethylpyridine, 2-bromo-5-cyanopyridine, 5-bromonicotonitrile, 5-bromo-2-(dimethylamino)pyridine, 2-bromo-3-phenylpyridine, 2-bromo-4-phenylpyridine, 2-bromo-5-phenylpyridine, 2-bromo-6-phenylpyridine, 3-bromo-2-phenylpyridine, 3-bromo-4-phenylpyridine, 3-bromo-5-phenylpyridine, 4-bromo-3-phenylpyridine, 5-bromo-2-phenylpyridine, 2-bromo-5-(trifluoromethyl)pyridine, 2-bromo-6-(trifluoromethyl)pyridine, 3-bromo-5-(trifluoromethyl)pyridine, 5-bromo-2-(trifluoromethyl)pyridine, tert-m butyl 5-bromopyridine-2-carboxylate, 2-amino-6-bromopyridine, 2-amino-3-bromopyridine, 2-amino-5-bromopyridine and 3-amino-6-bromopyridine.

According to a specific embodiment of the present invention, the above method for producing 1-substituted-2-azabicyclo[3.1.1]heptyl derivatives represented by the structural formula (II) wherein $R_1$ is hydrogen and $R_2$ is hydroxyl may start from a 1-formyl-2-$R_0$-substituted-2-azabicyclo[3.1.1]-heptane wherein $R_0$ is not hydrogen, i.e. wherein the substituent $R_0$ acts as a nitrogen-protecting group, in which case the method may further comprise a subsequent step of cleaving off the N-protecting $R_0$ substituent to produce a derivative represented by the structural formula (II) wherein $R_0$ is hydrogen.

According to another embodiment, the present invention relates to a method for producing 1-substituted-2-azabicyclo [3.1.1]heptyl derivatives represented by the structural formula (II), wherein $R_1$ in combination with $R_2$ is oxo, comprising reacting a 1-cyano-2-$R_0$-substituted-2-azabicyclo [3.1.1]-heptane with the structural formula

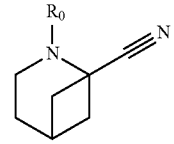

wherein $R_0$ is as defined in the structural formula (II), with an optionally substituted aryl iodide or aryl bromide or aryl chloride represented by the structural formula Y-Aryl-$(R_3)_n$ wherein Y is iodo or bromo or chloro and wherein Aryl, n and $R_3$ are as defined in the structural formula (II). Representative examples of optionally substituted aryl iodides or aryl bromides or aryl chlorides, wherein Aryl is an aryl or a heteroaryl group, and being suitable for this reaction are as defined in details herein-above.

According to a specific embodiment of the present invention, the above method for producing 1-substituted-2-azabicyclo[3.1.1]heptyl derivatives represented by the structural formula (II) wherein $R_1$ in combination with $R_2$ is oxo may start from a 1-cyano-2-$R_0$-substituted-2-azabicyclo[3.1.1] heptane with the structural formula

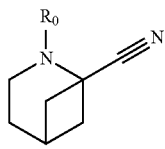

wherein R₀ is not hydrogen, i.e. wherein the substituent R₀ as defined in the structural formula (II) acts as a nitrogen-protecting group, in which case the method may further comprise a subsequent step of cleaving off the N-protecting R₀ substituent to produce a derivative represented by the structural formula (II) wherein R₀ is hydrogen.

According to another aspect, the present invention relates to a method for producing 1-substituted-2-azabicyclo[3.1.1] heptyl derivatives represented by the structural formula (I), comprising submitting a 1-aminomethyl-2-R₀-substituted-2-azabicyclo[3.1.1]heptane, wherein R₀ is as defined in the structural formula (I), to a reaction step with an optionally substituted aryl iodide or aryl bromide or aryl chloride represented by the structural formula Y-Aryl-(R₀)ₙ wherein Y is iodo or bromo or chloro and wherein Aryl, n and R₃ are as defined in the structural formula (I). Preferably, said reaction step is a coupling reaction such as, but not limited to, a Buchwald-Hartwig cross-coupling reaction. This type of reaction is well known to the person skilled in the art and may be performed in the presence of a catalytic amount of a suitable palladium complex catalyst. Suitable examples of palladium complex catalysts for this purpose include complexes wherein palladium is coordinated with monodentate ligands selected from the group consisting of chloro and triarylphosphines (e.g. triphenylphosphine and tri-(o-tolyl) phosphine), and/or bidentate ligands such as, but not limited to:
2,2'-bis-(diphenylphosphino)-1,1'-binaphthyl (BINAP),
1,3-bis-(diphenylphosphino)-propane (DPPP),
1,1'-bis-(diphenylphosphino)-ferrocene (DPPF), and
di-t-butyl-{1-[2-(dicyclohexylphosphanyl)ferrocenyl]ethyl}phosphine (DFEP).

According to a specific embodiment of the present invention, the above method for producing 1-substituted-2-azabicyclo[3.1.1]heptyl derivatives represented by the structural formula (I) may start from a 1-aminomethyl-2-R₀-substituted-2-azabicyclo[3.1.1]heptane with the structural formula (III)

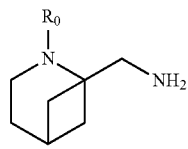

wherein R₀ is not hydrogen, i.e. wherein the substituent R₀ acts as a nitrogen-protecting group, in which case the method may further comprise a terminal step of cleaving off the N-protecting R₀ substituent to produce a derivative represented by the structural formula (I) wherein R₀ is hydrogen.

For performing any one of the above production methods, it may first be necessary to produce 1-formyl-2-R₀-substituted-2-azabicyclo[3.1.1]-heptanes or 1-cyano-2-R₀-substituted-2-azabicyclo[3.1.1]heptanes, wherein R₀ is hydrogen or a nitrogen-protecting group selected from the group consisting of phenyl, benzyl, heteroaryl, heteroarylmethyl, heteroarylethyl, phenylethyl, naphthylmethyl, naphthylethyl, butoxycarbonyl, $C_{3-4}$ alkenyl and $C_{1-8}$ alkyl, and wherein said phenyl or heteroaryl or the phenyl moiety of said benzyl is optionally substituted with one to three substituents independently selected from the group consisting of halogen, $C_{1-8}$ alkyl, $C_{1-8}$ alkoxy, trifluoromethyl, trifluoromethoxy, dimethylaminoethoxy, dimethylaminopropoxy, morpholinoethoxy, phenoxy, phenoxy-methyl, heteroaryl and heteroarylmethyl, and wherein each of said 1 to 3 substituents may independently be located at the ortho-, meta- or para-position of said phenyl moiety.

A non-limiting method for producing a 1-cyano-2-R₀-substituted-2-azabicyclo[3.1.1]heptane with the structural formula

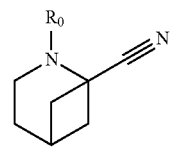

comprises reacting 3-(2-chloroethyl)cyclobutanone with a molar equivalent or a molar excess of the relevant primary amine R₀NH₂ (wherein R₀ is selected from the group consisting of phenyl, benzyl, heteroaryl, heteroarylmethyl, heteroarylethyl, phenylethyl, naphthylmethyl, naphthylethyl, butoxycarbonyl, $C_{3-4}$ alkenyl and $C_{1-8}$ alkyl, and wherein said phenyl, benzyl or heteroaryl is optionally substituted with 1 to 3 substituents independently selected from the group consisting of halogen, $C_{1-4}$ alkyl, $C_{1-4}$ alkoxy, trifluoromethyl, trifluoromethoxy, dimethylaminoethoxy, dimethylaminopropoxy, morpholinoethoxy, phenoxy, phenoxymethyl, heteroaryl and heteroarylmethyl) and at least two molar equivalents of acetone cyanohydrin, and optionally in the further presence of at least one molar equivalent of a tertiary amine such as, but not limited to, triethylamine.

The primary amine R₀NH₂ may thus be an aniline, a benzylamine or a halogenated aniline. Suitable benzylamines include, but are not limited to, 2-chlorobenzylamine, 4-chlorobenzylamine, 2,4-dichlorobenzylamine, 3,4-dichlorobenzylamine, 4-methoxybenzylamine, 4-methylbenzylamine, piperonylamine, 3,4-dimethoxybenzylamine, 3-methylbenzylamine, 3-fluorobenzylamine, 2-methylbenzylamine, 2-methoxybenzylamine, 3-methoxybenzylamine, 2-fluorobenzylamine, 4-fluorobenzylamine, 3,4-dihydroxybenzylamine, 3-chlorobenzylamine, 4-(trifluoromethoxy)benzylamine, 2,6-difluorobenzylamine, 3,5-bis(trifluoromethyl)benzylamine, 2,4-difluorobenzylamine, 2,5-difluoro benzylamine, 3,4-difluorobenzylamine, 2-(trifluoromethyl)benzylamine, 3-(trifluoromethyl)benzylamine, 2-bromobenzylamine, 4-bromobenzylamine, 2-chloro-6-fluorobenzylamine, 2,5-dimethylbenzylamine, 3,4,5-trimethoxybenzylamine, 2,4,6-trimethylbenzylamine, 2,4-dimethylbenzylamine, 2,3-dichlorobenzylamine, 1-naphthalenemethylamine, 3-Iodobenzylamine, 2-hydroxybenzylamine, 3-bromo benzylamine, 2,6-dichlorobenzylamine, 3,4-dihydro-2H-1,5-benzodioxepin-6-ylmethylamine, 2,3-dihydro-1,4-benzodioxin-6-ylmethylamine, 2,3-dihydro-1,4-benzodioxin-5-ylmethylamine, 1-benzofuran-5-ylmethylamine, 4-(2-thienyl)benzylamine, 3,4-dihydro-2H-1,5-benzodioxepin-7-ylmethylamine, 4-morpholino benzylamine, 4-(1H-pyrazol-1-yl)benzylamine, 4-(4-methylpiperazino)benzylamine, 2-piperidinobenzylamine, 3-(1H-Pyrrol-1-yl)benzylamine, 2-Morpholinobenzylamine, 4-(1H-pyrrol-1-yl)benzylamine, 2-chloro-6-phenoxybenzylamine, 2-(methylthio)benzylamine, 2-(trifluoromethoxy)

benzylamine, 2,3-dimethylbenzylamine, 4-(trifluoromethyl)benzylamine, 3,5-dichlorobenzylamine, 2-(Aminomethyl)-3-fluoroaniline, 3-chloro-4-fluorobenzylamine, 2,5-dimethoxybenzylamine, 2,5-dichloro benzylamine, 2,6-dimethoxybenzylamine, 2,4-dichloro-6-methylbenzylamine, 3-chloro-4-methylbenzylamine, 4-fluoro-3-(trifluoromethyl)benzylamine, 4-fluoro-2-(trifluoromethyl)benzylamine, 3-piperidin-1-ylmethyl benzylamine, 1-benzothiophen-5-ylmethylamine, 4-(Morpholinomethyl)benzylamine, (3-((4-methylpiperidino)methyl)phenyl)methanamine, (4-Piperidinophenyl)methylamine, (3-piperidinophenyl)methylamine, 1-[2-(4-methylpiperazin-1-yl)phenyl]methanamine, (1,4-dimethyl-1,2,3,4-tetrahydroquinoxalin-6-yl)methylamine, 3-(trifluoromethoxy)benzylamine, 4-bromo-2-fluorobenzylamine, 2-(1H-pyrazol-1-yl)benzylamine, tert-butyl 4-(2-(aminomethyl)phenyl)piperazine-1-carboxylate, (3-morpholinophenyl)methylamine, tert-butyl N-[4-(aminomethyl)phenyl]carbamate, [2-(1H-Pyrrol-1-yl)phenyl]methylamine, 1-[3-(4-Methylpiperazin-1-yl)phenyl]methanamine, [4-(1-pyrrolidinyl)phenyl]-methanamine, (3-pyrrolidin-1-ylphenyl)methylamine, [4-(2-morpholinoethoxy)phenyl]methylamine, [2-(2-morpholinoethoxy)phenyl]methylamine, [3-(2-morpholinoethoxy)phenyl]methylamine, [3-(morpholinomethyl)phenyl]methylamine, [4-(piperidinomethyl)phenyl]methylamine, {4-[(4-Methylpiperazin-1-yl)methyl]phenyl}methylamine, [4-(2-furyl)phenyl]methylamine, tert-Butyl 4-[4-(aminomethyl)phenyl]tetrahydro-1(2H)-pyrazinecarboxylate, (2,2-dimethyl-2,3-dihydro-1-benzofuran-7-yl)methylamine, [3-(1 h-1,2,4-triazol-1-yl)phenyl]methylamine, (4-thien-3-ylphenyl)methylamine, 1-[2-(morpholin-4-ylmethyl)phenyl]methanamine, {2-[(4-methylpiperazin-1-yl)methyl]phenyl}methylamine, [3-(2-furyl)phenyl]methylamine, (3-thien-2-ylphenyl)methylamine, [2-(2-furyl)phenyl]methylamine, 4-(Pyrrolidin-1-ylmethyl)benzylamine, 4-[(4-methylperhydro-1,4-diazepin-1-yl)methyl]benzylamine, 4-[2-(dimethylamino) ethoxy]benzylamine, (2-pyrrolidin-1-ylphenyl)methylamine, [3-(1-Pyrrolidinylmethyl)phenyl]methanamine, (3-thien-3-ylphenyl)methylamine, 2-[2-(dimethylamino)ethoxy]benzylamine, 2-(phenoxymethyl)benzylamine, (1-methyl-1h-indol-4-yl)methylamine, 4-(4-methylperhydro-1,4-diazepin-1-yl)benzylamine, (1-methyl-1H-indol-6-yl)methylamine, [3-(1,3-thiazol-2-yl)phenyl]methylamine, 3-(1H-pyrazol-1-ylmethyl)benzylamine, (1-methyl-1H-indol-5-yl)methylamine, 3-(phenoxymethyl)benzylamine, 2-morpholino-5-(trifluoromethyl)benzylamine, [4-(1,3-thiazol-2-yl)phenyl]methylamine, 3-(1-methyl-1H-pyrazol-3-yl)benzylamine, 2-(4-methylperhydro-1,4-diazepin-1-yl)benzylamine, 4-[3-(dimethylamino)propoxy]benzylamine, 3-(2-Methyl-1H-imidazol-1-yl)benzylamine, 4-(2-methyl-1H-imidazol-1-yl)benzylamine, 2-(2-methyl-1H-imidazol-1-yl)benzylamine, [4-(tetrahydropyran-4-yloxy)phenyl]methylamine, 3-[3-(dimethylamino)propoxy]-benzylamine, 2-[3-(dimethylamino)propoxy]benzyl-amine, 3-pyrimidin-2-ylbenzylamine, 4-(1-methyl-1H-pyrazol-3-yl)benzylamine, 3-(1-methyl-1H-pyrazol-5-yl)benzylamine and 1-(1-benzothien-7-yl)methanamine.

Suitable anilines include, but are not limited to, aniline and:

$C_{1-4}$ alkoxy-substituted and $C_{1-4}$ alkylthio-substituted anilines including, but not limited to, 2-methoxyaniline, 3-methoxyaniline, 4-methoxyaniline, 2-ethoxyaniline, 3-ethoxyaniline, 4-ethoxyaniline, 4-bromo-3-ethoxyaniline hydrochloride, 2-propoxyaniline, 3-propoxyaniline, 4-propoxyaniline, 3-isopropoxyaniline, 4-isopropoxyaniline, 2,5-diethoxyaniline, 3,4-diethoxyaniline, 4-n-butoxyaniline, 3-n-butoxyaniline, 2-n-butoxyaniline, 4-iso-butoxyaniline, 3-isobutoxyaniline, 2-isobutoxyaniline, 2-methyl-4-methoxyaniline, 2-(methylthio)aniline, 3-(methylthio)aniline, 4-(methylthio)aniline, 2-(trifluoromethoxy)aniline, 3-(trifluoromethoxy)aniline, 4-(trifluoromethoxy)aniline, 5-chloro-2-(methylthio)aniline, 2-bromo-4-methoxyaniline, 2-bromo-5-methoxyaniline, 3-bromo-4-methoxyaniline, 4-bromo-3-methoxyaniline, 5-bromo-2-methoxyaniline, 2-iodo-5-methoxyaniline, 3-iodo-4-methoxyaniline, 5-iodo-2-methoxyaniline, 2-chloro-5-methoxyaniline, 3-chloro-2-methoxyaniline, 3-chloro-4-methoxyaniline, 4-chloro-3-methoxyaniline, 5-chloro-2-methoxyaniline, 2-fluoro-4-methoxyaniline, 2-fluoro-6-methoxyaniline, 3-fluoro-2-methoxyaniline, 3-fluoro-4-methoxyaniline, 3-fluoro-5-methoxyaniline, 4-fluoro-3-methoxyaniline, 5-fluoro-2-methoxyaniline, 2-(difluoromethoxy)aniline, 3-(difluoromethoxy)aniline, 4-(difluoromethoxy)aniline and 2,4-dichloro-5-methoxyaniline;

halo-substituted anilines including, but not limited to, 2-fluoroaniline, 3-fluoroaniline, 4-fluoroaniline, 2,3-difluoroaniline, 2,4-difluoroaniline, 2,5-difluoroaniline, 2,6-difluoroaniline, 3,4-difluoroaniline, 2,3,4-trifluoroaniline, 2,3,5-trifluoroaniline, 2,3,6-trifluoroaniline, 2,4,6-trifluoroaniline, 2,4,5-trifluoroaniline, 3,4,5-trifluoroaniline, 3-chloro-2-fluoroaniline, 4-chloro-2-fluoroaniline, 5-chloro-2-fluoroaniline, 2-chloro-3-fluoroaniline, 2-chloro-4-fluoroaniline, 2-chloro-6-fluoroaniline, 3-chloro-5-fluoroaniline, 2-bromo-3-fluoroaniline, 2-bromo-4-fluoroaniline, 2-bromo-5-fluoroaniline, 2-bromo-6-fluoroaniline, 4-bromo-2-fluoroaniline, 4-bromo-3-fluoroaniline, 5-bromo-2-fluoroaniline;

$C_{1-12}$ alkyl-substituted anilines including, but not limited to, 4-methylaniline, 3-methylaniline, 2-methylaniline, 2,3-dimethylaniline, 2,4-dimethylaniline, 2,5-dimethylaniline, 2,6-dimethylaniline, 3,4-dimethylaniline, 3,5-dimethylaniline, 2,4,6-trimethylaniline, 3,4,5-trimethylaniline, 2,4,5-trimethylaniline, 2,4,6-trimethylaniline, 4-ethylaniline, 3-ethylaniline, 2-ethylaniline, 2-n-propylaniline, 4-n-propylaniline, 2-isopropylaniline, 3-isopropylaniline, 4-isopropylaniline, 2,6-diisopropylaniline, 2-n-butylaniline, 4-n-butylaniline, 2-sec-butylaniline, 4-sec-butylaniline, 2-tert-butylaniline, 3-tert-butylaniline, 4-tert-butylaniline, 3,5-di-tert-butylaniline, 4-n-pentylaniline, 4-n-hexylaniline, 4-n-heptylaniline, 4-n-octylaniline, 4-nonylaniline, 4-n-decylaniline and 4-n-dodecylaniline;

$C_{3-8}$ cycloalkyl-substituted anilines including, but not limited to, 4-cyclohexylaniline;

2-nitroaniline, 3-nitroaniline, 4-nitroaniline, 2-trifluoromethylaniline, 3-trifluoromethylaniline, 4-trifluoromethylaniline, and the like.

Production of 3-(2-chloroethyl)cyclobutanone itself is illustrated in one of the following examples.

Reducing, according to methods well known in the art (e.g. lithium aluminum hydride at low temperatures) the nitrile group of a 1-cyano-2-$R_0$-substituted-2-azabicyclo[3.1.1]heptane with the structural formula

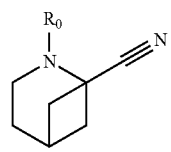

affords a compound of the invention represented by the structural formula (III) which is of particular interest when $R_0$ is heteroarylmethyl or heteroarylethyl and said heteroaryl is a nitrogen-containing group. This particular interest stems from the fact that the compound shows desirable biological activity without a need for further derivatisation of the aminomethyl side group and without a need for a final deprotection step of the nitrogen atom of the azabicyclo[3.1.1]heptyl ring.

A non-limiting method for producing a 1-formyl-2-$R_0$-substituted-2-azabicyclo[3.1.1]heptane is by the partial reduction of a 1-cyano-2-$R_0$-substituted-2-azabicyclo[3.1.1]heptane according to reducing methods well known in the art followed by acidic hydrolysis.

In all of the above methods when $R_0$ is originally present as a nitrogen-protecting group to be later converted into hydrogen by a suitable deprotection method in the usually final step of the production method, i.e. when $R_0$ is not a nitrogen-containing heteroarylmethyl or heteroarylethyl group providing biological activity by itself, the proper selection of $R_0$ will take into account both:
- the capacity to allow for ring closure to form the bicyclic skeleton with a reasonable kinetics (such capacity being linked to parameters such as electron-withdrawing capacity and steric hindrance), and
- the easiness of removal in the usually final deprotection step.

Deprotection techniques for nitrogen-protecting groups, in particular for benzyl, mono-substituted benzyl, di-substituted benzyl and tri-substituted benzyl groups, are well known in the art and are detailed for instance by Kocienski, *Protecting groups*, $3^{rd}$ edition (2004), Georg Thieme Verlag, Stuttgart and by Greene et al in *Greene's protective groups in organic synthesis*, $4^{th}$ edition (2007), Wiley-Interscience, New Jersey, the content of which is incorporated herein by reference.

In order to suitably use a compound disclosed in this invention or a pharmaceutically acceptable salt, or solvate thereof, for the therapeutic treatment (including prophylactic treatment) of mammals including humans, it is usually formulated in accordance with standard pharmaceutical practice as a pharmaceutical composition including one or more appropriate pharmaceutically acceptable excipients.

The term "pharmaceutically acceptable carrier or excipient" as used herein in relation to pharmaceutical compositions and combined preparations means any material or substance with which the active principle, i.e. the compound or derivative represented by any one of the structural formulae (I), (II) or (III), may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders.

Suitable pharmaceutical carriers for use in the said pharmaceutical compositions and their formulation are well known to those skilled in the art. There is no particular restriction to their selection within the present invention although, due to the usually low or very low water-solubility of the derivatives of this invention, special attention will be paid to the selection of suitable carrier combinations that can assist in properly formulating them in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals.

The pharmaceutical compositions of the present invention may be prepared in any known manner, for instance by homogeneously mixing, dissolving, spray-drying, coating and/or grinding the active ingredients, in a one-step or a multi-step procedure, with the selected carrier material and, where appropriate, the other additives such as surface-active agents. may also be prepared by micronisation, for instance in view to obtain them in the form of microspheres usually having a diameter of about 1 to 10 µm, namely for the manufacture of microcapsules for controlled or sustained release of the biologically active ingredient(s).

Suitable surface-active agents to be used in the pharmaceutical compositions of the present invention are non-ionic, cationic and/or anionic surfactants having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable from coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl group having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphthalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidylcholine, dipalmitoylphoshatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with polypropylene glycol, ethylenediamino polypropylene glycol containing 1 to 10 carbon atoms in the alkyl chain, which adducts contain 20 to 250 ethylene glycol ether groups and/or 10 to 100 propylene glycol ether groups. Such compounds usually contain from 1 to 5 ethylene glycol units per propylene glycol unit. Representative examples of non-ionic surfactants are nonylphenol-polyethoxyethanol, castor oil polyglycolic ethers, polypropylene/polyethylene oxide adducts, tributylphenoxy-polyethoxyethanol, polyethylene-glycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having four hydrocarbon groups optionally substituted with halo, phenyl, substituted phenyl or hydroxy; for instance quaternary ammonium salts containing as N-substituent at least one $C_8$-$C_{22}$ alkyl group (e.g. cetyl, lauryl, palmityl, myristyl, oleyl and the like) and, as further substituents, unsubstituted or halogenated lower alkyl, benzyl and/or hydroxy-$C_{1-4}$ alkyl groups.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", $2^{nd}$ ed. (Hanser Verlag, Vienna, 1981) and "Encyclopaedia of Surfactants (Chemical Publishing Co., New York, 1981).

Structure-forming, thickening or gel-forming agents may be included into the pharmaceutical compositions and combined preparations of the invention. Such suitable agents are in particular highly dispersed silicic acid, such as the product commercially available under the trade name Aerosil; bentonites; tetra-alkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

Gelling agents which may be included into the pharmaceutical compositions and combined preparations of the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof. Gelatin and modified celluloses represent a preferred class of gelling agents.

Other optional excipients which may be included in the pharmaceutical compositions and combined preparations of the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylenediamine tetra-acetic acid; flavoring agents such as natural vanillin; buffers such as citric acid and acetic acid; extenders or bulking agents such as silicates, diatomaceous earth, magnesium oxide or aluminum oxide; densification agents such as magnesium salts; and mixtures thereof.

Additional ingredients may be included in order to control the duration of action of the biologically-active ingredient in the compositions of the present invention. Control release compositions may thus be achieved by selecting appropriate polymer carriers such as for example polyesters, polyamino-acids, polyvinyl-pyrrolidone, ethylenevinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition or combined preparation of the invention may also require protective coatings.

Pharmaceutical forms suitable for injectable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol, complexing agents such as cyclodextrins and the like, and mixtures thereof.

In another aspect the present invention relates to a method of preventing or treating a disease, comprising the administration of a therapeutically effective amount of a derivative as defined in any specific embodiment above, in particular being represented by any one of the structural formulae (I), (II) and (III), including any particular embodiments thereof, to a patient in need thereof, optionally in combination with one or more pharmaceutically acceptable carriers. In particular the 1-substituted-2-azabicyclo[3.1.1]heptyl derivatives described herein are useful in modulating cholinergic function or nicotinic acetylcholine receptor activity. Numerous diseases, especially those mediated by a Nicotinic Acetylcholine Receptor (or a subtype thereof, in particular the $\alpha 7$ subtype, the $\alpha 4\beta 2$ subtype, the $\alpha 3\beta 4$ subtype, the $\alpha 2\beta 4$ subtype, the $\alpha 4\beta 4$ subtype, the $\alpha 3\beta 2$ subtype, and the $\alpha 1\beta 1\gamma\delta$ subtype of nAChR) or another receptor belonging to the Cys-loop superfamily of receptors, may be treated by means of a 1-substituted-2-azabicyclo[3.1.1]heptyl derivative such as disclosed herein.

Non-limiting examples of such diseases include various forms of the inflammatory bowel disease (including, but not limited to, ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amylotropic lateral sclerosis, cognitive dysfunction, hypertension, bulimia, anorexia, obesity, cardiac arrythmia, gastric acid hypersecretion, ulcers, pheochromocytoma, progressive supramuscular palsy, chemical dependencies and addictions (e.g. dependencies on nicotine (and/or tobacco products), alcohol, benzodiazepines, barbiturates, opioids or cocaine), headache, stroke, traumatic brain injury, obsessive-compulsive disorders, psychosis, Huntington's Chorea, tardive dyskinesia, hyperkinesia, dyslexia, schizophrenia, multi-infarct dementia, age-related cognitive decline, epilepsy, senile dementia of the Alzheimer's type, Parkinson's disease, attention deficit hyperactivity disorder (ADHD) and Tourette's Syndrome.

Compounds of this invention being represented by any one of the structural formulae (I), (II) and (III) may also be used in combination with:

one or more antidepressant drugs such as, but not limited to, tricyclic antidepressants and serotonin re-uptake inhibiting antidepressants, in order to treat both the cognitive decline and depression associated with Alzheimer's Disease, Parkinson's Disease, or traumatic brain injury;

one or more muscarinic agonists in order to stimulate both central muscarinic and nicotinic receptors for the treatment, for example, of cognitive dysfunction, age-related cognitive decline, Alzheimer's Disease, Parkinson's Disease, stroke or Huntington's Chorea;

one or more neurotrophic factors such as NGF in order to maximize cholinergic enhancement for the treatment, for example, of cognitive dysfunction, age related cognitive decline, Alzheimer's Disease, Parkinson's Disease, stroke or Huntington's Chorea;

one or more agents that slow or arrest Alzheimer's Disease such as, but not limited to, cognition enhancers, amyloid aggregation inhibitors, secretase inhibitors, tau kinase inhibitors, neuronal anti-inflammatory agents and estrogen-like therapeutic agents.

The precise biological activity profile of the 1-substituted-2-azabicyclo[3.1.1]heptyl derivatives disclosed in this invention may be determined by using one or more of the assays described in the review article published by Dunlop et al in *Biochemical Pharmacology* (2007) 74:1172-1181 such as, but not limited to:

assays using a cell system wherein the alfa7-subunit of the Nicotinic Acetylcholine Receptor complex is heterologously expressed, e.g. *Xenopus* (frog) oocytes or GH4C1 (mammalian) cells;

a radioactive displacement binding assay, e.g. using 3H labelled epibatidine and the *Xenopus* oocyte expression system;

a functional cell based binding assay (e.g. the $Ca^{2+}$ flux FLIPR assay) wherein (*Xenopus*/GH4C1) a ligand gated ion channel consisting out of five α7 subunits (pentamer) is formed in a cell system; in such assays, binding of a ligand causes ion fluxes which can be measured using fluorescent labelled ions e.g. through the Fluorescent Imaging Plate Reading (FLIPR) technique; this approach provides, next to the fact that a ligand binds to a receptor, also information with respect to the receptor activity;

electrophysiological recording such as the Two Electrode Voltage Clamp technique (TEVC), e.g. used with the radioligand binding assay and the *Xenopus* cell system, or the Patch Clamp technique, e.g. in combination with the "U-tube bathing technique", or any one of the more specific binding assays disclosed in the following examples, or any one of the assays and methodologies disclosed by Broad et al in *J. Pharmacol. Exper. Therap.* (2006) 318: 1108-1117.

In order to suitably use the 1-substituted-2-azabicyclo [3.1.1]heptyl derivatives disclosed in this invention, being represented by any one of the structural formulae (I), (II) and (III), for therapeutic or prophylactic purpose, such compounds are preferably administered in a therapeutically effective amount (e.g. an analgesic dose when the pathologic condition to be treated is pain), e.g. a daily dose in the range of, for example, 0.1 mg to 75 mg per kg body weight is received, said daily dose being given if required in divided sub-doses, also depending upon the patient to be treated and the severity of the disease to be cured. In general, lower doses will be administered when a parenteral route is employed. Thus, for example, for intravenous administration, a dose in the range of, for example, 0.5 mg to 30 mg per kg body weight will preferably be used. Similarly, for administration by inhalation, a dose in the range of, for example, 0.5 mg to 25 mg per kg body weight will preferably be used. According to a particular embodiment, the envisaged administration route for the compounds of the invention is oral administration, particularly in tablet form. Typically, unit dosage forms will contain about 1 mg to 500 mg of a compound of this invention.

The following examples are merely illustrative of the production and characterization of some 1-substituted-2-azabicyclo[3.1.1]heptyl derivatives of the present invention, but any type of compounds represented by the structural formulae (I), (II) or (III) may be produced in accordance with the synthetic procedures described herein.

Purification and characterization of the compounds was performed by means of the following techniques and devices:

High resolution $^{1}$H-NMR (300 MHz) and $^{13}$C-NMR (75 MHz) spectra were run on a Jeol JNM-EX 300 NMR device. Peak assignments were obtained with the aid of Distortionless Enhancement by Polarization Transfer (DEPT), Heteronuclear Single Quantum Coherence (HSQC), Heteronuclear Multiple Bond Coherence (HMBC) and Homonuclear Correlation Spectroscopy (COSY) spectra. The compounds were diluted in deuterated solvents as indicated for each compound;

Low resolution mass spectra were recorded on an Agilent 1100 Series VS (ES, 4000V) mass spectrometer;

IR-spectra were recorded on a Perkin-Elmer Spectrum BX FT-IR spectrometer. All compounds were analyzed in neat form with an ATR (Attenuated Total Reflectance) accessory;

Purification of reaction mixtures was performed by column chromatography using a glass column with silica gel (commercially available from Acros, particle size 0.035-0.070 mm, pore diameter 6 nm);

Melting points of crystalline compounds were measured with a Büchi 540 apparatus.

Example 1

Synthesis of 3-(2-chloroethyl)cyclobutanone

Synthesis proceeds as shown in scheme 1. Homoallyl chloride was formed from the commercially available homoallyl alcohol, using thionylchloride and pyridine.[i] In a next step, a [2+2]cycloaddition of in situ formed dichloroketene using activated zinc and homoallylchloride leads to the cyclobutanone 3. To obtain the desired precursor, 3-(2-chloroethyl) cyclobutanone 4, the cycloaddition product 3 was treated with zinc in acetic acid, reductively removing the two geminal chlorine atoms without the formation of any side product.

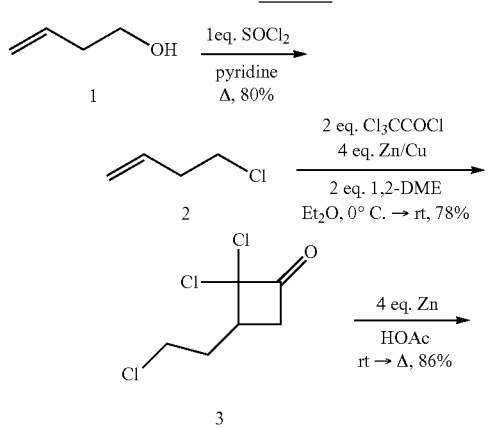

Scheme 1

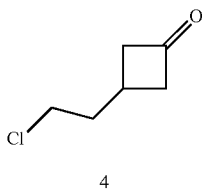

Details of these three steps are as follows:

Synthesis of compound 3
(2,2-dichloro-3-(2-chloroethyl)cyclobutanone)

In a two-necked flask of 500 mL was 50 g (760 mmole) of zinc vigorously stirred in 200 mL of distilled water, while nitrogen gas was bubbled through. After this period, 3.75 g (23 mmole) of copper(II)sulphate was added at once, and the resulting suspension was stirred for another 45 minutes while the bubbling with nitrogen gas continued. The resulting zinc-copper couple was filtered under a nitrogen atmosphere and washed with respectively 500 mL of degassed water and 500 mL of degassed acetone. The black powder was transferred to a flask and dried at the high vacuum (0.6 mm Hg) for 2 hours. After this drying procedure, the flask was flushed with nitrogen gas and the zinc-copper couple was stored at room temperature in a sealed flask. In an oven-dried two-necked flask of 500 mL, a solution of homoallyl chloride (15 g, 166 mmol) and a zinc-copper couple (43.32 g, 663 mmole) in 250 mL of dry ether was cooled to 0° C. under a inert $N_2$-atmosphere. A solution of trichloroacetylchloride (60.24 g, 331 mmole) and 1,2-dimethoxyethane (29.86 g, 331 mmole) in 150 mL of dry ether was added dropwise, after which the reaction mixture was stirred overnight at room temperature. The solution was filtered over celite and washed with ether. This filtrate was extracted with 2×100 mL of water, 4×100 mL of $NaHCO_3$ and 2×100 mL of brine. The clear orange, organic layer was dried over $MgSO_4$ and the solvent was removed under reduced pressure, leading to 26.24 g of 3-(2-chloroethyl)-2,2-dichlorocyclobutanone (yield=78%).

Synthesis of compound 4
(3-(2-chloroethyl)cyclobutanone)

A solution of 3-(2-chloroethyl)-2,2-dichlorocyclobutanone (28.23 g, 140 mmole) in 100 mL of acetic acid was vigorously stirred, while slowly adding 2 equivalents of zinc (18.32 g, 280 mmole). During the addition, the solution started to reflux, making cooling inevitable. Two extra equivalents of zinc (18.32 g, 280 mmol) were added to the reaction mixture, after which it was refluxed overnight. After cooling, the mixture was filtered over celite and washed with dichloromethane. The filtrate was poured into a separation funnel and neutralised with a saturated $NaHCO_3$ solution. The organic phase was dried with $MgSO_4$, filtered and the solvent was removed in vacuo. 3-(2-chloroethyl)cyclobutanone was obtained as a bright yellow oil in 86% yield.

Example 2

Synthesis of 2-$R_0$-substituted-2-azabicyclo[3.1.1] heptane-1-carbonitriles

The key step involves the one-pot procedure of imine formation, addition of cyanide to the imine function, followed by an intramolecular nucleophilic substitution, as shown in scheme 2. This was performed by treating the 3-(2-chloroethyl)cyclobutanone 4 with a molar equivalent of the relevant primary amine $R_0NH_2$ and two molar equivalents of acetone cyanohyrin, and in the further presence of two molar equivalents of triethylamine in a closed vessel in methanol for two to three days. The conversion of the cyclobutanone to the 2-azabicyclo[3.1.1]heptane-1-carbonitrile was complete. Although the purification of the resulting compound by flash chromatography (or acid base extraction) lowers the reaction yield, it however proved to be twice higher than by the method of Radchenko et al (cited supra) as far as the benzyl derivative (compound 5a below) was concerned. Fourteen illustrative 2-substituted-2-azabicylo[3.1.1]heptane-1-carbonitriles were obtained in this way.

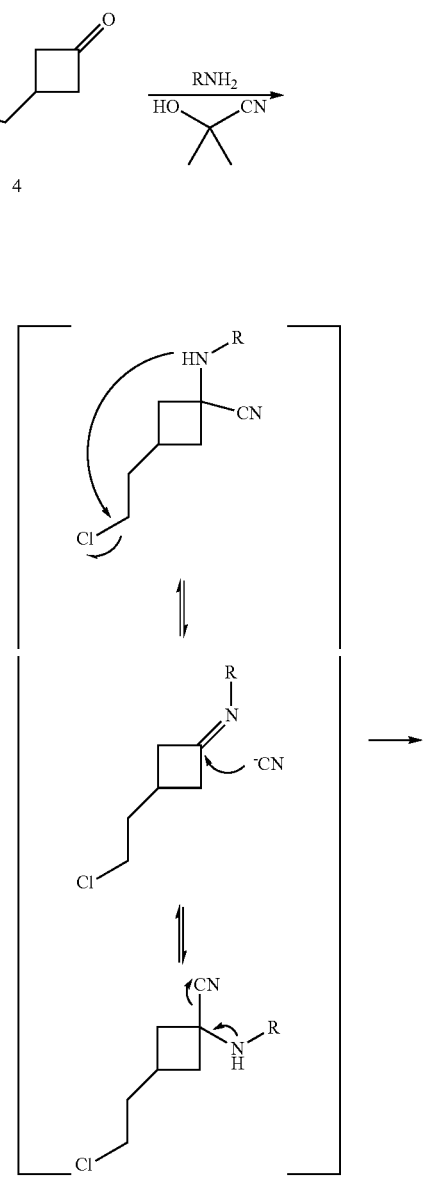

Scheme 2

-continued

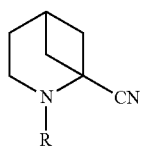

5

5a: R = benzyl (79%)
5b: R = p-methoxy benzyl (85%)
5c: R = iso-propyl (59%)
5d: R = n-propyl (73%)
5e: R = iso-butyl (78%)
5f: R = n-butyl (79%)
5g: R = p-methyl benzyl (70%)
5h: R = pyridin-2-ylmethyl (70%)
5i: R = pyridin-3-ylmethyl (55%)
5j: R = pyridin-4-ylmethyl (65%)
5k: R = 2,4-dimethoxy benzyl (80%)
5l: R = p-methoxy phenyl (72%)
5m: R = ethyl (92%)
5n: R = methyl (75%)

Details of these syntheses are as follows:

Synthesis of compounds 5a-5n (2-$R_0$-2-azabicyclo[3.1.1]heptane-1-carbonitriles)

In a dry, pressure resistant vessel of 20 ml, 1.00 g (7.5 mmole) of 3-(2-chloroethyl)cyclobutanone 4, 7.5 mmole of a primary amine, 1.28 g (15 mmole) acetone cyanohydrine and 1.52 g (15 mmole) triethylamine were dissolved in 16 ml dry methanol. The vessel was closed and heated to 110° C. for 2 to 3 days. When using ethylamine (pure) or methylamine (2M in MeOH), the vessel was heated for 4 days, using 15 mmole of the volatile amine. Isolation of the desired end product could be performed by two means. The first method made use of column chromatography. After washing of the reaction mixture with a saturated NaHCO$_3$ solution, 3 g of silica were added to the organic phase (dichloromethane), followed by removal of the solvent under vacuum. The end product was then recovered using column chromatography, which has the shortcoming of being time-consuming and leading to a lower yield. The second purification strategy was more convenient and consisted of an acid-base extraction. After removal of the solvent under reduced pressure, 10 mL of a 2 N HCl solution was added. The solution was extracted with diethyl ether (3×20 mL) to remove the excess of acetone cyanohydrine. A concentrated K$_2$CO$_3$ solution was added to the water layer until basic, followed by an extraction of the water layer with dichloromethane (3×30 mL). The combined organic layers (dichloromethane) were dried with MgSO$_4$. After filtration of the solids and removal of the volatiles, the pure end product was obtained in moderate to good yields, depending on the $R_0$-group. The 2-$R_0$-azabicyclo[3.1.1]heptane-1-carbonitriles were characterised by proton ($^1$H-NMR) and carbon ($^{13}$C-NMR) nuclear magnetic resonance, mass spectrum (MS$^{ES}$) and infrared (IR) spectrophotometry as follows:

Compound 5a (yield 79%) was obtained from benzylamine.
Compound 5b (yield 85%) was obtained from 4-methoxybenzylamine:
$^1$H-NMR (300 MHz, CDCl$_3$) (ppm): 1.91 (2H, td, J=6.6 Hz, J=3.3 Hz, C$\underline{H}_2$); 2.24 (2H, dd (+2 symm. side lines), J=7.2 Hz, J=2.2 Hz (J=10.3 Hz from centre of signal), 2×C$_q$C$\underline{H}_a$H$_b$); 2.41 (2H, td (+2 symm. side lines), J=7.2 Hz, J=2.2 Hz (J=13.2 Hz from centre of signal), 2×C$_q$CH$_a$$\underline{H}_b$); 2.49 (1H, septet, J=3.3 Hz, C$\underline{H}$); 2.85 (2H, t, J=6.6 Hz, NC$\underline{H}_2$); 3.79 (5H, s, NC$\underline{H}_2$Ph, OC$\underline{H}_3$ (Ph)); 6.86 (2H, d, J=8.8 Hz, 2×C$\underline{H}$ (Ph)); and 7.29 (2H, d, J=8.8 Hz, 2×C$\underline{H}$ (Ph));

$^{13}$C-NMR (75 MHz, CDCl$_3$) (ppm): 27.68 (C$\underline{H}_2$); 31.25 (C$\underline{H}$); 37.21 (2×C$_q$C$\underline{H}_2$); 42.49 (NC$\underline{H}_2$); 55.27 (OC$\underline{H}_3$ (Ph)); 56.60 (NC$\underline{H}_2$Ph); 58.39 (C$_q$); 113.72 (2×C$\underline{H}$ (Ph)); 120.36 (C≡N); 130.01 (2×C$\underline{H}$ (Ph)); 130.79 (C$_q$(Ph)); and 158.83 (C$_q$ (Ph));

IR (cm$^{-1}$): 1453, 1510, 1584, 1611 (Ph); 2360 (C≡N); and
MS$^{ES}$ m/z (%): 243 (M+H$^+$, 100); 244 (15).
Compound 5c (yield 59%) was obtained from isopropylamine:
$^1$H-NMR (300 MHz, CDCl$_3$) (ppm): 1.12 (6H, d, J=6.6 Hz, 2×C$\underline{H}_3$ (iso-propyl)); 1.98 (2H, td, J=6.9 Hz, J=2.8 Hz, C$\underline{H}_2$); 2.12 (2H, dd (+2 symm. side lines), J=6.9 Hz, J=2.8 Hz (J=10.2 Hz from centre of signal), 2×C$_q$C$\underline{H}_a$H$_b$); 2.40-2.48 (1H, m, C$\underline{H}$); 2.48-2.55 (2H, m, 2×C$_q$CH$_a$$\underline{H}_b$); 2.97 (2H, t, J=6.6 Hz, NC$\underline{H}_2$); and 3.54 (1H, septet, J=6.6 Hz, C$\underline{H}$ (iso-propyl));

$^{13}$C-NMR (75 MHz, CDCl$_3$) (ppm): 18.43 (2×C$\underline{H}_3$ (iso-propyl)); 28.48 (C$\underline{H}_2$); 30.87 (C$\underline{H}$); 35.74 (NC$\underline{H}_2$); 40.11 (2×C$_q$C$\underline{H}_2$); 52.43 (C$\underline{H}$ (iso-propyl)); 57.01 (C$_q$); and 120.24 (C≡N);

IR (cm$^{-1}$): 2359 (C≡N); and
MS$^{ES}$ m/z (%): 165 (M+H$^+$, 100); 166 (15).
Compound 5d (yield 73%) was obtained from n-propylamine:
$^1$H-NMR (300 MHz, CDCl$_3$) (ppm): 0.94 (3H, t, J=7.2 Hz, C$\underline{H}_3$ (n-propyl)); 1.53 (2H, sextet, J=7.2 Hz, C$\underline{H}_2$ (n-propyl)); 1.94 (2H, td, J=6.6 Hz, J=2.8 Hz, C$\underline{H}_2$); 2.17 (2H, dd (+2 symm. side lines), J=6.6 Hz, J=2.8 Hz (J=10.2 Hz from centre of signal), 2×C$_q$C$\underline{H}_a$H$_b$); 2.37 (2H, td (+2 symm. side lines), J=6.6 Hz, J=2.8 Hz (J=14.0 Hz from centre of signal), 2×C$_q$CH$_a$$\underline{H}_b$); 2.48 (1H, septet, J=2.8 Hz, C$\underline{H}$); 2.63 (2H, t, J=7.2 Hz, NC$\underline{H}_2$ (n-propyl)); and 3.00 (2H, t, J=6.6 Hz, NC$\underline{H}_2$);

$^{13}$C-NMR (75 MHz, CDCl$_3$) (ppm): 11.57 (C$\underline{H}_3$ (n-propyl)); 21.86 (C$\underline{H}_2$ (n-propyl)); 27.82 (C$\underline{H}_2$); 31.10 (C$\underline{H}$); 37.24 (2×C$_q$C$\underline{H}_2$); 43.15 (NC$\underline{H}_2$); 55.51 (NC$\underline{H}_2$ (n-propyl)); 58.37 (C$_q$); and 120.33 (C≡N);

IR (cm$^{-1}$): 2360 (C≡N); and
MS$^{ES}$ m/z (%): 165 (M+H$^+$, 100); 166 (15).
Compound 5e (yield 78%) was obtained from isobutylamine:
$^1$H-NMR (300 MHz, CDCl$_3$) (ppm): 0.94 (6H, d, J=6.6 Hz, 2×C$\underline{H}_3$ (iso-butyl)); 1.71 (1H, septet, J=6.6 Hz, C$\underline{H}$ (iso-butyl)); 1.92 (2H, td, J=6.6 Hz, J=3.3 Hz, C$\underline{H}_2$); 2.18 (2H, dd (+2 symm. side lines), J=7.2 Hz, J=2.8 Hz (J=10.4 Hz from centre of signal), 2×C$_q$C$\underline{H}_a$H$_b$); 2.34 (2H, td (+2 symm. side lines), J=7.2 Hz, J=2.8 Hz (J=14.0 Hz from centre of signal), 2×C$_q$CH$_a$$\underline{H}_b$); 2.42 (2H, d, J=7.2 Hz, C$\underline{H}_2$ (iso-butyl)); 2.48 (1H, septet, J=3.3 Hz, C$\underline{H}$); and 2.99 (2H, t, J=6.6 Hz, NC$\underline{H}_2$);

$^{13}$C-NMR (75 MHz, CDCl$_3$) (ppm): 20.49 (2×C$\underline{H}_3$ (iso-butyl)); 27.60 (C$\underline{H}$ (iso-butyl)); 27.71 (C$\underline{H}_2$); 31.09 (C$\underline{H}$); 37.09 (2×C$_q$C$\underline{H}_2$); 43.74 (NC$\underline{H}_2$); 58.80 (C$_q$); 61.77 (NC$\underline{H}_2$ (iso-butyl)); and 120.34 (C≡N);

IR (cm$^{-1}$): 2361 (C≡N); and
MS$^{ES}$ m/z (%): 179 (M+H$^+$, 100); 180 (15).
Compound 5f (yield 79%) was obtained from n-butylamine:
$^1$H-NMR (300 MHz, CDCl$_3$) (ppm): 0.94 (3H, t, J=7.2 Hz, C$\underline{H}_3$ (n-butyl)); 1.37 (2H, sextet, J=7.2 Hz, C$\underline{H}_2$CH$_3$ (n-butyl)); 1.50 (2H, quintet, J=7.2 Hz, C$\underline{H}_2$CH$_2$ (n-butyl)); 1.94 (2H, td, J=6.6 Hz, J=3.3 Hz, C$\underline{H}_2$); 2.17 (2H, dd (+2 symm. side lines), J=7.2 Hz, J=2.8 Hz (J=10.4 Hz from centre of signal), 2×C$_q$C$\underline{H}_a$H$_b$); 2.37 (2H, td (+2 symm. side lines), J=7.2 Hz, J=2.8 Hz (J=14.0 Hz from centre of signal), 2×C$_q$CH$_a$$\underline{H}_b$); 2.48 (1H, septet, J=3.3 Hz, C$\underline{H}$); 2.67 (2H, t, J=7.2 Hz, NC$\underline{H}_2$ (n-butyl)); and 2.99 (2H, t, J=6.6 Hz, NC$\underline{H}_2$);

$^{13}$C-NMR (75 MHz, CDCl$_3$) (ppm): 13.99 (C$\underline{H}_3$ (n-butyl)); 20.31 (C$\underline{H}_2$CH$_3$ (n-butyl)); 27.80 (C$\underline{H}_2$); 30.69 (C$\underline{H}_2$CH$_2$ (n-butyl)); 31.07 (CH); 37.24 (2×C$_q$CH$_2$); 43.16 (NCH$_2$); 53.42 (NCH$_2$ (n-butyl)); 58.39 (C$_q$); and 120.21 (C≡N);

IR (cm$^{-1}$): 2360 (C≡N); and

MS$^{ES}$ m/z (%): 179 (M+H$^+$, 100); 180 (15); 195 (5).

Compound 5g (yield 70%) was obtained from 4-methylbenzylamine:

$^1$H-NMR (300 MHz, CDCl$_3$) (ppm): 1.89 (2H, td, J=6.6 Hz, J=3.3 Hz, CH$_2$); 2.23 (2H, dd (+2 symm. side lines), J=7.2 Hz, J=2.8 Hz (J=10.2 Hz from centre of signal), 2×C$_q$CH$_a$H$_b$); 2.33 (3H, s, CH$_3$ (Ph)); 2.40 (2H, td (+2 symm. side lines), J=7.2 Hz, J=2.8 Hz (J=14.0 Hz from centre of signal), 2×C$_q$CH$_a$H$_b$); 2.48 (1H, septet, J=3.3 Hz, CH); 2.84 (2H, t, J=6.6 Hz, NCH$_2$); 3.81 (2H, s, NCH$_2$Ph); 7.13 (2H, d, J=8.00 Hz, 2×CH (Ph)); and 7.25 (2H, d, J=8.00 Hz, 2×CH (Ph));

$^{13}$C-NMR (75 MHz, CDCl$_3$) (ppm): 21.00 (CH$_3$ (Ph)); 27.52 (CH$_2$); 31.13 (CH); 37.04 (2×C$_q$CH$_2$); 42.46 (NCH$_2$); 56.78 (NCH$_2$Ph); 58.30 (C$_q$); 120.22 (C≡N); 128.66 (2×CH (Ph)); 128.90 (2×CH (Ph)); 135.59 (C$_q$ (Ph)); and 136.66 (C$_q$ (Ph));

IR (cm$^{-1}$): 1527 (Ph); 2361 (C≡N); and

MS$^{ES}$ m/z (%): 227 (M+H$^+$, 100); 228 (15).

Compound 5h (yield 70%) was obtained from 2-aminomethylpyridine:

$^1$H-NMR (300 MHz, CDCl$_3$) (ppm): 1.96 (2H, td, J=6.6 Hz, J=3.3 Hz, CH$_2$); 2.30 (2H, dd (+2 symm. side lines), J=7.2 Hz, J=2.2 Hz (J=10.4 Hz from centre of signal), 2×C$_q$CH$_a$H$_b$); 2.44 (2H, td (+2 symm. side lines), J=7.2 Hz, J=2.2 Hz (J=13.2 Hz from centre of signal), 2×C$_q$CH$_a$H$_b$); 2.53 (1H, septet, J=3.3 Hz, CH); 2.98 (2H, t, J=6.6 Hz, NCH$_2$); 4.02 (2H, s, NCH$_2$pyr.); 7.19 (1H, ddd, J=7.7 Hz, J=5.0 Hz, J=1.7 Hz, NCHCH (pyr.)); 7.54 (1H, d, J=7.7 Hz, C$_q$CH (pyr.)); 7.69 (1H, td, J=7.7 Hz, J=1.7 Hz, C$_q$CHCH (pyr.)); and 8.53 (1H, dt, J=5.0 Hz, J=1.7 Hz, NCH (pyr.));

$^{13}$C-NMR (75 MHz, CDCl$_3$) (ppm): 27.59 (CH$_2$); 31.25 (CH); 37.09 (2×C$_q$CH$_2$); 43.15 (NCH$_2$); 58.45 (C$_q$); 58.95 (NCH$_2$pyr.); 120.18 (C≡N); 122.27 (NCHCH (pyr.)); 123.21 (C$_q$CH (pyr.)); 136.73 (C$_q$CHCH (pyr.)); 148.89 (NCH (pyr.)); and 159.19 (C$_q$ (pyr.));

IR (cm$^{-1}$): 1569 (Pyrid.) and 2361 (C≡N); and

MS$^{ES}$ m/z (%): 214 (M+H$^+$, 100); 215 (10).

Compound 5i (yield 55%) was obtained from 3-aminomethylpyridine.

$^1$H-NMR (300 MHz, CDCl$_3$) (ppm): 1.94 (2H, td, J=6.6 Hz, J=3.3 Hz, CH$_2$); 2.25 (2H, dd (+2 symm. side lines), J=7.2 Hz, J=2.8 Hz (J=10.3 Hz from centre of signal), 2×C$_q$CH$_a$H$_b$); 2.45 (2H, td (+2 symm. side lines), J=7.2 Hz, J=2.8 Hz (J=13.7 Hz from centre of signal), 2×C$_q$CH$_a$H$_b$); 2.53 (1H, septet, J=3.3 Hz, CH); 2.85 (2H, t, J=6.6 Hz, NCH$_2$); 3.88 (2H, s, NCH$_2$pyr.); 7.28 (1H, dd, J=8.3 Hz, J=4.4 Hz, NCHCH (pyr.)); 7.75 (1H, d, J=8.3 Hz, C$_q$CH (pyr.)); 8.52 (1H, d, J=4.4 Hz, NCHCH (pyr.)); and 8.53 (1H, dt, J=5.0 Hz, J=1.7 Hz, C$_q$CHN (pyr.));

$^{13}$C-NMR (75 MHz, CDCl$_3$) (ppm): 27.51 (CH$_2$); 31.18 (CH); 37.09 (2×C$_q$CH$_2$); 42.86 (NCH$_2$); 54.55 (NCH$_2$pyr.); 58.39 (C$_q$); 120.04 (C≡N); 123.46 (NCHCH (pyr.)); 134.31 (C$_q$ (pyr.)); 136.47 (C$_q$CH (pyr.)); 148.76 (NCHCH (pyr.)); and 149.89 (C$_q$CHN (pyr.));

IR (cm$^{-1}$): 1577, 1682 (Pyrid.) and 2361 (C≡N); and

MS$^{ES}$ m/z (%): 214 (M+H$^+$, 100); 215 (10).

Compound 5j (yield 65%) was obtained from 4-aminomethylpyridine:

$^1$H-NMR (300 MHz, CDCl$_3$) (ppm): 1.95 (2H, td, J=6.6 Hz, J=3.3 Hz, CH$_2$); 2.26 (2H, dd (+2 symm. side lines), J=7.2 Hz, J=2.2 Hz (J=10.2 Hz from centre of signal), 2×C$_q$CH$_a$H$_b$); 2.47 (2H, td (+2 symm. side lines), J=7.2 Hz, J=2.2 Hz (J=13.2 Hz from centre of signal), 2×C$_q$CH$_a$H$_b$); 2.55 (1H, septet, J=3.3 Hz, CH); 2.88 (2H, t, J=6.6 Hz, NCH$_2$); 3.88 (2H, s, NCH$_2$pyr.); 7.34 (2H, d, J=5.6 Hz, 2×C$_q$CH (pyr.)); and 8.57 (2H, d, J=5.6 Hz, 2×NCH (pyr.));

$^{13}$C-NMR (75 MHz, CDCl$_3$) (ppm): 27.62 (CH$_2$); 31.21 (CH); 37.21 (2×C$_q$CH$_2$); 43.41 (NCH$_2$); 56.34 (NCH$_2$pyr.); 58.42 (C$_q$); 119.93 (C≡N); 123.53 (2×C$_q$CH (pyr.)); 148.22 (C$_q$ (pyr.)); and 149.76 (2×NCH (pyr.));

IR (cm$^{-1}$): 1561, 1602 (Pyrid.) and 2361 (C≡N); and

MS$^{ES}$ m/z (%): 214 (M+H$^+$, 100); 215 (10).

Compound 5k (yield 80%) was obtained from 2,4-dimethoxybenzylamine:

$^1$H-NMR (300 MHz, CDCl$_3$) (ppm): 1.92 (2H, td, J=6.6 Hz, J=3.3 Hz, CH$_2$); 2.29 (2H, dd (+2 symm. side lines), J=7.4 Hz, J=2.2 Hz (J=10.4 Hz from centre of signal), 2×C$_q$CH$_a$H$_b$); 2.39 (2H, td (+2 symm. side lines), J=7.4 Hz, J=2.2 Hz (J=14.0 Hz from centre of signal), 2×C$_q$CH$_a$H$_b$); 2.49 (1H, septet, J=3.3 Hz, CH); 2.95 (2H, t, J=6.6 Hz, NCH$_2$); 3.80 (2H, s, NCH$_2$ (Ph)); 3.82 (6H, s, 2×OCH$_3$ (Ph)); 6.45 (1H, s, C$_q$CHC$_q$ (Ph)); 6.47 (1H, d, J=8.3 Hz, C$_q$CHCH (Ph)); and 7.30 (1H, d, J=8.3 Hz, C$_q$CHCH (Ph));

$^{13}$C-NMR (75 MHz, CDCl$_3$) (ppm): 27.79 (CH$_2$); 31.33 (CH); 37.27 (2×C$_q$CH$_2$); 42.54 (NCH$_2$); 50.42 (NCH$_2$ (Ph)); 55.39 (2×OCH$_3$ (Ph)); 58.58 (C$_q$); 98.48 (C$_q$CHC$_q$ (Ph)); 104.19 (C$_q$CHCH (Ph)); 119.55 (C$_q$ (Ph)); 120.47 (C≡N); 130.94 (C$_q$CHCH (Ph)); 158.71 (C$_q$ (Ph)); and 160.15 (C$_q$ (Ph));

IR (cm$^{-1}$): 1454, 1504, 1590, 1614 (Ph) and 2363 (C≡N); and

MS$^{ES}$ m/z (%): 214 (100); 273 (M+H$^+$, 70); 274 (15).

Compound 5l (yield 72%) was obtained from p-anisidine:

$^1$H-NMR (300 MHz, CDCl$_3$) (ppm): 2.04 (2H, ~t, J=6.6 Hz, CH$_2$); 2.42 (2H, dd (+2 symm. side lines), J=7.4 Hz, J=2.2 Hz (J=11.1 Hz from centre of signal), 2×C$_q$CH$_a$H$_b$); 2.56-2.62 (3H, m, 2×C$_q$CH$_a$H$_b$, CH); 3.70 (2H, t, J=6.6 Hz, NCH$_2$); 3.78 (3H, s, OCH$_3$ (Ph)); 6.86 (2H, d, J=8.8 Hz, 2×CH (Ph)); and 7.00 (2H, d, J=8.8 Hz, 2×CH (Ph));

$^{13}$C-NMR (75 MHz, CDCl$_3$) (ppm): 29.70 (CH$_2$); 30.93 (CH); 38.61 (2×C$_q$CH$_2$); 46.87 (NCH$_2$); 55.56 (OCH$_3$ (Ph)); 55.96 (C$_q$); 114.33 (2×CH (Ph)); 119.84 (C≡N); 121.95 (2×CH (Ph)); 142.68 (C$_q$ (Ph)); and 154.86 (C$_q$ (Ph));

IR (cm$^{-1}$): 1579, 1637 (Ph) and 2359 (C≡N); and

MS$^{ES}$ m/z (%): 229 (M+H$^+$, 100); 230 (15); 277 (25).

Compound 5m (yield 92%) was obtained from ethylamine:

$^1$H-NMR (300 MHz, CDCl$_3$) (ppm): 1.15 (3H, t, J=7.2 Hz, CH$_3$ (ethyl)); 1.95 (2H, td, J=6.6 Hz, J=2.8 Hz, CH$_2$); 2.17 (2H, dd (+2 symm. side lines), J=6.9 Hz, J=2.8 Hz (J=11.4 Hz from centre of signal), 2×C$_q$CH$_a$H$_b$); 2.39 (2H, td (+2 symm. side lines), J=6.9 Hz, J=2.8 Hz (J=14.3 Hz from centre of signal), 2×C$_q$CH$_a$H$_b$); 2.49 (1H, ~septet, J=2.8 Hz, CH); 2.77 (2H, q, J=7.2 Hz, NCH$_2$ (ethyl)); and 3.00 (2H, t, J=6.6 Hz, NCH$_2$), $^{13}$C-NMR (75 MHz, CDCl$_3$) (ppm): 13.70 (CH$_3$ (ethyl)); 27.85 (CH$_2$); 31.05 (CH); 37.36 (2×C$_q$CH$_2$); 42.57 (NCH$_2$); 47.67 (NCH$_2$ (ethyl)); 58.16 (C$_q$); and 120.21 (C≡N);

IR (cm$^{-1}$): 2362 (C≡N); and

MS$^{ES}$ m/z (%): 151 (M+H$^+$, 100); 231 (10).

Compound 5n (yield 75%) was obtained from methylamine:

$^1$H-NMR (300 MHz, CDCl$_3$) (ppm): 1.96 (2H, td, J=6.6 Hz, J=3.3 Hz, CH$_2$); 2.15 (2H, dd (+2 symm. side lines), J=7.2 Hz, J=2.8 Hz (J=10.5 Hz from centre of signal), 2×C$_q$CH$_a$H$_b$); 2.39 (2H, td (+2 symm. side lines), J=7.2 Hz, J=2.8 Hz (J=13.5 Hz from centre of signal), 2×C$_q$CH$_a$H$_b$); 2.46-2.53 (1H, m, CH); 2.51 (3H, s, NCH$_3$); and 2.97 (2H, t, J=6.6 Hz, NCH$_2$);

$^{13}$C-NMR (75 MHz, CDCl$_3$) (ppm): 28.14 (CH$_2$); 31.30 (CH); 36.74 (2×C$_q$CH$_2$); 41.33 (NCH$_3$); 47.12 (NCH$_2$); 57.76 (C$_q$); and 119.67 (C≡N);

IR (cm$^{-1}$): 2359 (C≡N); and

MS$^{ES}$ m/z (%): 137 (M+H$^+$, 100); 138 (10).

Example 3

Preparation of 1-substituted-2-$R_0$-2-azabicyclo[3.1.1]heptyl derivatives

In a first step, a nitrile compound 5 of example 2 was submitted to a partial reduction as shown in scheme 3 below, followed by acidic hydrolysis. Infrared analysis confirmed the reduction to the expected aldimine which however was quite resistant to hydrolysis, chromatography being needed to obtain the pure aldehyde in 56% yield. The subsequent addition of the 2-chloropyridyl group provides the alcohol 7.

Alternatively, the nucleophilic addition of the 2-chloropyridyl group can also be performed directly onto the nitrile compound 5. After acidic hydrolysis of the resulting imine, the ketone 9 is obtained.

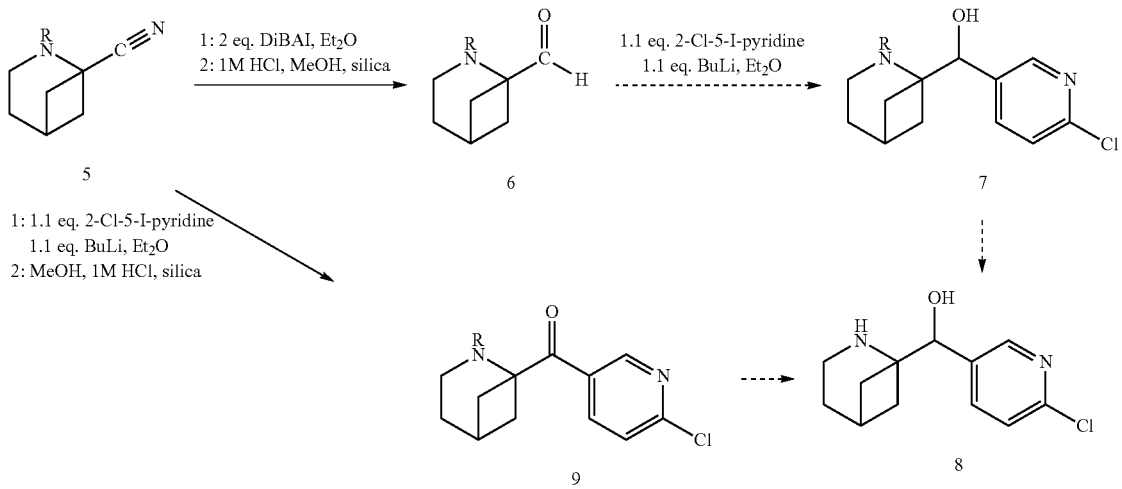

Scheme 3

Synthesis of compounds 6 (2-$R_0$-2-azabicyclo[3.1.1]heptyl-1-carbaldehydes)

In a dry 100 ml flask 3 mmole of a 2-$R_0$-2-azabicyclo[3.1.1]heptyl-1-carbonitrile 5 was dissolved in 35 ml dry diethyl ether. The flask was placed under an inert $N_2$-atmosphere and cooled to −78° C. With a syringe, 6 ml of a 1M solution of di-isobutylaluminum hydride (DiBAl) in hexane (6 mmole) was added. The reaction mixture was stirred for one hour at −78° C. and 2 hours at room temperature. Then 0.44 g (6 mmole) of ethyl formate were added. After stirring for half an hour, 20 ml of 1M HCl was added together with 20 ml of methanol and a spoon of silica. The reaction mixture was neutralised by means of 3M NaOH after 15 hours, followed by extraction, using three times diethyl ether and combining the organic phases to dry over $MgSO_4$. After filtration of the solids and removal of the volatile components, the resulting product was characterised by proton ($^1$H-NMR) and carbon ($^{13}$C-NMR) nuclear magnetic resonance, mass spectrum ($MS^{ES}$) and infrared (IR) spectrophotometry. As a representative example, the data for the carbaldehyde 6b resulting from compound 5b are as follows:

Compound 6b (yield 56%)

$^1$H-NMR (300 MHz, $CDCl_3$) (ppm): 1.99 (4H, dd (+2 symm. side lines), J=7.2 Hz, J=2.8 Hz (J=9.4 Hz from centre of signal), C$\underline{H}_2$, C$_q$C$\underline{H}_a$H$_b$); 2.13 (2H, td (+2 symm. side lines), J=7.2 Hz, J=2.8 Hz (J=14.0 Hz from centre of signal), C$_q$CH$_a$$\underline{H}_b$); 2.45 (1H, septet, J=2.8 Hz, C$\underline{H}$); 3.01 (2H, t, J=7.2 Hz, NC$\underline{H}_2$); 3.53 (2H, s, NC$\underline{H}_2$Ph); 3.80 (3H, s, OC$\underline{H}_3$, Ph); 6.86 (2H, dt, J=8.3 Hz, J=2.8 Hz, 2×C$\underline{H}$, Ph); 7.30 (2H, dt, J=8.3 Hz, J=3.3 Hz, 2×C$\underline{H}$, Ph); and 9.45 (1H, d, J=1.1 Hz, CO$\underline{H}$);

$^{13}$C-NMR (75 MHz, $CDCl_3$) (ppm): 28.64 ($\underline{C}H_2$); 29.45 ($\underline{C}H$); 32.63 (2×$\underline{C}_q\underline{C}H_2$); 42.92 (N$\underline{C}H_2$); 55.27 (O$\underline{C}H_3$, Ph); 56.29 (N$\underline{C}H_2$Ph); 73.44 ($\underline{C}_q$); 113.76 (2×$\underline{C}H$, Ph); 130.07 (2×$\underline{C}H$, Ph); 131.43 ($\underline{C}_q$, Ph); 158.93 ($\underline{C}_q$, Ph); and 202.35 ($\underline{C}$=O);

IR (cm$^{-1}$): 1722 (C=O); and $MS^{ES}$ m/z (%): 264 (M+$H_3O^+$, 20); 246 (M+H$^+$, 100).

Synthesis of Compounds 7

In a dry 50 ml flask 1.1 g (4.6 mmole) 2-chloro-5-iodopyridine is dissolved in 30 ml dry diethyl ether. The flask is placed under an inert $N_2$-atmosphere and cooled to −78° C. To this solution 1.84 ml of a 2.5M solution (4.6 mmole) of butyl lithium (BuLi) is added. After stirring for 2.5 hours at −78° C. a solution of 0.90 g (4.2 mmole) of a 2-$R_0$-2-azabicyclo[3.1.1]heptyl-1-carbaldehyde 6 in 10 ml dry diethyl ether is added. After 30 minutes, the reaction mixture is allowed to heat up to room temperature and left under agitation overnight. Methanol is added in order to neutralise the excess of BuLi and the volatile components are evaporated. The reaction mixture is re-dissolved in a minimal amount of dry diethyl ether. The volatile components are evaporated and the precipitated salts are filtered off.

Synthesis of Compounds 9

In a dry 50 ml flask 0.55 g (2.3 mmol.) 2-chloro-5-iodopyridine was dissolved in 30 ml dry diethyl ether. The flask was placed under an inert $N_2$-atmosphere and cooled to −78° C. To this solution 1 ml of a 2.5M solution (2.3 mmole) of BuLi was added. After stirring for 2.5 hours at −78° C. a solution of 2.3 mmole of a 2-$R_0$-2-azabicyclo[3.1.1]heptyl-1-carbonitrile 5 in 10 ml dry diethyl ether was added. After 30 minutes, the reaction mixture was allowed to heat up to room temperature and left under agitation overnight. Methanol was added in order to neutralise the excess of BuLi and the volatile components were evaporated. The reaction mixture was re-dissolved in 40 ml of a 1:1 mixture of methanol and 1M HCl.

Silica gel (0.5 g) was added and the mixture was stirred for 24 hours at 20° C. The pH of the reaction mixture was adjusted to 8 by adding a concentrated $NaHCO_3$ solution. The resulting compound 9 was extracted three times by means of dichloromethane and the combined organic phases were dried over $MgSO_4$. After filtration of the solids and evaporation of the volatile components under reduced pressure, compound 9 was further purified by column chromatography and recrystallisation from methanol. The obtained products were characterised by proton ($^1$H-NMR) and carbon ($^{13}$C-NMR) nuclear magnetic resonance, mass spectrum ($MS^{ES}$) and infrared (IR) spectrophotometry as follows:

Compound 9a (yield 45%)

$^1$H-NMR (300 MHz, $CDCl_3$) (ppm): 2.04 (2H, td, J=6.9 Hz, J=3.3 Hz, C$\underline{H}_2$); 2.19-2.34 (4H, m, 2×C$_q$C$\underline{H}_aH_b$); 2.50 (1H, septet, J=3.3 Hz, C$\underline{H}$); 3.06 (2H, t, J=6.9 Hz, NC$\underline{H}_2$); 3.53 (2H, s, NC$\underline{H}_2$Ph); 7.05-7.09 (2H, m, 2×C$\underline{H}$, Ph); 7.15-7.23 (3H, m, 3×C$\underline{H}$, Ph); 7.40 (1H, d, J=8.3 Hz, C$_q$CHC$\underline{H}$, pyr.); 8.45 (1H, dd, J=8.3 Hz, J=2.2 Hz, C$_q$C$\underline{H}$CH, pyr.); and 9.47 (1H, d, J=2.2 Hz, C$_q$C$\underline{H}$N, pyr.);

$^{13}$C-NMR (75 MHz, $CDCl_3$) (ppm): 28.57 ($\underline{C}H_2$); 29.25 ($\underline{C}H$); 34.57 (2×C$_q\underline{C}H_2$); 42.83 (N$\underline{C}H_2$); 56.40 (N$\underline{C}H_2$Ph); 74.14 ($\underline{C}_q$); 124.10 ($\underline{C}_q$CHCH, pyr.); 127.03 ($\underline{C}H$, Ph); 128.27 (2×$\underline{C}H$, Ph); 128.40 (2×$\underline{C}H$, Ph); 128.95 ($\underline{C}_q$, pyr.); 139.02 ($\underline{C}_q$, Ph); 139.66 (C$_q$$\underline{C}$HCH, pyr.); 152.01 ($\underline{C}_q$CHN, pyr.); 155.11 ($\underline{C}_q$Cl, pyr.); and 198.29 ($\underline{C}$=O);

IR ($cm^{-1}$): 1675 (C=O); and $MS^{ES}$ m/z (%): 327 ($M+H^+$, 100); 329 ($M+H^+$, 30); 330 (5).

Compound 9b (yield 54%)

$^1$H-NMR (300 MHz, $CDCl_3$) (ppm): 2.03 (2H, td, J=6.6 Hz, J=3.3 Hz, C$\underline{H}_2$); 2.17-2.32 (4H, m, 2×C$_q$C$\underline{H}_aH_b$); 2.49 (1H, septet, J=3.3 Hz, C$\underline{H}$); 3.05 (2H, t, J=6.6 Hz, NC$\underline{H}_2$); 3.47 (2H, s, NC$\underline{H}_2$Ph); 3.75 (3H, s, OC$\underline{H}_3$, Ph); 6.73 (2H, d, J=8.5 Hz, 2×C$\underline{H}$, Ph); 6.96 (2H, d, J=8.5 Hz, 2×C$\underline{H}$, Ph); 7.40 (1H, d, J=8.3 Hz, C$_q$CHC$\underline{H}$, pyr.); 8.43 (1H, dd, J=8.3 Hz, J=2.2 Hz, C$_q$C$\underline{H}$CH, pyr.); and 9.45 (1H, d, J=2.2 Hz, C$_q$C$\underline{H}$N, pyr.);

$^{13}$C-NMR (75 MHz, $CDCl_3$) (ppm): 28.63 ($\underline{C}H_2$); 29.28 ($\underline{C}H$); 34.57 (2×C$_q\underline{C}H_2$); 42.77 (N$\underline{C}H_2$); 55.24 (O$\underline{C}H_3$, Ph); 55.85 (N$\underline{C}H_2$Ph); 74.11 ($\underline{C}_q$); 113.59 (2×$\underline{C}H$, Ph); 124.05 (C$_q$CH$\underline{C}$H, pyr.); 128.98 ($\underline{C}_q$, pyr.); 129.64 (2×$\underline{C}H$, Ph); 131.00 ($\underline{C}_q$, Ph); 139.64 (C$_q\underline{C}$HCH, pyr.); 151.98 ($\underline{C}_q$CHN, pyr.); 155.05 ($\underline{C}_q$Cl, pyr.); 158.67 ($\underline{C}_q$, Ph); and 198.30 ($\underline{C}$=O);

IR ($cm^{-1}$): 1675 (C=O); and $MS^{ES}$ m/z (%): 357 ($M+H^+$, 100); 359 ($M+H^+$, 35); 358 (20); 360 (5).

Compound 9k (yield 65%)

$^1$H-NMR (300 MHz, $CDCl_3$) (ppm): 2.05 (2H, td, J=6.6 Hz, J=3.3 Hz, C$\underline{H}_2$); 2.20-2.25 (4H, m, 2×C$_q$C$\underline{H}_aH_b$); 2.43-2.50 (1H, m, C$\underline{H}$); 3.12 (2H, t, J=6.6 Hz, NC$\underline{H}_2$); 3.49 (5H, br. s, OC$\underline{H}_3$ (Ph), NC$\underline{H}_2$Ph); 3.75 (3H, s, OC$\underline{H}_3$, Ph); 6.25 (1H, d, J=2.2 Hz, C$\underline{H}$, Ph); 6.32 (1H, dd, J=8.3 Hz, J=2.2 Hz, C$\underline{H}$, Ph); 6.95 (1H, d, J=8.3 Hz, C$\underline{H}$, Ph); 7.33 (1H, d, J=8.3 Hz, C$_q$CHC$\underline{H}$, pyr.); 8.40 (1H, dd, J=8.3 Hz, J=2.2 Hz, C$_q$C$\underline{H}$CH, pyr.); and 9.39 (1H, d, J=2.2 Hz, C$_q$C$\underline{H}$N, pyr.);

$^{13}$C-NMR (75 MHz, $CDCl_3$) (ppm): 28.72 ($\underline{C}H_2$); 29.33 ($\underline{C}H$); 34.54 (2×C$_q\underline{C}H_2$); 42.98 (N$\underline{C}H_2$); 50.29 (N$\underline{C}H_2$Ph); 54.78 (O$\underline{C}H_3$, Ph); 55.33 (O$\underline{C}H_3$, Ph); 74.19 ($\underline{C}_q$); 98.11 ($\underline{C}H$, Ph); 103.59 ($\underline{C}H$, Ph); 119.50 ($\underline{C}_q$, Ph); 123.64 (C$_q$CH$\underline{C}$H, pyr.); 129.20 ($\underline{C}_q$, pyr.); 130.80 ($\underline{C}H$, Ph); 139.66 (C$_q\underline{C}$HCH, pyr.); 152.15 ($\underline{C}_q$CHN, pyr.); 154.59 ($\underline{C}_q$Cl, pyr.); 158.64 ($\underline{C}_q$, Ph); and 198.03 ($\underline{C}$=O);

IR ($cm^{-1}$): 1675 (C=O); and $MS^{ES}$ m/z (%): 387 ($M+H^+$, 100); 388 (20); 389 ($M+H^+$, 35); 390 (5).

Compound 9m (yield 62%)

$^1$H-NMR (300 MHz, $CDCl_3$) (ppm): 0.87 (3H, t, J=7.2 Hz, C$\underline{H}_3$ (ethyl)); 2.04 (2H, td, J=6.6 Hz, J=2.8 Hz, C$\underline{H}_2$); 2.06 (2H, dd (+2 symm. side lines), J=7.2 Hz, J=2.8 Hz (J=10.5 Hz from centre of signal), 2×C$_q$C$\underline{H}_aH_b$); 2.21 (2H, td (+2 symm. side lines), J=7.2 Hz, J=2.8 Hz (J=14.3 Hz from centre of signal), 2×C$_q$CH$_a\underline{H}_b$); 2.35 (2H, q, J=7.2 Hz, NC$\underline{H}_2$ (ethyl)); 2.43 (1H, ~septet, J=2.8 Hz, C$\underline{H}$); 3.14 (2H, t, J=6.6 Hz, NC$\underline{H}_2$); 7.39 (1H, d, J=8.3 Hz, C$_q$CHC$\underline{H}$ (pyr.)); 8.51 (1H, dd, J=8.3 Hz, J=2.8 Hz, C$_q$C$\underline{H}$CH (pyr.)); and 9.41 (1H, d, J=1.7 Hz, C$_q$C$\underline{H}$N (pyr.));

$^{13}$C-NMR (75 MHz, $CDCl_3$) (ppm): 14.21 ($\underline{C}H_3$ (ethyl)); 28.72 ($\underline{C}H_2$); 28.95 ($\underline{C}H$); 34.77 (2×C$_q\underline{C}H_2$); 42.40 (N$\underline{C}H_2$); 46.78 (N$\underline{C}H_2$ (ethyl)); 74.34 ($\underline{C}_q$); 123.92 (C$_q$CH$\underline{C}$H, pyr.); 129.08 ($\underline{C}_q$, pyr.); 139.73 (C$_q\underline{C}$HCH (pyr.)); 152.04 ($\underline{C}_q$CHN (pyr.)); 154.96 ($\underline{C}_q$Cl, pyr.); and 198.53 ($\underline{C}$=O);

IR ($cm^{-1}$): 1673 (C=O); and $MS^{ES}$ m/z (%): 265 ($M+H^+$, 100); 266 (15); 267 ($M+H^+$, 35).

Example 4

Preparation and derivatisation of 2-$R_0$-2-azabicyclo[3.1.1]hept-1-yl)(pyridin-3-yl)methanone Ketones 10 were synthesised from 2-substituted-2-azabicyclo[3.1.1]heptane-1-carbonitriles 5 as shown in scheme 4. Afterwards, refluxing ketone 10a (R=benzyl) with ammonium formate in the presence of Pd/C led to the complete removal of the benzyl group within 4 hours and compound 11a was recovered after crystallisation from diethyl ether.

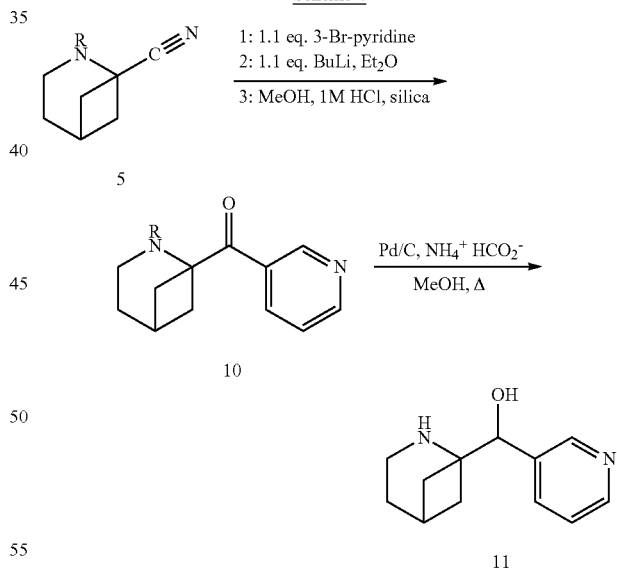

Scheme 4

Details of these syntheses are as follows:

Synthesis of Compounds 10

In a dry 50 ml flask, 2.8 mmole of a 2-$R_0$-2-azabicyclo[3.1.1]heptane-1-carbonitrile 5 and 0.48 g (3 mmole) 3-bromopyridine were dissolved in 25 ml dry diethyl ether. The flask was placed under an inert $N_2$-atmosphere and cooled to −78° C. With a syringe, 1.2 ml of a 2.5M solution of BuLi (3 mmole) was added over a period of 10 minutes. The reaction mixture was stirred for 30 minutes at −78° C. and then allowed to slowly heat up to room temperature. The mixture was left under agitation overnight. Methanol was added to neutralise the excess of BuLi and the volatile components were evaporated. The reaction mixture was re-dissolved in 20 ml of a 1:1 mixture of methanol and 1M HCl. Silica gel (0.5 g) was added to improve the hydrolysis and the mixture was stirred for 24 hours at room temperature. The pH of the solution was adjusted to 8 by adding a concentrated NaHCO$_3$ solution. The compound 10 was extracted three times by means of dichloromethane and the combined organic phases were dried over MgSO$_4$. After filtration of the solids and evaporation of the volatile components, compound 10 was purified by means of column chromatography. The obtained derivatives were characterised by proton ($^1$H-NMR) and carbon ($^{13}$C-NMR) nuclear magnetic resonance, mass spectrum (MS$^{ES}$) and infrared (IR) spectrophotometry as follows:

Compound 10a (yield 80%)

$^1$H-NMR (300 MHz, CDCl$_3$) (ppm): 2.04 (2H, td, J=6.9 Hz, J=3.3 Hz, CH$_2$); 2.22-2.37 (4H, m, 2×C$_q$CH$_a$H$_b$); 2.49 (1H, septet, J=3.3 Hz, CH); 3.06 (2H, t, J=6.9 Hz, NCH$_2$); 3.53 (2H, s, NCH$_2$Ph); 7.03-7.08 (2H, m, 2×CH, Ph); 7.13-7.21 (3H, m, 3×CH, Ph); 7.39 (1H, dd, J=8.3 Hz, J=4.4 Hz, C$_q$CHCH, pyr.); 8.49 (1H, dt, J=8.3 Hz, J=2.2 Hz, C$_q$CHCH, pyr.); 8.75 (1H, d, J=4.4 Hz, NCHCH, pyr.); and 9.64 (1H, s, C$_q$CHN, pyr.);

$^{13}$C-NMR (75 MHz, CDCl$_3$) (ppm): 28.63 (CH$_2$); 29.27 (CH); 34.66 (2×C$_q$CH$_2$); 42.75 (NCH$_2$); 56.32 (NCH$_2$Ph); 74.22 (C$_q$); 123.29 (C$_q$CHCH, pyr.); 126.92 (CH, Ph); 128.18 (2×CH, Ph); 128.44 (2×CH, Ph); 130.21 (C$_q$, pyr.); 136.99 (C$_q$CHCH, pyr.); 139.26 (C$_q$, Ph); 151.64 (C$_q$CHN, pyr.); and 153.08 (NCHCH, pyr.); 199.62 (C=O);

IR (cm$^{-1}$): 1583, 1610 (Ph) and 1686 (C=O); and

MS$^{ES}$ m/z (%): 293 (M+H$^+$, 100); 294 (20).

Compound 10b (yield 92%)

$^1$H-NMR (300 MHz, CDCl$_3$) (ppm): 2.04 (2H, td, J=6.3 Hz, J=3.3 Hz, CH$_2$); 2.21-2.36 (4H, m, 2×C$_q$CH$_a$H$_b$); 2.45-2.52 (1H, m, CH); 3.04 (2H, td, J=6.3 Hz, J=1.1 Hz, NCH$_2$); 3.46 (2H, s, NCH$_2$Ph); 3.74 (3H, d, J=1.7 Hz, OCH$_3$, Ph); 6.71 (2H, dd, J=8.3 Hz, J=1.7 Hz, 2×CH, Ph); 6.95 (2H, d, J=8.3 Hz, 2×CH, Ph); 7.39 (1H, ddd, J=8.0 Hz, J=5.0 Hz, J=1.1 Hz, C$_q$CHCH, pyr.); 8.49 (1H, ddd, J=8.0 Hz, J=3.6 Hz, J=2.0 Hz, C$_q$CHCH, pyr.); 8.76 (1H, dt, J=5.0 Hz, J=1.1 Hz, NCHCH, pyr.) and 9.89 (1H, s, C$_q$CHN, pyr.);

$^{13}$C-NMR (75 MHz, CDCl$_3$) (ppm): 28.67 (CH$_2$); 29.30 (CH); 34.66 (2×C$_q$CH$_2$); 42.61 (NCH$_2$); 55.21 (OCH$_3$, Ph); 55.73 (NCH$_2$Ph); 74.20 (C$_q$); 113.53 (2×CH, Ph); 123.26 (C$_q$CHCH, pyr.); 129.61 (2×CH, Ph); 130.24 (C$_q$, pyr.); 131.28 (C$_q$, Ph); 136.97 (C$_q$CHCH, pyr.); 151.64 (C$_q$CHN, pyr.); 153.05 (NCHCH, pyr.); 158.59 (C$_q$, Ph); and 199.66 (C=O);

IR (cm$^{-1}$): 1675 (C=O); and

MS$^{ES}$ m/z (%): 323 (M+H$^+$, 100); 324 (20); 392 (5).

Compound 10k (yield 90%)

$^1$H-NMR (300 MHz, CDCl$_3$) (ppm): 2.05 (2H, td, J=6.6 Hz, J=3.3 Hz, CH$_2$); 2.25-2.27 (4H, m, 2×C$_q$CH$_a$H$_b$); 2.44-2.50 (1H, m, CH); 3.12 (2H, t, J=6.6 Hz, NCH$_2$); 3.46 (3H, br. s, OCH$_3$, Ph); 3.49 (2H, br. s, NCH$_2$Ph); 3.74 (3H, s, OCH$_3$, Ph); 6.25 (1H, d, J=2.8 Hz, CH, Ph); 6.31 (1H, dd, J=8.3 Hz, J=2.8 Hz, CH, Ph); 6.97 (1H, d, J=8.3 Hz, CH, Ph); 7.33 (1H, dd, J=8.3 Hz, J=5.0 Hz, C$_q$CHCH, pyr.); 8.47 (1H, dt, J=8.3 Hz, J=1.7 Hz, C$_q$CHCH, pyr.); 8.70 (1H, dd, J=5.0 Hz, J=1.7 Hz, NCHCH, pyr.); and 9.59 (1H, s, C$_q$CHN, pyr.);

$^{13}$C-NMR (75 MHz, CDCl$_3$) (ppm): 28.66 (CH$_2$); 29.27 (CH); 34.58 (2×C$_q$CH$_2$); 42.67 (NCH$_2$); 49.96 (NCH$_2$Ph); 54.74 (OCH$_3$, Ph); 55.29 (OCH$_3$, Ph); 74.22 (C$_q$); 98.02 (CH, Ph); 103.46 (CH, Ph); 119.78 (C$_q$, Ph); 123.00 (C$_q$CHCH, pyr.); 130.39 (C$_q$, pyr.); 130.62 (CH, Ph); 137.02 (C$_q$CHCH, pyr.); 151.77 (C$_q$CHN, pyr.); 152.64 (NCHCH, pyr.); 158.56 (C$_q$, Ph); and 159.87 (C$_q$, Ph); 199.51 (C=O);

IR (cm$^{-1}$): 1675 (C=O); and

MS$^{ES}$ m/z (%): 353 (M+H$^+$, 100).

Compound 10l (yield 78%)

$^1$H-NMR (300 MHz, CDCl$_3$) (ppm): 2.12 (2H, td, J=6.6 Hz, J=2.8 Hz, CH$_2$); 2.30 (2H, br. s, 2×C$_q$CH$_a$H$_b$); 2.55-2.67 (3H, m, 2×C$_q$CH$_a$H$_b$, CH); 3.65 (3H, s, OCH$_3$ (Ph)); 3.87-3.96 (NCH$_2$); 6.63 (4H, s, 4×CH (Ph)); 7.24 (1H, dd, J=8.0 Hz, J=5.0 Hz, C$_q$CHCH (pyr.)); 8.29 (1H, dt, J=8.0 Hz, J=1.7 Hz, C$_q$CHCH, pyr.); 8.59 (1H, d, J=3.3 Hz, NCHCH, pyr.) and 9.39 (1H, s, C$_q$CHN, pyr.);

$^{13}$C-NMR (75 MHz, CDCl$_3$) (ppm): 28.81 (CH); 30.70 (CH$_2$); 36.78 (2×C$_q$CH$_2$); 46.89 (NCH$_2$); 55.41 (OCH$_3$, Ph); 72.36 (C$_q$); 114.33 (2×CH, Ph); 119.11 (2×CH, Ph); 123.24 (C$_q$CHCH, pyr.); 130.22 (C$_q$, pyr.); 136.47 (C$_q$CHCH, pyr.); 144.01 (C$_q$, Ph); 150.47 (C$_q$CHN, pyr.); 152.86 (NCHCH, pyr.); 153.08 (C$_q$, Ph); and 199.92 (C=O);

IR (cm$^{-1}$): 1677 (C=O); and

MS$^{ES}$ m/z (%): 309 (M+H$^+$, 100); 310 (20).

Compound 10m (yield 85%)

$^1$H-NMR (300 MHz, CDCl$_3$) (ppm): 0.87 (3H, t, J=7.2 Hz, CH$_3$ (ethyl)); 2.04 (2H, td, J=6.6 Hz, J=2.8 Hz, CH$_2$); 2.06 (2H, dd (+2 symm. side lines), J=7.2 Hz, J=2.8 Hz (J=10.5 Hz from centre of signal), 2×C$_q$CH$_a$H$_b$); 2.21 (2H, td (+2 symm. side lines), J=7.2 Hz, J=2.8 Hz (J=14.3 Hz from centre of signal), 2×C$_q$CH$_a$H$_b$); 2.35 (2H, q, J=7.2 Hz, NCH$_2$ (ethyl)); 2.43 (1H, ~septet, J=2.8 Hz, CH); 3.14 (2H, t, J=6.6 Hz, NCH$_2$); 7.39 (1H, ddd, J=8.0 Hz, J=5.0 Hz, J=1.1 Hz, C$_q$CHCH, pyr.); 8.49 (1H, ddd, J=8.0 Hz, J=3.6 Hz, J=2.0 Hz, C$_q$CHCH, pyr.); 8.76 (1H, dt, J=5.0 Hz, J=1.1 Hz, NCHCH, pyr.) and 9.89 (1H, s, C$_q$CHN, pyr.);

$^{13}$C-NMR (75 MHz, CDCl$_3$) (ppm): 14.21 (CH$_3$ (ethyl)); 28.72 (CH$_2$); 28.95 (CH); 34.77 (2×C$_q$CH$_2$); 42.40 (NCH$_2$); 46.78 (NCH$_2$ (ethyl)); 74.34 (C$_q$); 123.26 (C$_q$CHCH, pyr.); 129.61 (2×CH, Ph); 130.24 (C$_q$, pyr.); 131.28 (C$_q$, Ph); 136.97 (C$_q$CHCH, pyr.); 151.64 (C$_q$CHN, pyr.); 153.05 (NCHCH, pyr.); 158.59 (C$_q$, Ph); and 199.66 (C=O);

IR (cm$^{-1}$): 1583 (pyr.); 1679 (C=O); and

MS$^{ES}$ m/z (%): 231 (M+H$^+$, 100); 232 (15).

Synthesis of Compound 11a

In a 50 ml flask 0.10 g (0.34 mmole) 2-benzyl-2-azabicyclo[3.1.1]hept-1-yl)(pyridin-3-yl)methanone 10a and 0.09 g (1.37 mmole) ammonium formate were dissolved in 20 ml methanol. To this solution 0.05 g (5% Pd) Pd/C was added and the suspension was refluxed 4 hours. The Pd/C catalyst was filtered off and methanol evaporated. 5 ml dichloromethane was added and the excess ammonium formate was filtered off. After evaporation of dichloromethane, compound 11a (yield 86%) was further purified by crystallisation from diethyl ether. It was characterised by proton ($^1$H-NMR) and carbon ($^{13}$C-NMR) nuclear magnetic resonance, mass spectrum (MS$^{ES}$) and infrared (IR) spectrophotometry as follows:

$^1$H-NMR (300 MHz, CDCl$_3$) (ppm): 1.40 (1H, t, J=9.1 Hz, C$_q$CH$_a$H$_b$); 1.77 (1H, t, J=9.1 Hz, C$_q$CH$_a$H$_b$); 1.84-1.98 (4H, m, CH$_2$, 2×C$_q$CH$_a$H$_b$); 2.41 (1H, ~septet, J=3.3 Hz, CH); 2.98-3.28 (4H, m, NCH$_2$, NH, OH); 4.49 (1H, s, CHOH); 7.23 (1H, t, J=4.4 Hz, C$_q$CHCH (pyr.)); 7.66 (1H, dt, J=8.3 Hz, J=1.7 Hz, C$_q$CHCH (pyr.)); 8.49 (1H, dd, J=5.0 Hz, J=1.7 Hz, NCHCH (pyr.)) and 8.50 (1H, d, J=1.7 Hz, C$_q$CHN (pyr.));

$^{13}$C-NMR (75 MHz, CDCl$_3$) (ppm): 29.42 (CH); 31.12 (CH$_2$); 35.09 (C$_q$CH$_2$); 35.65 (C$_q$CH$_2$); 38.54 (NCH$_2$); 65.33

($\underline{C}_q$); 75.29 ($\underline{C}$HOH); 123.12 ($C_q$CH$\underline{C}$H (pyr.)); 134.37 ($C_q$$\underline{C}$HCH (pyr.)); 136.12 ($\underline{C}_q$ (pyr.)); 148.33 (N$\underline{C}$HCH (pyr.)) and 148.68 ($C_q\underline{C}$HN (pyr.));

IR (cm$^{-1}$): 1584, 1679 (pyrid.); 2927 (NH) and 3235 (OH); MS$^{ES}$ m/z (%): 205 (M+H$^+$, 100); 206 (15).

Example 5

Preparation and derivatisation of 2-R$_0$-2-azabicyclo[3.1.1]hept-1-yl)(pyridin-2-yl)methanone Ketones 12 were synthesised from 2-azabicyclo[3.1.1]heptyl-1-carbonitrile 5 as shown in scheme 5. Afterwards, refluxing ketone 12a (R$_0$=benzyl) with ammonium formate in the presence of Pd/C led to the complete removal of the benzyl group within 4 hours and compound 13a was recovered after crystallisation from diethyl ether.

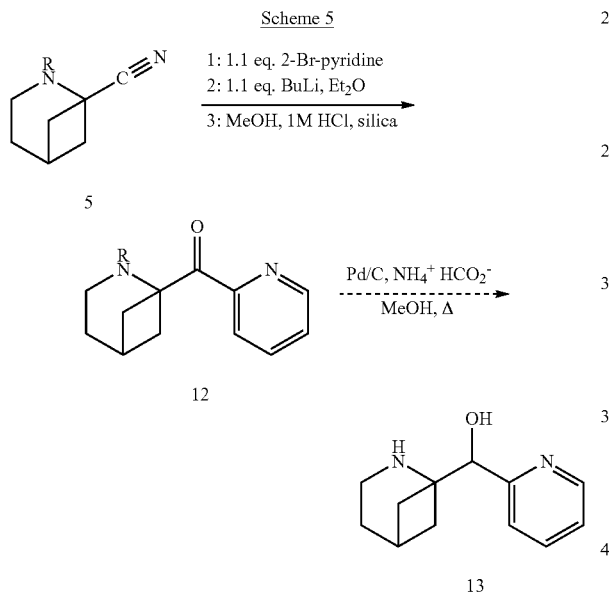

Scheme 5

Details of these syntheses are the same as for compounds 10 and 11 of example 4, except that 3-bromopyridine was replaced with 2-bromopyridine. The obtained derivatives were characterised by spectral data as follows:

Compound 12a (yield 68%)

$^1$H-NMR (300 MHz, CDCl$_3$) (ppm): 2.02 (2H, td, J=6.9 Hz, J=3.3 Hz, C$\underline{H}_2$); 2.32-2.41 (4H, m, 2×$C_q$C$\underline{H}_2$$\underline{H}_2$); 2.43-2.49 (1H, m, C$\underline{H}$); 3.00 (2H, t, J=6.9 Hz, NC$\underline{H}_2$); 3.53 (2H, s, NC$\underline{H}_2$Ph); 6.97-7.01 (2H, m, 2×C$\underline{H}$, Ph); 7.12-7.15 (3H, m, 3×C$\underline{H}$, Ph); 7.41 (1H, ddd, J=7.7 Hz, J=4.4 Hz, J=1.1 Hz, $C_q$CHCHC$\underline{H}$, pyr.); 7.80 (1H, td, J=7.7 Hz, J=1.7 Hz, $C_q$CHC$\underline{H}$, pyr.); 8.19 (1H, d, J=7.7 Hz, $C_q$C$\underline{H}$, pyr.); and 8.77 (1H, dd, J=4.4 Hz, J=1.1 Hz, NC$\underline{H}$, pyr.);

$^{13}$C-NMR (75 MHz, CDCl$_3$) (ppm): 28.66 ($\underline{C}$H$_2$); 29.22 ($\underline{C}$H); 35.10 (2×$C_q\underline{C}$H$_2$); 43.27 (N$\underline{C}$H$_2$); 56.63 (N$\underline{C}$H$_2$Ph); 73.90 ($\underline{C}_q$); 124.63 ($C_q\underline{C}$H, pyr.); 126.16 ($C_q$CHC$\underline{H}$, pyr.); 126.74 ($\underline{C}$H, Ph); 128.04 (2×$\underline{C}$H, Ph); 128.53 (2×$\underline{C}$H, Ph); 136.33 ($C_q\underline{C}$H, pyr.); 139.79 ($\underline{C}_q$, Ph); 149.57 (N$\underline{C}$H, pyr.); 153.29 ($\underline{C}_q$, pyr.); and 200.79 ($\underline{C}$=O);

IR (cm$^{-1}$): 1675 (C=O); and
MS$^{ES}$ m/z (%): 293 (M+H$^+$, 100); 294 (15).

Compound 12b (yield 70%)

$^1$H-NMR (300 MHz, CDCl$_3$) (ppm): 2.02 (2H, td, J=6.6 Hz, J=3.3 Hz, C$\underline{H}_2$); 2.30-2.40 (4H, m, 2×$C_q$C$\underline{H}_a\underline{H}_b$); 2.41-2.47 (1H, m, C$\underline{H}$); 2.99 (2H, t, J=6.6 Hz, NC$\underline{H}_2$); 3.47 (2H, s, NC$\underline{H}_2$Ph); 3.72 (3H, s, OC$\underline{H}_3$, Ph); 6.68 (2H, dt, J=8.5 Hz, J=2.2 Hz, 2×C$\underline{H}$, Ph); 6.89 (2H, d, J=8.5 Hz, 2×C$\underline{H}$, Ph); 7.41 (1H, ddd, J=7.7 Hz, J=4.4 Hz, J=1.1 Hz, $C_q$CHCHC$\underline{H}$, pyr.); 7.79 (1H, td, J=7.7 Hz, J=1.7 Hz, $C_q$CHC$\underline{H}$, pyr.); 8.17 (1H, dt, J=7.7 Hz, J=1.1 Hz, $C_q$C$\underline{H}$, pyr.); and 8.77 (1H, dt, J=4.4 Hz, J=1.7 Hz, NC$\underline{H}$, pyr.);

$^{13}$C-NMR (75 MHz, CDCl$_3$) (ppm): 28.69 ($\underline{C}$H$_2$); 29.22 ($\underline{C}$H); 35.10 (2×$C_q\underline{C}$H$_2$); 43.19 (N$\underline{C}$H$_2$); 55.18 (O$\underline{C}$H$_3$, Ph); 56.06 (N$\underline{C}$H$_2$Ph); 73.88 ($\underline{C}_q$); 113.43 (2×$\underline{C}$H, Ph); 124.62 ($C_q\underline{C}$H, pyr.); 126.15 ($C_q$CHC$\underline{H}$, pyr.); 129.67 (2×$\underline{C}$H, Ph); 131.76 ($\underline{C}_q$, Ph); 136.30 ($C_q\underline{C}$H, pyr.); 149.55 (N$\underline{C}$H, pyr.); 153.28 ($\underline{C}_q$, pyr.); 158.50 ($\underline{C}_q$, Ph); and 200.78 ($\underline{C}$=O);

IR (cm$^{-1}$): 1675 (C=O); and
MS$^{ES}$ m/z (%): 323 (M+H$^+$, 100); 324 (20).

Synthesis of Compound 13a

In a 50 ml flask 0.10 g (0.34 mmole) 2-benzyl-2-azabicyclo[3.1.1]hept-1-yl)(pyridin-2-yl)methanone 12a and 0.09 g (1.37 mmole) ammonium formate were dissolved in 20 ml methanol. To this solution 0.05 g (5% Pd) Pd/C was added and the suspension was refluxed 4 hours. The Pd/C catalyst was filtered off and methanol evaporated. 5 ml dichloromethane was added and the excess ammonium formate was filtered off. After evaporation of dichloromethane, compound 13a (yield 45%) was further purified by crystallisation from diethyl ether.

Example 6

Preparation of 2-R$_0$-2-azabicyclo[3.1.1]hept-1-ylmethyl)-pyridin-2-yl-amines

In a different approach, 2-substituted 2-azabicyclo[3.1.1]heptyl-1-carbonitriles 5 were converted to compounds 14 and 15 according to the scheme 6 below.

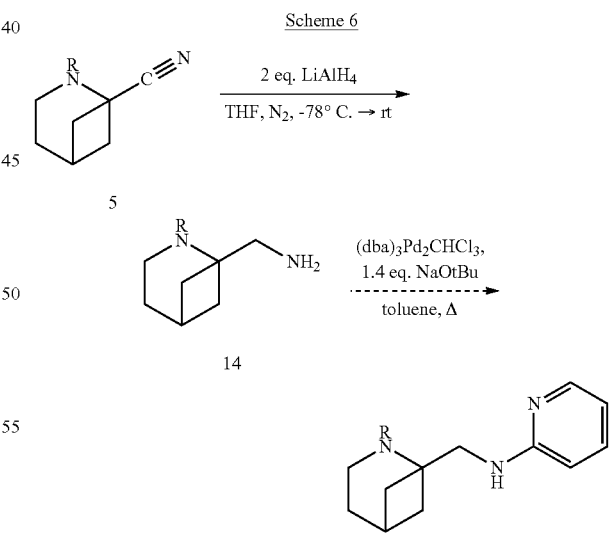

Scheme 6

Reduction of a nitrile compound 5 to an aminomethyl compound 14 by means of LiAlH$_4$ was performed quantitatively in most cases. Next, the pyridyl group was introduced onto the side chain of the 2-azabicyclo[3.1.1]hept-1-yl ring by means of a Pd catalysed cross-coupling reaction. The best results were obtained using 1 molar equivalent 2-bromopyridine, 1.4 molar equivalent sodium tert-butoxide and 8 mole % of a $(dba)_3Pd_2CHCl_3$ catalyst, wherein dba means dibenzylidene acetone.

Ligand requirements for this reaction proved to be highly dependent upon the substrate. Using 2-bromopyridine the ligand of choice was Binap, giving a conversion of 95% over 2 days. Using 3-bromopyridine and dfep as a ligand, a 55% conversion was obtained and the secondary amine 16 (shown in scheme 7 below) was isolated in 47% yield after column chromatography.

Details of these syntheses are as follows:

Synthesis of Compounds 14

In a dry 25 ml flask 0.11 g $LiAlH_4$ (3 mmole) was suspended in 10 ml dry THF (except for compound 14h where only 15 mmole, i.e. 0.06 g $LiAlH_4$, was used). The flask was placed under an inert $N_2$-atmosphere and cooled to −78° C. To this suspension, 1.5 mmole of a 2-R-2-azabicyclo[3.1.1]heptyl-1-carbonitrile 5, dissolved in 10 ml dry THF, was added dropwise. The cooling equipment was removed and the reaction mixture was allowed to heat up to room temperature. The reaction mixture was stirred overnight. Water was carefully added to neutralise the excess of $LiAlH_4$. The reaction mixture was dried by adding $MgSO_4$ and, after filtration of the solids and removal of the volatile components, the 2-R-2-azabicyclo[3.1.1]hept-1-yl)-methylamine 14 was obtained in quantitative yield. The obtained derivatives were characterised by proton ($^1$H-NMR) and carbon ($^{13}$C-NMR) nuclear magnetic resonance, mass spectrum ($MS^{ES}$) and infrared (IR) spectrophotometry as follows:

Compound 14a (yield 99%)
$^1$H-NMR (300 MHz, $CDCl_3$) (ppm): 1.65 (2H, td (+2 symm. side lines), J=6.6 Hz, J=2.8 Hz, (J=13.8 Hz from centre of signal), $C_qCH_aH_b$); 1.90 (2H, td, J=6.6 Hz, J=3.3 Hz, $CH_2$); 1.96 (2H, dd (+2 symm. side lines), J=6.6 Hz, J=2.8 Hz (J=12.4 Hz from centre of signal), $C_qCH_aH_b$); 2.43 (1H, septet, J=3.3 Hz, $CH$); 2.66 (2H, s, $C_qCH_2NH_2$); 2.94 (2H, t, J=6.6 Hz, $NCH_2$); 3.60 (2H, s, $NCH_2Ph$); and 7.20-7.37 (5H, m, 5×$CH$, Ph.);
$^{13}$C-NMR (75 MHz, $CDCl_3$) (ppm): 28.29 ($CH_2$); 30.03 ($CH$); 33.76 (2×$C_qCH_2$); 43.94 ($NCH_2$); 48.14 ($C_qCH_2NH_2$); 53.22 ($NCH_2Ph$); 68.14 ($C_q$); 126.60 ($CH$, Ph); 128.31 (4× $CH$, Ph); and 141.37 ($C_q$, Ph);
IR ($cm^{-1}$): 3265 ($NH_2$); and
$MS^{ES}$ m/z (%): 217 (M+H$^+$, 100).

Compound 14b (yield 97%)
$^1$H-NMR (300 MHz, $CDCl_3$) (ppm): 1.37 (2H, br. s, $NH_2$); 1.65 (2H, td (+2 symm. side lines), J=6.6 Hz, J=2.8 Hz, (J=12.9 Hz from centre of signal), 2×$C_qCH_aH_b$); 1.90 (2H, td, J=6.6 Hz, J=3.3 Hz, $CH_2$); 1.96 (2H, dd (+2 symm. side lines), J=6.6 Hz, J=2.8 Hz (J=11.0 Hz from centre of signal), 2×$C_qCH_aH_b$); 2.43 (1H, septet, J=3.3 Hz, $CH$); 2.66 (2H, s, $C_qCH_2NH_2$); 2.92 (2H, t, J=6.6 Hz, $NCH_2$); 3.53 (2H, s, $NCH_2Ph$); 3.80 (3H, s, $OCH_3$ (Ph)); 6.86 (2H, d, J=8.8 Hz, 2×$CH$ (Ph)); and 7.26 (2H, d, J=8.8 Hz, 2×$CH$ (Ph));
$^{13}$C-NMR (75 MHz, $CDCl_3$) (ppm): 28.42 ($CH_2$); 30.13 ($CH$); 33.84 (2×$C_qCH_2$); 43.77 ($NCH_2$); 48.33 ($C_qCH_2NH_2$); 52.64 ($NCH_2Ph$); 55.42 ($OCH_3$ (Ph)); 68.29 ($C_q$); 113.82 (2× $CH$ (Ph)); 129.54 (2×$CH$ (Ph)); 133.53 ($C_q$ (Ph)); and 158.51 ($C_q$ (Ph));
IR ($cm^{-1}$): 1684 (Ph) and 3365 ($NH_2$); and
$MS^{ES}$ m/z (%): 247 (M+H$^+$, 100).

Compound 14c (yield 99%)
$^1$H-NMR (300 MHz, $CDCl_3$) (ppm): 1.06 (6H, d, J=6.6 Hz, 2×$CH_3$ (iso-propyl)); 1.72-1.77 (4H, m, $C_qCH_aH_b$); 1.93 (2H, td, J=6.6 Hz, J=3.3 Hz, $CH_2$); 2.29-2.38 (1H, m, $CH$); 2.72 (2H, s, $C_qCH_2NH_2$); 3.03 (2H, t, J=6.6 Hz, $NCH_2$); and 3.19 (1H, septet, J=6.6 Hz, $CH$ (iso-propyl));
$^{13}$C-NMR (75 MHz, $CDCl_3$) (ppm): 20.29 (2×$CH_3$ (iso-propyl)); 29.59 ($CH$); 30.92 ($CH_2$); 36.69 ($NCH_2$); 36.77 (2×$C_qCH_2$); 47.50 ($CH$ (iso-propyl)); and 48.43 ($C_qCH_2NH_2$); 67.35 ($C_q$);
IR ($cm^{-1}$): 3362 ($NH_2$); and
$MS^{ES}$ m/z (%): 169 (M+H$^+$, 100); 170 (15); 186 (5).

Compound 14d (yield 99%)
$^1$H-NMR (300 MHz, $CDCl_3$) (ppm): 0.89 (3H, t, J=7.5 Hz, $CH_3$ (n-propyl)); 1.45 (2H, sextet, J=7.5 Hz, $CH_2$ (n-propyl)); 1.58 (2H, td (+2 symm. side lines), J=6.6 Hz, J=2.8 Hz (J=13.5 Hz from centre of signal), $C_qCH_aH_b$); 1.83 (2H, dd (+2 symm. side lines), J=6.6 Hz, J=2.8 Hz (J=10.5 Hz from centre of signal), $C_qCH_aH_b$); 1.87 (2H, td, J=6.6 Hz, J=3.3 Hz, $CH_2$); 2.33 (2H, t, J=7.5 Hz, $NCH_2$ (n-propyl)); 2.38 (1H, septet, J=3.3 Hz, $CH$); 2.55 (2H, s, $C_qCH_2NH_2$); and 3.00 (2H, t, J=6.6 Hz, $NCH_2$);
$^{13}$C-NMR (75 MHz, $CDCl_3$) (ppm): 11.92 ($CH_3$ (n-propyl)); 23.44 ($CH_2$ (n-propyl)); 28.52 ($CH_2$); 29.76 ($CH$); 33.67 (2×$C_qCH_2$); 44.41 ($NCH_2$); 48.28 ($C_qCH_2NH_2$); 51.80 ($NCH_2$ (n-propyl)); and 68.11 ($C_q$);
IR ($cm^{-1}$): 3368 ($NH_2$); and
$MS^{ES}$ m/z (%): 169 (M+H$^+$, 100); 170 (20).

Compound 14e (yield 93%)
$^1$H-NMR (300 MHz, $CDCl_3$) (ppm): 0.89 (6H, d, J=6.6 Hz, 2×$CH_3$ (iso-butyl)); 1.51-1.68 (3H, m, $CH$ (iso-butyl), $C_qCH_aH_b$); 1.81-1.88 (4H, m, $CH_2$, $C_qCH_aH_b$); 2.13 (2H, d, J=7.2 Hz, $CH_2$ (iso-butyl)); 2.37 (1H, septet, J=3.3 Hz, $CH$); 2.50 (2H, s, $C_qCH_2NH_2$); and 2.98 (2H, t, J=6.6 Hz, $NCH_2$);
$^{13}$C-NMR (75 MHz, $CDCl_3$) (ppm): 20.87 (2×$CH_3$ (iso-butyl)); 28.31 ($CH_2$); 28.55 ($CH$ (iso-butyl)); 29.76 ($CH$); 33.64 (2×$C_qCH_2$); 44.87 ($NCH_2$); 48.23 ($C_qCH_2NH_2$); 58.26 ($NCH_2$ (iso-butyl)); and 68.19 ($C_q$);
IR ($cm^{-1}$): 3366 ($NH_2$); and
$MS^{ES}$ m/z (%): 183 (M+H$^+$, 100); 184 (15); 211 (5).

Compound 14f (yield 98%)
$^1$H-NMR (300 MHz, $CDCl_3$) (ppm): 0.91 (3H, t, J=7.2 Hz, $CH_3$ (n-butyl)); 1.25-1.47 (4H, m, 2×$CH_2$ (n-butyl)); 1.58 (2H, td (+2 symm. side lines), J=6.6 Hz, J=2.8 Hz (J=14.0 Hz from centre of signal), $C_qCH_aH_b$); 1.71 (2H, s, $NH_2$); 1.83 (2H, dd (+2 symm. side lines), J=6.6 Hz, J=2.8 Hz (J=10.7 Hz from centre of signal), $C_qCH_aH_b$); 1.87 (2H, td, J=6.6 Hz, J=3.3 Hz, $CH_2$); 2.36 (2H, t, J=7.2 Hz, $NCH_2$ (n-butyl)); 2.37 (1H, septet, J=3.3 Hz, $CH$); 2.55 (2H, s, $C_qCH_2NH_2$); and 3.00 (2H, t, J=6.6 Hz, $NCH_2$);
$^{13}$C-NMR (75 MHz, $CDCl_3$) (ppm): 14.18 ($CH_3$ (n-butyl)); 20.70 ($CH_2CH_3$ (n-butyl)); 28.52 ($CH_2$); 29.77 ($CH$); 32.69 ($CH_2CH_2$ (n-butyl)); 33.68 (2×$C_qCH_2$); 44.37 ($NCH_2$); 48.20 ($C_qCH_2NH_2$); 49.59 ($NCH_2$ (iso-butyl)); and 68.11 ($C_q$);
IR ($cm^{-1}$): 3364 ($NH_2$); and
$MS^{ES}$ m/z (%): 183 (M+H$^+$, 100); 184 (15).

Compound 14q (yield 93%)
$^1$H-NMR (300 MHz, $CDCl_3$) (ppm): 1.25 (2H, br. s, $NH_2$); 1.61-1.71 (2H, m, 2×$C_qCH_aH_b$); 1.89 (2H, td, J=6.6 Hz, J=3.3 Hz, $CH_2$); 1.96 (2H, dd (+2 symm. side lines), J=7.2 Hz, J=2.8 Hz (J=10.5 Hz from centre of signal), 2×$C_qCH_aH_b$); 2.33 (3H, s, $CH_3$ (Ph)); 2.43 (1H, septet, J=3.3 Hz, $CH$); 2.66 (2H, s, $C_qCH_2NH_2$); 2.93 (2H, t, J=6.6 Hz, $NCH_2$); 3.56 (2H, s, $NCH_2Ph$); 7.13 (2H, d, J=8.3 Hz, 2×$CH$ (Ph)); and 7.24 (2H, d, J=8.3 Hz, 2×$CH$ (Ph));
$^{13}$C-NMR (75 MHz, $CDCl_3$) (ppm): 21.67 ($CH_3$ (Ph)); 28.22 ($CH_2$); 30.02 ($CH$); 33.73 (2×$C_qCH_2$); 43.80 ($NCH_2$); 47.88 ($C_qCH_2NH_2$); 52.87 ($NCH_2Ph$); 67.97 ($C_q$); 128.28 (2×$CH$ (Ph)); 129.02 (2×$CH$ (Ph)); 136.21 ($C_q$ Ph); 138.05 ($C_q$ (Ph));

IR □ (cm$^{-1}$): 1457, 1514 (Ph); and 3276 (NH$_2$);
MS$^{ES}$ m/z (%): 231 (M+H$^+$, 100); 232 (15).

Compound 14h (yield 87%)

$^1$H-NMR (300 MHz, CDCl$_3$) (ppm): 1.68 (2H, td (+2 symm. side lines), J=7.2 Hz, J=2.8 Hz (J=13.5 Hz from centre of signal), C$_q$CH$_a$H$_b$); 1.94 (2H, td, J=6.6 Hz, J=3.3 Hz, CH$_2$); 1.98 (2H, dd (+2 symm. side lines), J=7.2 Hz, J=2.8 Hz (J=11.0 Hz from centre of signal), C$_q$CH$_a$H$_b$); 2.29 (2H, s, NH$_2$); 2.45 (1H, septet, J=3.3 Hz, CH); 2.67 (2H, s, C$_q$CH$_2$NH$_2$); 3.01 (2H, t, J=6.6 Hz, NCH$_2$); 3.76 (2H, s, NCH$_2$pyr.); 7.15 (1H, dd, J=7.7 Hz, J=5.0 Hz, NCHCH, pyr.); 7.49 (1H, d, J=7.7 Hz, C$_q$CH, pyr.); 7.67 (1H, td, J=7.7 Hz, J=1.7 Hz, C$_q$CHCH, pyr.); and 8.52 (1H, d, J=5.0 Hz, NCH, pyr.);

$^{13}$C-NMR (75 MHz, CDCl$_3$) (ppm): 28.31 (CH$_2$); 29.99 (CH); 33.88 (2×C$_q$CH$_2$); 44.84 (NCH$_2$); 48.02 (C$_q$CH$_2$NH$_2$); 55.67 (NCH$_2$pyr.); 68.05 (C$_q$); 121.72 (NCHCH, pyr.); 122.31 (C$_q$CH, pyr.); 136.66 (C$_q$CHCH, pyr.); and 149.08 (NCH, pyr.); 161.52 (C$_q$, pyr.);

IR (cm$^{-1}$): 3368 (NH$_2$); and
MS$^{ES}$ m/z (%): 218 (M+H$^+$, 100).

Compound 14k (yield 98%)

$^1$H-NMR (300 MHz, CDCl$_3$) (ppm): 1.61 (2H, td (+2 symm. side lines), J=6.3 Hz, J=2.8 Hz (J=13.2 Hz from centre of signal), C$_q$CH$_a$H$_b$); 1.67 (2H, br. s, NH$_2$); 1.91 (2H, td, J=6.6 Hz, J=3.3 Hz, CH$_2$); 1.98 (2H, dd (+2 symm. side lines), J=7.2 Hz, J=2.8 Hz (J=12.1 Hz from centre of signal), C$_q$CH$_a$H$_b$); 2.42 (1H, septet, J=3.3 Hz, CH); 2.67 (2H, s, C$_q$CH$_2$NH$_2$); 2.96 (2H, t, J=6.6 Hz, NCH$_2$); 3.51 (2H, s, NCH$_2$Ph); 3.78 (3H, s, OCH$_3$, Ph); 3.81 (3H, s, OCH$_3$, Ph); 6.44-6.48 (2H, m, C$_q$CHC$_q$, C$_q$CHCH, Ph); and 7.24-7.28 (1H, m, C$_q$CHCH, Ph);

$^{13}$C-NMR (75 MHz, CDCl$_3$) (ppm): 28.41 (CH$_2$); 30.02 (CH); 33.88 (2×C$_q$CH$_2$); 43.62 (NCH$_2$); 47.42 (NCH$_2$Ph); 48.52 (C$_q$CH$_2$NH$_2$); 55.26 (OCH$_3$, Ph); 55.39 (OCH$_3$, Ph); 68.49 (C$_1$); 98.59 (C$_q$CHC$_q$, Ph); 103.82 (C$_q$CHCH, Ph); 121.63 (C$_q$, Ph); 130.59 (C$_q$CHCH, Ph); 158.56 (C$_q$, Ph); and 159.89 (C$_q$, Ph);

IR (cm$^{-1}$): 3360 (NH$_2$); and
MS$^{ES}$ m/z (%): 277 (M+H$^+$, 100); 278 (M+2$^+$, 10).

Compound 14m (yield 99%)

$^1$H-NMR (300 MHz, CDCl$_3$) (ppm): 1.07 (3H, t, J=7.2 Hz, CH$_3$ (ethyl)); 1.40 (2H, br. s, NH$_2$); 1.61 (2H, td (+2 symm. side lines), J=6.6 Hz, J=2.8 Hz (J=12.9 Hz from centre of signal), 2×C$_q$CH$_a$H$_b$); 1.82 (2H, dd (+2 symm. side lines), J=6.6 Hz, J=2.8 Hz (J=10.5 Hz from centre of signal), 2×C$_q$CH$_a$H$_b$); 1.89 (2H, td, J=6.6 Hz, J=3.3 Hz, CH$_2$); 2.38 (1H, ~septet, J=3.3 Hz, CH); 2.44 (2H, q, J=7.2 Hz, NCH$_2$ (ethyl)); 2.58 (2H, s, C$_q$CH$_2$NH$_2$); and 3.01 (2H, t, J=6.6 Hz, NCH$_2$);

$^{13}$C-NMR (75 MHz, CDCl$_3$) (ppm): 15.38 (CH$_3$ (ethyl)) 28.63 (CH$_2$); 29.68 (CH); 33.67 (2×C$_q$CH$_2$); 43.54 (NCH$_2$ (ethyl)); 43.77 (NCH$_2$); 48.25 (C$_q$CH$_2$NH$_2$); and 68.11 (C$_q$);

IR (cm$^{-1}$): 3307 (NH$_2$); and
MS$^{ES}$ m/z (%): 155 (M+H$^+$, 100); 156 (10).

Compound 14n (yield 99%)

$^1$H-NMR (300 MHz, CDCl$_3$) (ppm): 0.89 (3H, t, J=7.5 Hz, CH$_3$ (n-propyl)); 1.45 (2H, sextet, J=7.5 Hz, CH$_2$ (n-propyl)); 1.58 (2H, td (+2 symm. side lines), J=6.6 Hz, J=2.8 Hz (J=13.5 Hz from centre of signal), C$_q$CH$_a$H$_b$); 1.83 (2H, dd (+2 symm. side lines), J=6.6 Hz, J=2.8 Hz (J=10.5 Hz from centre of signal), C$_q$CH$_a$H$_b$); 1.87 (2H, td, J=6.6 Hz, J=3.3 Hz, CH$_2$); 2.33 (2H, t, J=7.5 Hz, NCH$_2$ (n-propyl)); 2.38 (1H, septet, J=3.3 Hz, CH); 2.55 (2H, s, C$_q$CH$_2$NH$_2$); and 3.00 (2H, t, J=6.6 Hz, NCH$_2$);

$^{13}$C-NMR (75 MHz, CDCl$_3$) (ppm): 29.44 (CH$_2$); 30.05 (CH); 33.10 (2×C$_q$CH$_2$); 38.16 (NCH$_3$); 47.96 (C$_q$CH$_2$NH$_2$); 48.67 (NCH$_2$); and 67.30 (C$_q$);

IR (cm$^{-1}$): 3361 (NH$_2$); and
MS$^{ES}$ m/z (%): 141 (M+H$^+$, 100); 142 (10).

Synthesis of Compound 15a

In a dry tube 0.66 g (3 mmole) of 2-benzyl-2-azabicyclo [3.1.1]hept-1-yl)-methylamine 14a, 0.47 g (3 mmole) 2-bromopyridine and 0.41 g (4.2 mmole) sodium tert-butoxide were dissolved in 25 ml dry toluene. The tube was flushed with argon and 124 mg (0.12 mmole, 8 mole % Pd) of a catalyst (dba)$_3$Pd$_2$CHCl$_3$ and 149 mg (0.24 mmole, 8 mole %) Binap were added. The tube was flushed a second time with argon, closed and heated to 70° C. 50 hours later the reaction was ended by filtration of the Pd-catalyst. Toluene was removed under vacuum and the residue was re-dissolved in dichloromethane. A saturated NaHCO$_3$ solution was added and extracted twice with dichloromethane. The combined organic phases were dried over MgSO$_4$ and evaporated.

Synthesis of Compound 16a

Synthesis proceeded by analogy to compound 15a, except that t-butyl-{1-[2-(dicyclohexylphosphanyl)ferrocenyl]ethyl}phosphine (dfep) was used as a ligand and 3-bromopyridine used instead of 2-bromopyridine. Purification was performed by means of column chromatography.

Example 7

Preparation of 2-azabicyclo[3.1.1]hept-1-ylmethyl)-pyridinyl-amines

Removal of the protective benzyl group was performed, by refluxing in methanol, using ammonium formate as reducing agent, as shown in scheme 7 below. Compound 17 was obtained after 1 hour of reflux, while for compound 18 a period of 2 hours was necessary to drive the reaction to completion. Compound 17 was easily separated from the excess ammonium formate by dissolution in dry diethyl ether. Compound 18 however does not dissolve in diethyl ether. Eventually, separation of the ammonium salts was obtained by a temperature controlled selective crystallisation from hexane.

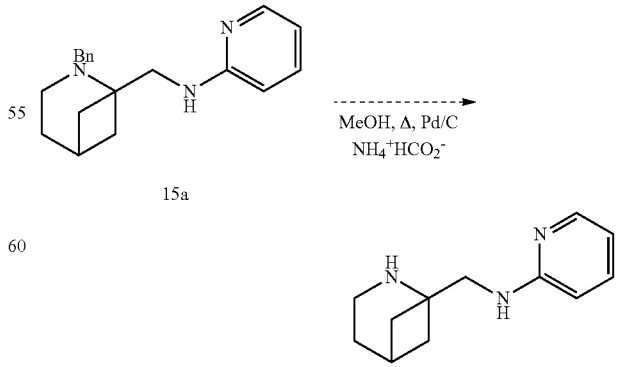

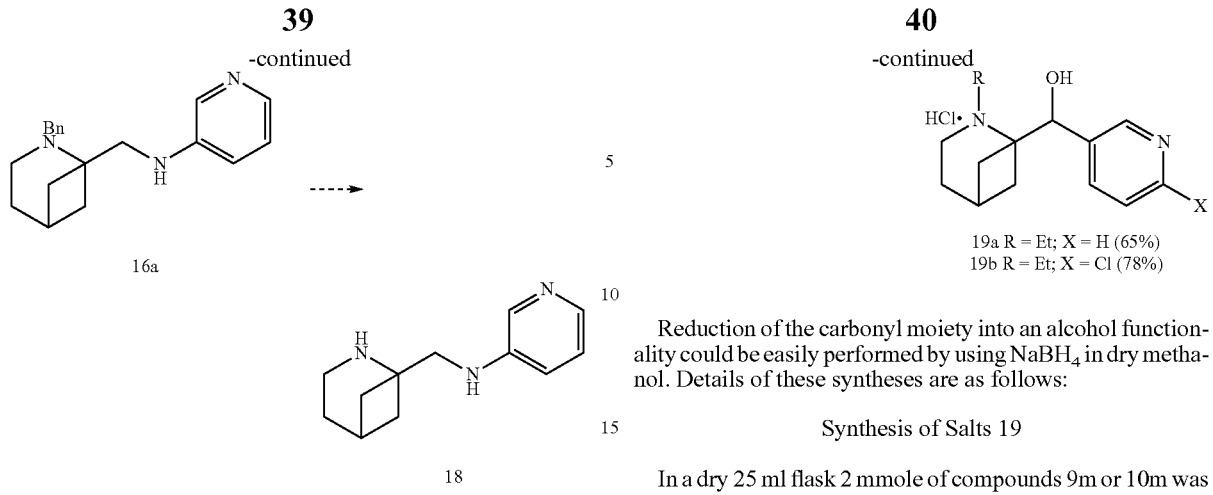

16a

18

Details of these syntheses are as follows:

Synthesis of Compound 17

In a 50 ml flask 0.67 g (2.3 mmole) 2-benzyl-2-azabicyclo[3.1.1]hept-1-ylmethyl)-pyridin-2-yl-amine 15a and 0.66 g (10.6 mmole) ammonium formate were dissolved in 40 ml methanol. To this solution 0.34 g of a Pd/C catalyst (5% Pd) was added. The suspension was refluxed during one hour, after which the Pd/C catalyst was filtered off and the methanol evaporated.

Synthesis of Compound 18

0.18 g (0.61 mmole) 2-benzyl-2-azabicyclo[3.1.1]hept-1-ylmethyl)pyridin-3-ylamine 16a and 0.15 g (2.45 mmole) ammonium formate were dissolved in 20 ml methanol. To this solution 0.09 g of a Pd/C catalyst (5% Pd) was added. The suspension was refluxed during 2 hours after which the Pd/C catalyst was removed by filtration and methanol was evaporated. The solid residue was treated with boiling hexane, decanted and cooled to −20° C. Crystals of compound 18 were obtained.

Example 8

Preparation of salts of 2-R₀-2-azabicyclo[3.1.1]hept-1-yl-pyridinylmethanol derivatives 2-substituted 2-azabicyclo[3.1.1]hept-1-yl-pyridinylmethanone derivatives 9m and 10m were converted to the acid salts 19 according to the scheme 8 below.

Scheme 8

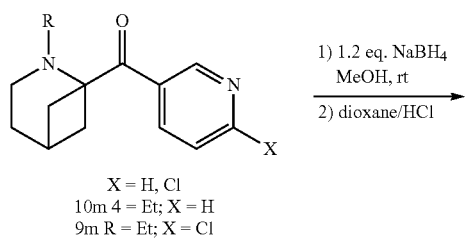

X = H, Cl
10m 4 = Et; X = H
9m R = Et; X = Cl 1) 1.2 eq. NaBH₄ MeOH, rt
2) dioxane/HCl 19a R = Et; X = H (65%)
19b R = Et; X = Cl (78%)

Reduction of the carbonyl moiety into an alcohol functionality could be easily performed by using NaBH₄ in dry methanol. Details of these syntheses are as follows:

Synthesis of Salts 19

In a dry 25 ml flask 2 mmole of compounds 9m or 10m was dissolved in 15 mL dry methanol. The flask was placed under an inert $N_2$-atmosphere and stirred at room temperature. To this solution, 90.8 mg (2.4 mmole) NaBH₄ was added. The reaction mixture was stirred overnight. Water was carefully added to neutralise the excess of NaBH₄. Extraction was performed with water and diethyl ether. The organic phase was dried by adding MgSO₄ and, after filtration of the solids and removal of the volatile components, the crude alcohol was obtained in quantitative yield. The residue was dissolved in dry diethyl ether and 0.5 ml of a 4 M HCl solution in dioxane was added. The compounds 19 were isolated as the hydrochloric salt in good yields. The obtained derivatives were characterised by proton ($^1$H-NMR) and carbon ($^{13}$C-NMR) nuclear magnetic resonance, mass spectrum ($MS^{ES}$) and infrared (IR) spectrophotometry as follows:

Compound 19a (yield 65%)

$^1$H-NMR (300 MHz, D₂O, CH₃CN) (ppm): 1.45 (3H, t, J=7.2 Hz, C$\underline{H}_3$ (ethyl)); 1.76-1.85 (1H, m, $C_q$C$\underline{H}_a$H$_b$); 1.87-2.05 (3H, m, $C_q$CH$_a$$\underline{H}_b$, $C_q$CH$_a$$\underline{H}_b$); 2.07-2.27 (2H, m, C$\underline{H}_2$); 2.41 (1H, ~septet, J=3.3 Hz, C$\underline{H}$); 2.54 (1H, br. s, O$\underline{H}$); 3.38 (1H, dq, J=13.8 Hz, J=7.2 Hz, NC$\underline{H}_a$H$_b$ (ethyl)); 3.49-3.70 (2H, m, NCH$_a$$\underline{H}_b$ (ethyl), NC$\underline{H}_a$H$_b$); 3.83 (1H, dt, J=13.8 Hz, J=7.2 Hz, NCH$_a$$\underline{H}_b$); 5.30 (H, s, C$\underline{H}$OH); 7.84 (1H, dd, J=8.3 Hz, J=5.0 Hz, $C_q$C$\underline{H}$CH (pyr.)); 8.26 (1H, ~d, J=8.3 Hz, $C_q$C$\underline{H}$CH (pyr.)); 8.69 (1H, d, J=7.7 Hz, NC$\underline{H}$CH (pyr.)) and 8.71 (1H, s, $C_q$C$\underline{H}$N (pyr.));

$^{13}$C-NMR (75 MHz, D₂O, CH₃CN) (ppm): 10.63 ($\underline{C}$H₃ (ethyl)); 25.38 ($\underline{C}$H₂); 29.18 ($C_q$$\underline{C}$H₂); 29.35 ($\underline{C}$H); 30.01 ($C_q$$\underline{C}$H₂); 46.47 (N$\underline{C}$H₂); 47.11 (N$\underline{C}$H₂ (ethyl)); 69.06 ($\underline{C}$HOH); 74.62 ($C_q$); 126.27 ($C_q$CH$\underline{C}$H (pyr.)); 137.78 ($C_q$, pyr.); 141.77 ($C_q$$\underline{C}$HCH (pyr.)); 144.87 ($C_q$$\underline{C}$HN, pyr.); and 145.85 (N$\underline{C}$HCH, pyr.);

IR (cm$^{-1}$): 1636 (pyr.); 3358 (OH); and $MS^{ES}$ m/z (%): 233 (M+H⁺, 100); 234 (15).

Compound 19b (yield 78%)

$^1$H-NMR (300 MHz, D₂O, CH₃CN) (ppm): 1.43 (3H, t, J=7.2 Hz, C$\underline{H}_3$ (ethyl)); 1.74-2.25 (6H, m, 2×$C_q$C$\underline{H}_a$H$_b$, C$\underline{H}_2$); 2.40 (1H, br. s, C$\underline{H}$); 2.54 (1H, br. s, O$\underline{H}$); 3.38 (1H, dq, J=13.8 Hz, J=7.2 Hz, NC$\underline{H}_a$H$_b$ (ethyl)); 3.46-3.66 (2H, m, NCH$_a$$\underline{H}_b$ (ethyl), NC$\underline{H}_a$H$_b$); 3.81 (1H, dt, J=13.8 Hz, J=7.2 Hz, NCH$_a$$\underline{H}_b$); 5.18 (H, s, C$\underline{H}$OH); 7.59 (1H, d, J=8.3 Hz, $C_q$CHC$\underline{H}$ (pyr.)); 7.88 (1H, d, J=8.3 Hz, $C_q$C$\underline{H}$CH (pyr.)); and 8.35 (1H, s, $C_q$C$\underline{H}$N (pyr.));

$^{13}$C-NMR (75 MHz, D₂O, CH₃CN) (ppm): 10.65 ($\underline{C}$H₃ (ethyl)); 25.40 ($\underline{C}$H₂); 29.23 ($C_q$$\underline{C}$H₂, $\underline{C}$H); 29.95 ($C_q$$\underline{C}$H₂); 46.45 (N$\underline{C}$H₂); 47.08 (N$\underline{C}$H₂ (ethyl)); 69.00 ($\underline{C}$HOH); 74.80 ($C_q$); 125.31 ($C_q$CH$\underline{C}$H, pyr.); 134.64 ($C_q$, pyr.); 140.14 ($C_q$$\underline{C}$HCH (pyr.)); 148.85 ($C_q$$\underline{C}$HN (pyr.)); and 151.22 ($C_q$Cl, pyr.);

IR (cm$^{-1}$): 1458, 1647 (pyr.); 3348 (OH); and $MS^{ES}$ m/z (%): 267 (M+H⁺, 100); 269 (M+H⁺, 35); 270 (10).

Example 9

Preparation of Hydrochloric Salts

Compound 14h described in example 6 was easily converted to its hydrochloric salt 20, using a 4 M HCl solution in dioxane as shown in scheme 9 below.

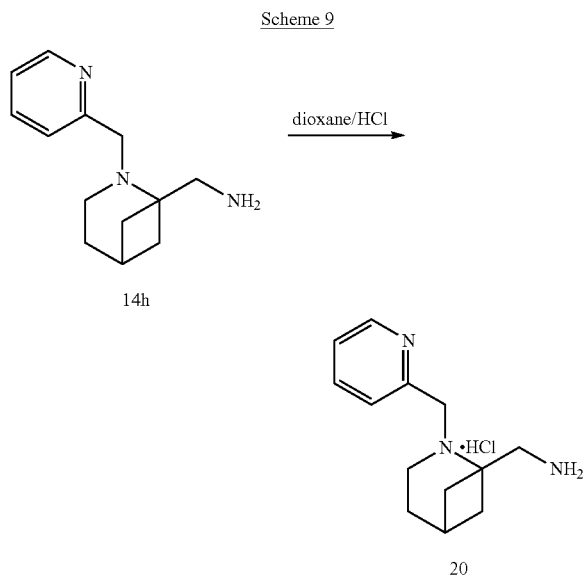

Compound 14h (2 mmole, 0.43 g) was dissolved in dry diethyl ether and 0.5 ml of a 4 M HCl solution in dioxane was added. The formed hydrochloric salt 20 was filtered off (yield 92%) and characterised by proton ($^1$H-NMR) and carbon ($^{13}$C-NMR) nuclear magnetic resonance, mass spectrum (MS$^{ES}$) and infrared (IR) spectrophotometry as follows:

$^1$H-NMR (300 MHz, D$_2$O, CH$_3$CN) (ppm): 2.18 (2H, td, J=7.4 Hz, J=3.3 Hz, C$\underline{H}_2$); 2.21 (2H, dd (+2 symm. side lines), J=8.8 Hz, J=2.8 Hz (J=11.8 Hz from centre of signal), 2×C$_q$C $\underline{H}_a$H$_b$); 2.33 (2H, dd (+2 symm. side lines), J=8.8 Hz, J=2.8 Hz (J=15.7 Hz from centre of signal), 2×C$_q$CH$_a\underline{H}_b$); 2.68 (1H, septet, J=3.3 Hz, C$\underline{H}$); 3.40 (2H, s, C$_q$C$\underline{H}_2$NH$_2$); 3.42 (2H, t, J=6.6 Hz, NC$\underline{H}_2$); 4.55 (2H, s, NC$\underline{H}_2$pyr.); 7.69 (1H, dd, J=7.7 Hz, J=5.7 Hz, NCHC$\underline{H}$ (pyr.)); 7.75 (1H, d, J=7.7 Hz, C$_q$C$\underline{H}$ (pyr.)); 8.18 (1H, td, J=7.7 Hz, J=1.7 Hz, C$_q$CHC$\underline{H}$ (pyr.)); and 8.67 (1H, dd, J=5.7 Hz, J=1.7 Hz, NC$\underline{H}$ (pyr.));

$^{13}$C-NMR (75 MHz, D$_2$O, CH$_3$CN) (ppm): 25.17 (C$\underline{H}_2$); 29.35 (C$\underline{H}$); 32.77 (2×C$_q\underline{C}$H$_2$); 42.85 (C$_q\underline{C}$H$_2$NH$_2$); 47.21 (N$\underline{C}$H$_2$); 54.45 (N$\underline{C}$H$_2$pyr.); 68.56 ($\underline{C}_q$); 125.87 (NCH$\underline{C}$H (pyr.)); 126.12 (C$_q\underline{C}$H (pyr.)); 142.36 (C$_q$CH$\underline{C}$H (pyr.)); 146.85 (N$\underline{C}$H (pyr.)); 151.60 ($\underline{C}_q$ (pyr.));

IR (cm$^{-1}$): 1639 (pyr.); and 3338 (NH$_2$);

MS$^{ES}$ m/z (%): 218 (M+H$^+$, 80); 219 (100); 220 (30); 221 (5).

Example 10

Competitive Enzyme Binding Assays of Compounds Wherein R$_0$ is Hydrogen or Alkyl or Aryl at Relatively Low Concentrations Four illustrative compounds of this invention have each been tested at a concentration of 1 µmmole in a series of 6 binding assays for various enzymes, including dopaminic receptors, neuronal nicotinic receptors and muscular nicotinic receptors. Details of each binding assay procedure are given below.

Human Dopamine D$_1$ Receptor (Antagonist Radioligand):

The purpose is to evaluate the affinity of compounds for the human dopamine D$_1$ receptor in transfected CHO cells determined in a radioligand binding assay according to Zhou et al in *Nature* (1990) 347:76. The experimental protocol is as follows. Cell membrane homogenates (48 µg protein) are incubated for 60 minutes at 22° C. with 0.3 nM [$^3$H]SCH 23390 in the absence or presence of the test compound in a buffer containing 50 mM Tris-HCl (pH 7.4), 5 mM KCl, 5 mM MgCl$_2$, 1.5 mM CaCl$_2$ and 5 mM EDTA. Non-specific binding is determined in the presence of 1 µM SCH 23390. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is SCH 23390, which is tested in each experiment at several concentrations to obtain a competition curve from which its IC$_{50}$ is calculated, and from which the % inhibition at 1 µM as indicated in the following table is obtained.

Human Dopamine D$_5$ Receptor (Antagonist Radioligand):

The purpose is to evaluate the affinity of compounds for the human dopamine D$_1$ receptor in transfected GH4 cells determined in a radioligand binding assay according to Sunahara et al in *Nature* (1991) 350:614. The experimental protocol is as follows. Cell membrane homogenates (20 µg protein) are incubated for 60 minutes at 22° C. with 0.3 nM [$^3$H]SCH 23390 in the absence or presence of the test compound in a buffer containing 50 mM Tris-HCl (pH 7.4), 120 mM NaCl, 5 mM KCl, 5 mM MgCl$_2$ and 1 mM EDTA. Nonspecific binding is determined in the presence of 10 µM SCH 23390. Following incubation, the samples are filtered rapidly under vacuum through glass fiber filters (GF/B, Packard) 63re-soaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is SCH 23390, which is tested in each experiment at several concentrations to obtain a competition curve from which its IC$_{50}$ is calculated, and from which the % inhibition at 1 µM as indicated in the following table is obtained.

Human Dopamine D$_5$ Receptor (Agonist Radioligand):

The purpose is to evaluate the affinity of compounds for the agonist site of the human dopamine D$_5$ receptor in transfected GH4 cells determined in a radioligand binding assay according to Sunahara et al in *Nature* (1991) 350:614. The experimental protocol is as follows. Cell membrane homogenates (120 µg protein) are incubated for 60 minutes at 22° C. with 7.5 nM [$^3$H]dopamine in the absence or presence of the test compound in a buffer containing 20 mM Tris-HCl (pH 7.4), 5 mM MgCl$_2$, 0.8 mM DTT, 0.3 mM ascorbic acid and 0.1 mM pyrocatechol. Nonspecific binding is determined in the presence of 10 µM SCH 23390. Following incubation, the samples are filtered rapidly under vacuum through glass fiber filters (GF/B, Packard) 64re-soaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is dopamine, which is tested in each experiment at several concentrations to obtain a competition curve from which its $IC_{50}$ is calculated, and from which the % inhibition at 1 μM as indicated in the following table is obtained.

Neuronal Nicotinic Receptor (α-BGTX-Insensitive) (Agonist Radioligand):

The purpose is to evaluate the affinity of compounds for the human α4β2 neuronal nicotinic receptor expressed in transfected SH-SY5Y cells, determined in a radioligand binding assay according to Gopalakrishnan et al in *J. Pharmacol. Exp. Ther.* (1996) 276:289. The experimental protocol is as follows. Cell membrane homogenates (30 μg protein) are incubated for 120 min at 4° C. with 0.6 nM [$^3$H]cytisine in the absence or presence of the test compound in a buffer containing 50 mM Tris-HCl (pH 7.4), 120 mM NaCl, 5 mM KCl, 2.5 mM $CaCl_2$ and 1 mM $MgCl_2$. Nonspecific binding is determined in the presence of 10 μM nicotine bitartrate. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is nicotine bitartrate, which is tested in each experiment at several concentrations to obtain a competition curve from which its $IC_{50}$ is calculated, and from which the % inhibition at 1 μM as indicated in the following table is obtained.

Neuronal Nicotinic Receptor (α-BGTX-Sensitive)

The purpose is to evaluate the affinity of compounds for the human α7 neuronal nicotinic receptor expressed in transfected SH-SY5Y cells, determined in a radioligand binding assay according to Sharples et al in *J. Neurosci.* (2000) 20:2783. The experimental protocol is as follows. Cell membrane homogenates (20 μg protein) are incubated for 120 min at 37° C. with 0.05 nM [$^{125}$I]α-bungarotoxin in the absence or presence of the test compound in a buffer containing 50 mM $K_2HPO_4/KH_2PO_4$ (pH 7.4), 10 mM $MgCl_2$ and 0.1% BSA. Nonspecific binding is determined in the presence of 1 μM α-bungarotoxin. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is α-bungarotoxin, which is tested in each experiment at several concentrations to obtain a competition curve from which its $IC_{50}$ is calculated, and from which the % inhibition at 1 μM as indicated in the following table is obtained.

Human Muscle-Type Nicotinic Receptor

The purpose is to evaluate the affinity of compounds for the human muscle-type nicotinic receptor expressed in TE671 cells determined in a radioligand binding assay according to Lukas in *J. Neurochem.* (1986) 46:1936. The experimental protocol is as follows. Cell membrane homogenates (60 μg protein) are incubated for 120 minutes at 22° C. with 0.5 nM [$^{125}$I]α-bungarotoxin in the absence or presence of the test compound in a buffer containing 20 mM Hepes/NaOH (pH 7.3), 118 mM NaCl, 4.8 mM KCl, 2.5 mM $CaCl_2$, 1.2 mM $MgSO_4$ and 0.1% BSA. Nonspecific binding is determined in the presence of 5 μM α-bungarotoxin. Following incubation, the samples are filtered rapidly under vacuum through glass fiber filters (GF/B, Packard) 65re-soaked with 0.3% PEI and rinsed several times with an ice-cold buffer containing 50 mM Tris-HCl, 150 mM NaCl and 0.1% BSA using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is α-bungarotoxin, which is tested in each experiment at several concentrations to obtain a competition curve from which its $IC_{50}$ is calculated, and from which the % inhibition at 1 μM as indicated in the following table is obtained.

The formulae of the four tested compounds and the results of these six binding assays are reported in the table below, wherein each value represents one single experiment.

TABLE

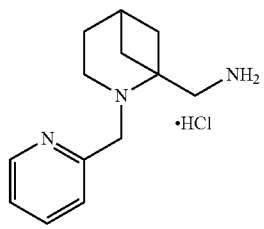 [SMILES: NCC12CC(CCN1Cc1ccccn1)C2 ; Cl]

20

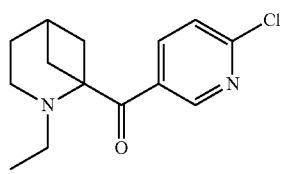 [SMILES: CCN1CCC2CC1(C(=O)c1ccc(Cl)nc1)C2]

9m

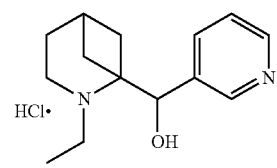

19a

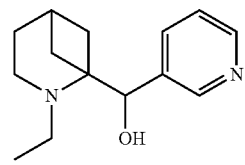 [SMILES: CCN1CCC2CC1(C(O)c1cccnc1)C2]

11

| receptor | % inhibition | | | |
|---|---|---|---|---|
| | Comp. 20 | Comp. 9m | Comp. 19a | Comp. 11 |
| D1 (h) (antagonist radioligand) | −3 | 8 | 9 | 22 |
| D5 (h) (antagonist radioligand) | 31 | 17 | 2 | 2 |
| D5 (h) (agonist radioligand) | 6 | −13 | −2 | −6 |

TABLE-continued

| | | | | |
|---|---|---|---|---|
| N neuronal alpha-BGTX-insensitive (alpha4beta 2) (agonist radioligand) | 11 | 4 | 24 | −5 |
| N neuronal alpha-BGTX-sensitive (alpha 7) (antagonist radioligand) | 12 | −1 | 3 | −1 |
| N muscle-type (h) (antagonist radioligand) | 32 | −8 | 33 | 17 |

The above data show that the tested compounds actually bind selected receptors such as alpha-4-beta-2 and muscular type neuronal nicotinic receptor together with the D5 receptor. Also, small changes in the substituting pattern largely influence activity and selectivity.

Example 11

Competitive Enzyme Binding Assays of Compounds Wherein $R_0$ is Hydrogen or Alkyl or Aryl at Relatively High Concentrations Illustrative compounds of this invention are also tested at a concentration of 5 μmoles in the same series of 6 binding assays as in example 10.

Example 12

Other Relevant Competitive Enzyme Binding Assays

Compounds of this invention may also be tested for activity, in particular selectivity, in one or more of the following binding assays, for instance at concentrations of 1 μmole or 5 μmoles. Details of each binding assay procedure are given below.

Human Dopamine $D_3$ Receptor (Antagonist Radioligand):

The purpose is to evaluate the affinity of compounds for the human dopamine $D_3$ receptor in transfected CHO cells determined in a radioligand binding assay according to Mackenzie et al in *Eur. J. Pharmacol.* (1994) 266:79. The experimental protocol is as follows. Cell membrane homogenates (8 μg protein) are incubated for 60 minutes at 22° C. with 0.3 nM [$^3$H]methyl-spiperone in the absence or presence of the test compound in a buffer containing 50 mM Tris-HCl (pH 7.4), 120 mM NaCl, 5 mM KCl, 5 mM $MgCl_2$ and 5 mM EDTA. Nonspecific binding is determined in the presence of 10 μM (+)butaclamol. Following incubation, the samples are filtered rapidly under vacuum through glass fiber filters (GF/B, Packard) 67re-soaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is (+)butaclamol, which is tested in each experiment at several concentrations to obtain a competition curve from which its $IC_{50}$ is calculated, and from which the % inhibition at 1 μM as indicated in the following table is obtained.

Human Dopamine $D_3$ Receptor (Agonist Radioligand):

The purpose is to evaluate the affinity of compounds for the agonist site of the human dopamine $D_3$ receptor in transfected CHO cells determined in a radioligand binding assay according to Ricci et al in *J. Neuroimmunol.* (1998) 92:191. The experimental protocol is as follows. Cell membrane homogenates (4 μg protein) are incubated for 120 minutes at 22° C. with 0.15 nM [$^3$H]7-OH-DPAT in the absence or presence of the test compound in a buffer containing 50 mM Tris-HCl (pH 7.4), 5 mM KCl, 5 mM $MgCl_2$, 1 mM EDTA and 0.1% BSA. Nonspecific binding is determined in the presence of 10 μM (+)butaclamol. Following incubation, the samples are filtered rapidly under vacuum through glass fiber filters (GF/B, Packard) 68re-soaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is 7-OH-DPAT, which is tested in each experiment at several concentrations to obtain a competition curve from which its $IC_{50}$ is calculated, and from which the % inhibition at 1 μM as indicated in the following table is obtained.

Non-Selective α-Adrenergic Receptor (Antagonist Radioligand):

The purpose is to evaluate the affinity of compounds for the non-selective $α_{□}$-adrenergic receptor in the rat cerebral cortex determined in a radioligand binding assay according to Greengrass et al. in *Eur. J. Pharmacol.* (1979) 55: 323. The experimental protocol is as follows. Membrane homogenates of cerebral cortex (160 μg protein) are incubated for 60 minutes at 22° C. with 0.25 nM [$^3$H]prazosin in the absence or presence of the test compound in a buffer containing 50 mM Tris-HCl (pH 7.4), 150 mM NaCl, 5 mM EDTA and 0.1% BSA. Non-specific binding is determined in the presence of 0.5 μM prazosin. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is prazosin, which is tested in each experiment at several concentrations to obtain a competition curve from which its $IC_{50}$ is calculated.

Non-Selective Adrenergic $α_2$ Receptor (Antagonist Radioligand):

The purpose is to evaluate the affinity of compounds for the non-selective $_2$-adrenergic receptor in the rat cerebral cortex determined in a radioligand binding assay according to Uhlen et al. in *Pharmacol. Toxicol.* (1991) 69:341. The experimental protocol is as follows. Membrane homogenates of cerebral cortex (160 μg protein) are incubated for 60 minutes at 22° C. with 0.5 nM [$^3$H]RX 821002 in the absence or presence of the test compound in a buffer containing 50 mM Tris-HCl (pH 7.4), 2 mM $MgCl_2$ and 1 mM EDTA. Non-specific binding is determined in the presence of 100 μM(−)epinephrine. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is yohimbine, which is tested in each experiment at several concentrations to obtain a competition curve from which its $IC_{50}$ is calculated.

Human Adrenergic $\beta_1$ Receptor (Agonist Radioligand):

The purpose is to evaluate the affinity of compounds for the agonist site of the human $\beta_1$-adrenergic receptor in transfected HEK-293 cells determined in a radioligand binding assay according to Levin et al. in *J. Biol. Chem.* (2002) 277: 30429. The experimental protocol is as follows. Cell membrane homogenates (5 µg protein) are incubated for 60 minutes at 22° C. with 0.15 nM [$^3$H]CGP 12177 in the absence or presence of the test compound in a buffer containing 50 mM Tris-HCl (pH 7.4), 10 mM MgCl$_2$, 2 mM EDTA and 0.1% BSA. Nonspecific binding is determined in the presence of 50 µM alprenolol. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is atenolol, which is tested in each experiment at several concentrations to obtain a competition curve from which its IC$_{50}$ is calculated.

Human Adrenergic $\beta_2$ Receptor (Agonist Radioligand)

The purpose is to evaluate the affinity of compounds for the agonist site of the human $\beta_2$-adrenergic receptor in transfected CHO cells determined in a radioligand binding assay according to Joseph et al. in *Naunyn-Schmiedeberg's Arch. Pharmacol.* (2004) 369:525. The experimental protocol is as follows. Cell membrane homogenates (32 µg protein) are incubated for 120 minutes at 22° C. with 0.3 nM [$^3$H]CGP 12177 in the absence or presence of the test compound in a buffer containing 10 mM NaH$_2$PO$_4$/Na$_2$HPO$_4$ (pH 7.4), 85 mM NaCl, 30 mM KCl, 1 mM MgSO4, 5.5 mM glucose, 0.005% bacitracin and 0.1% BSA. Nonspecific binding is determined in the presence of 50 µM alprenolol. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is ICI 118551, which is tested in each experiment at several concentrations to obtain a competition curve from which its IC$_{50}$ is calculated.

Central Benzodiazepine Receptor (Agonist Radioligand)

The purpose is to evaluate the affinity of compounds for the agonist site of the central benzodiazepine receptor in the rat cerebral cortex determined in a radioligand binding assay according to Speth et al in *Life Sci.* (1979) 24:351. The experimental protocol is as follows. Membrane homogenates of cerebral cortex (80 µg protein) are incubated for 60 minutes at 4° C. with 0.4 nM [$^3$H]flunitrazepam in the absence or presence of the test compound in a buffer containing 50 mM Tris-HCl (pH 7.7). Non-specific binding is determined in the presence of 3 µM diazepam. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is diazepam, which is tested in each experiment at several concentrations to obtain a competition curve from which its IC$_{50}$ is calculated.

Human CB$_1$ Cannabinoid Receptor (Agonist Radioligand):

The purpose is to evaluate the affinity of compounds for the agonist site of the human CB$_1$ cannabinoid receptor in transfected CHO cells determined in a radioligand binding assay according to Rinaldi-Carmona in *J. Pharmacol. Exp. Ther.* (1996) 278:871. The experimental protocol is as follows. Cell membrane homogenates (20 µg protein) are incubated for 120 minutes at 37° C. with 0.5 nM [$^3$H]CP 55940 in the absence or presence of the test compound in a buffer containing 50 mM Tris-HCl (pH 7.4), 5 mM MgCl$_2$, 2.5 mM EDTA and 0.3% BSA. Non-specific binding is determined in the presence of 10 µM WIN 55212-2. Following incubation, the samples are filtered rapidly under vacuum through glass fiber filters (GF/B, Packard) presoaked with 0.3% PEI and rinsed several times with an ice-cold buffer containing 50 mM Tris-HCl (pH 7.4) and 0.5% BSA using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is CP 55940 which is tested in each experiment at several concentrations to obtain a competition curve from which its IC$_{50}$ is calculated.

Human Dopamine $D_{2S}$ Receptor (Antagonist Radioligand):

The purpose is to evaluate the affinity of compounds for the human dopamine $D_{2S}$ receptor in transfected HEK-293 cells determined in a radioligand binding assay according to Grandy et al in *Proc. Natl. Acad. Sci. USA* (1989) 86:9762. The experimental protocol is as follows. Cell membrane homogenates (8 µg protein) are incubated for 60 minutes at 22° C. with 0.3 nM [$^3$H]spiperone in the absence or presence of the test compound in a buffer containing 50 mM Tris-HCl (pH 7.4), 120 mM NaCl, 5 mM KCl, 5 mM MgCl$_2$ and 1 mM EDTA. Non-specific binding is determined in the presence of 10 µM (+)butaclamol. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is (+)butaclamol, which is tested in each experiment at several concentrations to obtain a competition curve from which its IC$_{50}$ is calculated.

Non-Selective GABA Receptor (Agonist Radioligand):

The purpose is to evaluate the affinity of compounds for the agonist site of the non-selective GABA receptor in the rat cerebral cortex determined in a radioligand binding assay according to Tsuji et al in *Antimicrob. Agents Chemother.* (1988) 32:190. The experimental protocol is as follows. Membrane homogenates of cerebral cortex (120 µg protein) are incubated for 60 minutes at 22° C. with 10 nM [$^3$H]GABA in the absence or presence of the test compound in a buffer containing 50 mM Tris-HCl (pH 7.4) and 2.5 mM CaCl$_2$. Non-specific binding is determined in the presence of 100 µM GABA. Following incubation, the samples are filtered rapidly under vacuum through glass fiber filters (GF/B, Packard) and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is GABA, which is tested in each experiment at several concentrations to obtain a competition curve from which its $IC_{50}$ is calculated.

Glycine Receptor (Strychnine Insensitive):

The purpose is to evaluate the affinity of compounds for the strychnine-insensitive glycine receptor in the rat cerebral cortex determined in a radioligand binding assay according to Baron et al in *J. Pharmacol. Exp. Ther.* (1996) 279: 62. The experimental protocol is as follows. Membrane homogenates of cerebral cortex (300 µg protein) are incubated for 45 minutes at 0° C. with 0.5 nM [$^3$H]MDL 105,519 in the absence or presence of the test compound in a buffer containing 50 mM Hepes/KOH (pH 7.5). Non-specific binding is determined in the presence of 1 mM glycine. Following incubation, the samples are filtered rapidly under vacuum through glass fiber filters (Filtermat A, Wallac) and rinsed several times with ice-cold 50 mM Hepes/KOH using a 48-sample cell harvester (Mach II, Tomtec). The filters are dried then counted for radioactivity in a scintillation counter (Betaplate 1204, Wallac) using a solid scintillator (Meltilex B/HS, Wallac). The results are expressed as a percent inhibition of the control radioligand specific binding. The standard reference compound is glycine, which is tested in each experiment at several concentrations to obtain a competition curve from which its $IC_{50}$ is calculated.

Human Muscarinic $M_1$ Receptor (Antagonist Radioligand):

The purpose is to evaluate the affinity of compounds for the human muscarinic $M_1$ receptor in transfected CHO cells determined in a radioligand binding assay according to Dorje et al in *J. Pharmacol. Exp. Ther.* (1991) 256:727. The experimental protocol is as follows. Cell membrane homogenates (45 µg protein) are incubated for 60 minutes at 22° C. with 2 nM [$^3$H]pirenzepine in the absence or presence of the test compound in a buffer containing 50 mM Tris-HCl (pH 7.4), 120 mM NaCl, 5 mM KCl, 5 mM $MgCl_2$ and 1 mM EDTA. Non-specific binding is determined in the presence of 1 µM atropine. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is pirenzepine, which is tested in each experiment at several concentrations to obtain a competition curve from which its $IC_{50}$ is calculated.

Human Muscarinic $M_2$ Receptor (Antagonist Radioligand):

The purpose is to evaluate the affinity of compounds for the human muscarinic $M_2$ receptor in transfected CHO cells determined in a radioligand binding assay according to Dorje et al in *J. Pharmacol. Exp. Ther.* (1991) 256:727. The experimental protocol is as follows. Cell membrane homogenates (60 µg protein) are incubated for 60 minutes at 22° C. with 2 nM [$^3$H]AF-DX 384 in the absence or presence of the test compound in a buffer containing 50 mM Tris-HCl (pH 7.4), 120 mM NaCl, 5 mM KCl, 5 mM $MgCl_2$ and 1 mM EDTA. Non-specific binding is determined in the presence of 1 µM atropine. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is methoctramine, which is tested in each experiment at several concentrations to obtain a competition curve from which its $IC_{50}$ is calculated.

Human Muscarinic $M_3$ Receptor (Antagonist Radioligand):

The purpose is to evaluate the affinity of compounds for the human muscarinic $M_2$ receptor in transfected CHO cells determined in a radioligand binding assay according to Peralta et al in *EMBO. J.* (1987) 6: 3923 The experimental protocol is as follows. Cell membrane homogenates (8 µg protein) are incubated for 60 minutes at 22° C. with 0.2 nM [$^3$H]-4-DAMP in the absence or presence of the test compound in a buffer containing 10 mM Tris-HCl (pH 7.4) and 2 mM EDTA. Non-specific binding is determined in the presence of 1 µM atropine. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is 4-DAMP, which is tested in each experiment at several concentrations to obtain a competition curve from which its $IC_{50}$ is calculated.

Non-Selective Serotonin (5-HT) Receptor (Agonist Radioligand)

The purpose is to evaluate the affinity of compounds for the agonist site of the non-selective 5-HT receptor in the rat cerebral cortex determined in a radioligand binding assay according to Peroutka et al in *Mol. Pharmacol.* (1979) 16:687. The experimental protocol is as follows. Membrane homogenates of cerebral cortex (144 µg protein) are incubated for 60 minutes at 37° C. with 2 nM [$^3$H]serotonin in the absence or presence of the test compound in a buffer containing 50 mM Tris-HCl (pH 7.4), 4 mM $CaCl_2$, 10 µM pargyline and 1 g/l ascorbic acid. Non-specific binding is determined in the presence of 10 µM serotonin. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is serotonin, which is tested in each experiment at several concentrations to obtain a competition curve from which its $IC_{50}$ is calculated.

Cl$^-$ Channel (GABA-Gated)

The purpose is to evaluate the affinity of compounds for the Cl$^-$ channel in the rat cerebral cortex determined in a radioligand binding assay according to Lewin et al in *Mol. Pharmacol.* (1989) 35:189. The experimental protocol is as follows. Membrane homogenates of cerebral cortex (120 µg protein) are incubated for 120 minutes at 22° C. with 3 nM [$^{35}$S]TBPS in the absence or presence of the test compound in a buffer containing 50 mM $Na_2HPO_4$/$KH_2PO_4$ (pH 7.4) and 500 mM NaCl. Non-specific binding is determined in the presence of 20 µM picrotoxinin. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is picrotoxinin, which is tested in each experiment at several concentrations to obtain a competition curve from which its $IC_{50}$ is calculated.

The invention claimed is:
1. A 1-substituted-2-azabicyclo[3.1.1]heptyl derivative represented by the structural formula (I):

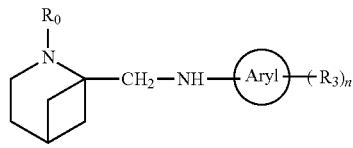

or the structural formula (II):

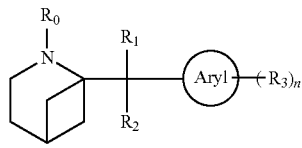

or the structural formula (III):

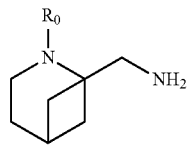

wherein:
$R_0$ is hydrogen or a nitrogen-protecting group selected from the group consisting of phenyl, benzyl, phenylethyl, naphthylmethyl, naphthylethyl, butoxycarbonyl, $C_{3-4}$ alkenyl, heteroaryl, heteroarylmethyl, heteroarylethyl and $C_{1-8}$ alkyl, wherein said phenyl, benzyl or heteroaryl is optionally substituted with one to three substituents independently selected from the group consisting of halogen, $C_{1-4}$ alkyl, $C_{1-4}$ alkoxy, trifluoromethyl, trifluoromethoxy, dimethylaminoethoxy, dimethylaminopropoxy, morpholinoethoxy, phenoxy, phenoxymethyl, heteroaryl and heteroarylmethyl;
$R_1$ is hydrogen and $R_2$ is hydroxyl, or $R_1$ in combination with $R_2$ is oxo or imino;
each $R_3$ is a substituent selected from the group consisting of fluoro, chloro, bromo, $C_{1-4}$ alkyl, $C_{1-4}$ alkoxy, $C_{1-4}$ alkylthio, cyano, phenyl, trifluoromethyl, trifluoromethoxy, amino, dimethylamino, heteroaryl and tert-butylcarboxylate; and
n is 0, 1, 2 or 3; and
Aryl is an optionally substituted aryl or heteroaryl group,
a pharmaceutically acceptable salt thereof, a stereochemically isomeric form thereof, or a solvate thereof.
2. A 1-substituted-2-azabicyclo[3.1.1]heptyl derivative according to claim 1, or a pharmaceutically acceptable salt thereof, or a stereochemically isomeric form thereof, or a solvate thereof, wherein Aryl is an optionally substituted phenyl group.
3. A 1-substituted-2-azabicyclo[3.1.1]heptyl derivative according to claim 1, wherein n is 0 or 1.
4. A 1-substituted-2-azabicyclo[3.1.1]heptyl derivative according to claim 2, wherein n is 0 or 1.
5. A 1-substituted-2-azabicyclo[3.1.1]heptyl derivative according to claim 1, a pharmaceutically acceptable salt thereof, a stereochemically isomeric form thereof, or a solvate thereof, wherein Aryl is an optionally substituted pyridin-3-yl or pyridin-2-yl group.
6. A 1-substituted-2-azabicyclo[3.1.1]heptyl derivative according to claim 5, wherein n is 0 or 1.
7. A 1-substituted-2-azabicyclo[3.1.1]heptyl derivative according to claim 6, wherein n is 1 and $R_3$ is chloro.
8. A 1-substituted-2-azabicyclo[3.1.1]heptyl derivative according to claim 5, being represented by the structural formula (II) wherein $R_1$ in combination with $R_2$ is oxo or imino.
9. A 1-substituted-2-azabicyclo[3.1.1]heptyl derivative according to claim 5, wherein $R_0$ is benzyl substituted in ortho and/or para positions with one to three methoxy or methyl groups, or $R_0$ is methyl, ethyl, isopropyl, n-propyl, n-butyl or isobutyl, or $R_0$ is pyridin-2-ylmethyl, pyridin-3-ylmethyl, pyridin-4-ylmethyl or pyridinylethyl, or $R_0$ is phenyl substituted in ortho, meta and/or para positions with one to three methoxy or methyl groups.
10. A method for producing a 1-substituted-2-azabicyclo[3.1.1]heptyl derivative according to claim 1 and being represented by the structural formula (II) wherein $R_1$ in combination with $R_2$ is oxo, comprising reacting a 1-cyano-2-$R_0$-substituted-2-azabicyclo[3.1.1]-heptane, wherein 0 is as defined in claim 20, with an optionally substituted aryl iodide, chloride or bromide represented by the structural formula Y-Aryl-$(R_3)_n$ wherein Y is iodo, chloro or bromo and wherein Aryl, n and $R_3$ are as defined in claim 1.
11. A method according to claim 10, wherein $R_0$ is not hydrogen, further comprising the step of cleaving off the N-protecting $R_0$ substituent.
12. A pharmaceutical composition comprising a therapeutically effective amount of a 1-substituted-2-azabicyclo[3.1.1]heptyl derivative according to claim 1.
13. A pharmaceutical composition according to claim 12, further comprising one or more pharmaceutically acceptable excipients.
14. A 1-cyano-2-$R_0$-substituted-2-azabicyclo[3.1.1]-heptane compound, wherein $R_0$ is hydrogen or a nitrogen-protecting group selected from the group consisting of phenyl, phenylethyl, naphthylmethyl, naphthylethyl, butoxycarbonyl, $C_{3-4}$ alkenyl, heteroaryl, heteroarylmethyl, heteroarylethyl and $C_{1-8}$ alkyl, wherein said phenyl or heteroaryl is optionally substituted with one to three substituents independently selected from the group consisting of halogen, $C_{1-4}$ alkyl, $C_{1-4}$ alkoxy, trifluoromethyl, trifluoromethoxy, dimethyl-aminoethoxy, dimethylaminopropoxy, morpholinoethoxy, phenoxy, phenoxy-methyl, heteroaryl and heteroarylmethyl, or $R_0$ is benzyl substituted with one to three substituents independently selected from the group consisting of halogen, $C_{1-8}$ alkyl, $C_{1-8}$ alkoxy, trifluoromethyl, trifluoromethoxy, dimethylaminoethoxy, dimethylaminopropoxy, morpholinoethoxy, phenoxy, phenoxymethyl, heteroaryl and heteroarylmethyl, with the proviso that said compound is not 1-cyano-2-benzyl-2-azabicyclo[3.1.1]heptane.
15. A compound according to claim 14, wherein $R_0$ is selected from the group consisting of p-methoxybenzyl, isopropyl, n-propyl, isobutyl, n-butyl, p-methylbenzyl, pyridin-2-ylmethyl, pyridin-3-ylmethyl, pyridin-4-ylmethyl, 2,4-dimethoxybenzyl, p-methoxyphenyl, ethyl, and methyl.

16. A 1-substituted-2-azabicyclo[3.1.1]heptyl derivative according to claim 8, wherein:
$R_1$ in combination with $R_2$ is oxo,
n is 1, and
Aryl is pyridin-3-yl substituted with chloro.

17. A 1-substituted-2-azabicyclo[3.1.1]heptyl derivative according to claim 8, wherein:
$R_1$ in combination with $R_2$ is oxo,
n is 0, and
Aryl is pyridin-3-yl.

18. A 1-substituted-2-azabicyclo[3.1.1]heptyl derivative according to claim 6, wherein:
$R_0$ is hydrogen,
$R_1$ is hydrogen,
$R_2$ is hydroxyl,
n is 0, and
Aryl is pyridin-3-yl or pyridin-2-yl.

19. A 1-substituted-2-azabicyclo[3.1.1]heptyl derivative according to claim 6, being represented by the structural formula (I) wherein:
Aryl is pyridin-3-yl or pyridin-2-yl,
n is 0, and
$R_0$ is hydrogen or benzyl.

20. A 1-substituted-2-azabicyclo[3.1.1]heptyl derivative according to claim 6, being represented by the structural formula (III) wherein:
Aryl is pyridin-2-yl,
n is 0, and
$R_0$ is selected from the group consisting of benzyl, p-methoxybenzyl, isopropyl, n-propyl, isobutyl, n-butyl, p-methylbenzyl, pyridin-2-ylmethyl, pyridin-3-ylmethyl, pyridin-4-ylmethyl, 2,4-dimethoxybenzyl, p-methoxyphenyl, ethyl, and methyl.

* * * * *

UNITED STATES PATENT AND TRADEMARK OFFICE
CERTIFICATE OF CORRECTION

| | |
|---|---|
| PATENT NO. | : 8,809,365 B2 |
| APPLICATION NO. | : 13/504618 |
| DATED | : August 19, 2014 |
| INVENTOR(S) | : Christian Stevens et al. |

It is certified that error appears in the above-identified patent and that said Letters Patent is hereby corrected as shown below:

IN THE CLAIMS

Column 52, Line 34, replace "claim 20" with --claim 1--.

Signed and Sealed this
Sixth Day of January, 2015

Michelle K. Lee
*Deputy Director of the United States Patent and Trademark Office*